(12) United States Patent
Olde et al.

(10) Patent No.: US 9,289,544 B2
(45) Date of Patent: Mar. 22, 2016

(54) METHOD AND DEVICE FOR DETECTING A CONFIGURATION OF WITHDRAWAL AND RETURN DEVICES

(75) Inventors: Bo Olde, Lund (SE); Kristian Solem, Kavlinge (SE)

(73) Assignee: Gambro Lundia AB, Lund (SE)

( * ) Notice: Subject to any disclaimer, the term of this patent is extended or adjusted under 35 U.S.C. 154(b) by 575 days.

(21) Appl. No.: 13/519,146

(22) PCT Filed: Dec. 22, 2010

(86) PCT No.: PCT/EP2010/070550
§ 371 (c)(1),
(2), (4) Date: Aug. 23, 2012

(87) PCT Pub. No.: WO2011/080188
PCT Pub. Date: Jul. 7, 2011

(65) Prior Publication Data
US 2013/0150766 A1     Jun. 13, 2013

Related U.S. Application Data

(60) Provisional application No. 61/290,317, filed on Dec. 28, 2009.

(30) Foreign Application Priority Data

Dec. 28, 2009   (SE) ..................................... 0951032

(51) Int. Cl.
*A61M 1/30*     (2006.01)
*A61M 1/36*     (2006.01)
*A61M 5/168*     (2006.01)

(52) U.S. Cl.
CPC ............... *A61M 1/30* (2013.01); *A61M 1/3653* (2013.01); *A61M 1/3656* (2014.02); *A61M 5/16859* (2013.01); *A61M 2205/13* (2013.01); *A61M 2205/3331* (2013.01); *A61M 2230/04* (2013.01)

(58) Field of Classification Search
CPC ............ A61M 1/3653; A61M 1/3656; A61M 2205/13; A61M 2205/3331
USPC .................. 604/4.01, 5.04; 210/739, 741
See application file for complete search history.

(56) References Cited

U.S. PATENT DOCUMENTS 6,623,443 B1   9/2003   Polaschegg
7,435,342 B2   10/2008   Tsukamoto
(Continued)

FOREIGN PATENT DOCUMENTS

DE    197 34 002    9/1998
DE    199 01 078    2/2000
(Continued)

OTHER PUBLICATIONS

PCT Search Report and Written Opinion for PCT/EP2010/070550 dated Apr. 15, 2011 (14 pages).
(Continued)

*Primary Examiner* — Leslie Deak
(74) *Attorney, Agent, or Firm* — Mueting, Raasch & Gebhardt, P.A.

(57) ABSTRACT

A device is arranged to detect a configuration of withdrawal and return devices (1, 14, 111, 112, 211, 212, 702, 703, 802, 803) coupling an extracorporeal blood flow circuit (20) to a cardiovascular system of a subject. The device comprises a signal processor (29), which is configured to receive a primary measurement signal obtained by a primary pressure sensor (4a, 4b, 4c) in the extracorporeal blood flow circuit (20). The device is further configured to process the primary measurement signal for extraction of primary pressure data originating from a subject pulse generator (3') in the cardiovascular system or extracorporeal blood flow circuit (20), the primary pressure data comprising at least a part of a first pulse from the subject pulse generator (3'). The device is also configured to calculate a parameter value from the primary pressure data and to determine the configuration based at least partly on the parameter value.

29 Claims, 26 Drawing Sheets

(56) References Cited

U.S. PATENT DOCUMENTS

| | | |
|---|---|---|
| 7,988,854 B2 | 8/2011 | Tsukamoto |
| 8,715,216 B2 | 5/2014 | Olde |
| 8,718,957 B2 | 5/2014 | Furmanski |
| 8,911,629 B2 | 12/2014 | Tsukamoto |
| 2005/0010118 A1 | 1/2005 | Toyoda |
| 2005/0051472 A1 | 3/2005 | Chionh |
| 2006/0272421 A1* | 12/2006 | Frinak et al. ............ 73/710 |
| 2008/0195060 A1 | 8/2008 | Roger |
| 2011/0106466 A1 | 5/2011 | Furmanski |
| 2015/0019170 A1 | 1/2015 | Solem |

FOREIGN PATENT DOCUMENTS

| | | |
|---|---|---|
| EP | 0330 761 | 9/1989 |
| EP | 1 813 188 | 8/2007 |
| JP | 2006-198141 | 8/2006 |
| JP | 2006-304836 | 11/2006 |
| WO | WO 97/10013 | 3/1997 |
| WO | 2005/062973 | 7/2005 |
| WO | WO 2009/127683 | 10/2009 |
| WO | 2009/156174 | 12/2009 |
| WO | 2009/156175 | 12/2009 |

OTHER PUBLICATIONS

Schneditz, "Theoretical and Practical Issues in Recirculation; Assessment of Vascular Access," EDTNA ERCA Journal, 1998, Apr.-Jun.; 24(2):3-6.

* cited by examiner

Time (s)

Time (s)

Time (s)

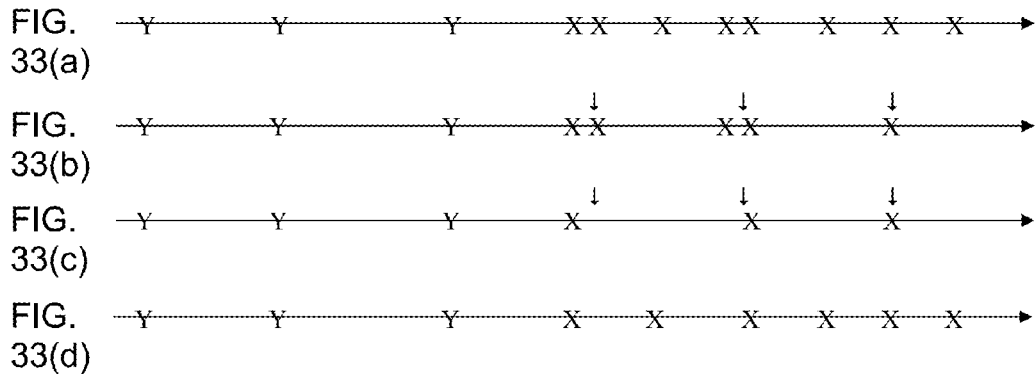
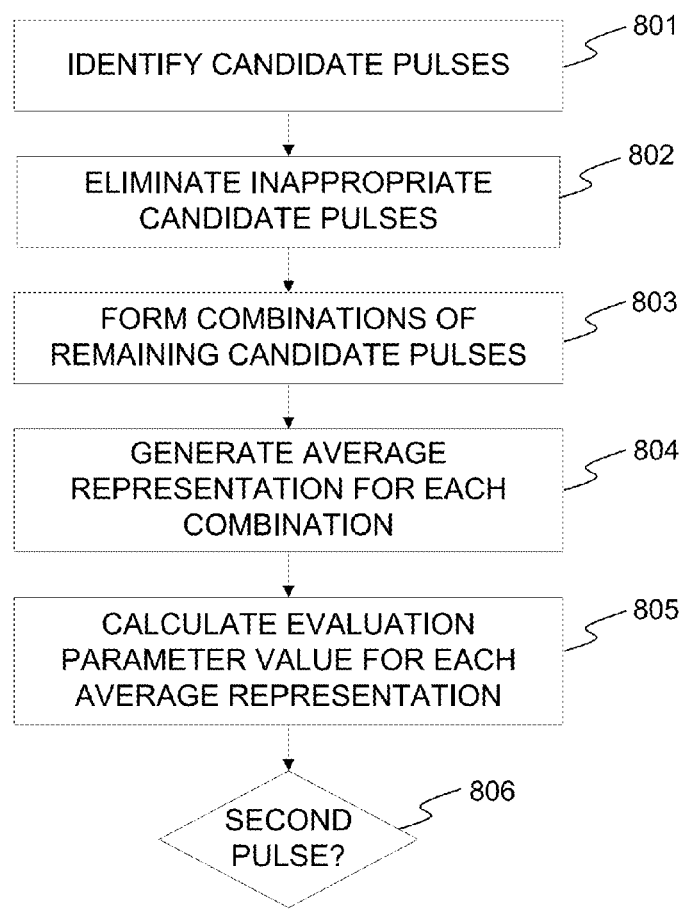
FIG. 34

METHOD AND DEVICE FOR DETECTING A CONFIGURATION OF WITHDRAWAL AND RETURN DEVICES

This application is a U.S. National Stage Application of International Application No. PCT/EP2010/070550, filed Dec. 22, 2010, which was published in English on Jul. 7, 2011 as International Patent Publication WO 2011/080188 A1, and which claims the benefit under 35 U.S.C. 119(e) of U.S. Provisional Application No. 61/290,317 filed Dec. 28, 2009. International Application No. PCT/EP2010/070550 also claims priority to Swedish Application No. 0951032-2, filed Dec. 28, 2009.

TECHNICAL FIELD

The present invention generally relates to detection of configuration of access devices, and in particular to detection based on a pressure measurement. The present invention is e.g. applicable in arrangements for extracorporeal blood treatment.

BACKGROUND ART

In extracorporeal blood treatment, blood is taken out of a subject, treated and then reintroduced into the subject by means of an extracorporeal blood flow circuit. Generally, the blood is circulated through the circuit by one or more pumping devices. The circuit is connected to a blood vessel access of the patient, typically via one or more access devices, such as needles, which are inserted into the blood vessel access. Such extracorporeal blood treatments include hemodialysis, hemodiafiltration, hemofiltration, plasmapheresis, bloodbanking, blood fraction separation (e.g. cells) of donor blood, etc.

In extracorporeal blood treatment, it is vital to minimize the risk for malfunctions in the extracorporeal blood flow circuit, since these may lead to inefficient treatment due to impaired delivery of hemodialysis prescription having potentially severe effects on the condition of the subject.

Malfunctions may be caused by i) accidental misplacement of the access devices for blood extraction (withdrawal and return, e.g. arterial and venous needles/catheters) or ii) faulty connection of the access devices to the blood lines. For instance, the connection of the access devices to the blood vessels may be reversed, causing recirculation of the treated blood during extra-corporeal circulation such that the dialyzed blood returning through the venous line is drawn back into the arterial line without having passed through the heart and thereby reducing the treatment dose given to the patient, which may have negative consequences to the patient's health both in the short and long term perspective. Another example of malfunction includes a reversed connection of the blood lines to the access devices.

These malfunctions all originate in a "connection system" between the patient and the extracorporeal blood flow circuit. The connection system includes one or more access devices and possibly one or more releasable connectors for attaching the access devices to tubing in the extracorporeal blood flow circuit.

Recirculation in extracorporeal blood treatment arises when the whole or a fraction of treated extracorporeal blood flow returns directly to the inlet of the extracorporeal blood line instead of flowing back to the heart.

There are several reasons for recirculation, for instance a) low access blood flow $Q_a$ compared to the blood flow $Q_b$ of extra-corporeal circulation, specific problems related to the b) blood access physiology or return of treated blood directly to inlet due c) to too close positioning of needles. However, another common cause for needle problems is accidental misplacement of the arterial and venous access devices or tubes to reversing the configuration and causing a substantial recirculation and significant reduction of treatment dose.

To avoid recirculation of the treated blood during extracorporeal treatment the arterial access must be placed in an upstream position compared to the venous access. Studies have shown that reversed needles fault may occur in approximately one of ten treatments.

Situations with access recirculation require intervention. To this end, an apparatus for extracorporeal blood treatment may include one or more surveillance devices that detect either recirculation in general or specifically the reversal of the needles.

Methods of access surveillance include clinical examination, urea or tracer recirculation measurement, continuous wave Doppler methods, duplex ultrasonography, and radiograph angiography.

A method involving continuous wave Doppler measurements to detect access function related recirculation by ultrasound dilution is disclosed in EDTNA ERCA J 1998 April-June; 24(2):3-6 "Theoretical and practical issues in recirculation; assessment of vascular access". This method involves continuous wave Doppler measurements where a reversed position of the needles is detected by the Doppler frequencies being higher with the pump on than with the pump off.

Urea recirculation measurements involves comparing the blood urea taken from the access lines with that from a peripheral vein. When there is no recirculation, the urea in the arterial line and peripheral vein should be the same. However, this method will measure not only any access recirculation, but also the so called cardio-pulmonary recirculation. Cardio-pulmonary recirculation occurs because the treated blood traveling back towards the heart will mix with blood returning from the body, be pumped by the heart through the lungs and back to the heart where it will be pumped back into the body, and a fraction of this arterial blood is directed towards the access. This means that a fraction of the blood going out to the access will come from the newly treated blood. Just as with access recirculation this cardio-pulmonary recirculation therefore causes some newly treated blood to enter the extra-corporeal circulation directly, without having passed the main parts of the body in between. This urea method will therefore measure the sum of access and cardio-pulmonary recirculation.

Hematocrit dilution has also been promoted as an indicator. However, the known methods require special training and/or additional laboratory tests. Hence, there is a need for a method for detecting the configuration of withdrawal and return lines in a cardiovascular access that may be applied each time a subject undergoes extracorporeal blood treatment.

No integrated means in dialysis machines exist today which allow automatic detection of reversed needles. Since recirculation does not disturb the treatment in any other way than decreasing the treatment efficiency, it may go undetected throughout the whole treatment, and there is a large need for an automatic detection device. Various devices and methods have been disclosed for recirculation measurement, however, none of these are fully integrated and automatic. Furthermore, even if recirculation is detected, there is still a need to distinguish between various causes for recirculation, in particular reversed needles.

One example of another kind of malfunction in the extracorporeal blood flow circuit, which however is not attempted to be remedied by the present invention, is disclosed in JP2006198141. This documents deals with a connection mistake between arterial and venous detection lines between a dialyzer and pressure sensors, resulting in reversed pressure measurements, a potentially directly harmful situation if not discovered in time. Hence, this document relates to a problem and solution which is remote and significantly different from the problem of the present invention.

SUMMARY

It is an object of the invention to at least partly overcome one or more of the above-identified limitations of the prior art. Specifically, it is an object to provide an alternative or complementary technique for detecting a reverse configuration of withdrawal and return devices coupling an extracorporeal blood flow circuit to a cardiovascular system using pressure measurements. Hence, it is an object to provide a technique for detecting a reversed connection between an extracorporeal blood circuit and a cardiovascular system.

This and other objects, which will appear from the description below, are at least partly achieved by means of a method, a device, and a computer program product according to the independent claims, embodiments thereof being defined by the dependent claims.

A first aspect of a first inventive concept of the invention is a device for detecting a configuration of withdrawal and return devices coupling an extracorporeal blood flow circuit to a cardiovascular system of a subject, the device comprising a signal processor configured to receive a primary measurement signal obtained by a primary pressure sensor in the extracorporeal blood flow circuit, process the primary measurement signal for extraction of primary pressure data originating from a subject pulse generator in the cardiovascular system or extracorporeal blood flow circuit, the primary pressure data comprising at least a part of a subject pulse from the subject pulse generator; calculate a parameter value from the primary pressure data; and determine the configuration based at least partly on the parameter value.

In one embodiment, the configuration is determined by comparing the parameter value with a reference parameter value.

In one embodiment, the device is further configured to receive a secondary measurement signal obtained from a secondary sensor.

In one embodiment, the secondary sensor is a pressure sensor in the extracorporeal blood flow circuit, and wherein said secondary measurement signal is processed for extraction of secondary pressure data originating from said subject pulse generator, and wherein said parameter value is calculated from the primary pressure data and secondary pressure data.

In one embodiment, the primary pressure sensor is located on a venous side of the extracorporeal blood flow circuit and the secondary pressure sensor is located on an arterial side of the extracorporeal system.

In one embodiment, the parameter value is represented by a pressure amplitude measure of the primary pressure data.

In one embodiment, the pressure amplitude measure comprises an arterial pressure amplitude or a venous pressure amplitude.

In one embodiment, the parameter value is represented by a pressure amplitude ratio of said primary pressure data and said secondary pressure data.

In one embodiment, the pressure amplitude ratio in a reversed configuration is greater than the pressure amplitude ratio in a normal configuration.

In one embodiment, the parameter value represents a time delay of a pressure pulse detected by said primary pressure sensor at a first instance in time and said pressure pulse subsequently detected by said secondary pressure sensor at a second instance in time. Alternatively, the parameter value represents a time delay between a first pressure pulse obtained by said primary pressure sensor and a second pressure pulse obtained by a secondary pressure sensor.

In one embodiment, further to calculating, the signal processor is further configured to extract shape indicative data from the primary pressure data and matching the shape indicative data with shape reference data.

In one embodiment, the parameter value represents a deviation between the shape indicative data and the shape reference data. Alternatively, the parameter value is a correlation measure between shape indicative data from the primary pressure data and reference shape indicative pressure data.

In one embodiment, the shape reference data represents a temporal pulse profile of the subject pulse generator.

In one embodiment, the shape reference data represents a frequency spectrum of the subject pulse generator.

In one embodiment, the withdrawal and return devices comprise single or double lumen needles or catheters.

In other embodiments, the parameter value has been derived from one or more of a plurality of monitoring sessions of one subject, a plurality of monitoring sessions of two or more subjects, and a mathematical model.

In one embodiment, the configuration comprises a normal configuration and a reverse configuration and wherein in said normal configuration a withdrawal device is in an upstream position of said cardiovascular system for withdrawal of fluid and a return device is in a downstream position of said cardiovascular system for return of fluid and wherein in said reverse configuration the positioning of the access devices is reversed. Hence, in a normal configuration the return device is in a downstream position with respect to the withdrawal device and in a reverse configuration the return device is in an upstream position with respect to the withdrawal device.

In one embodiment, the signal processor is further configured to aggregate a plurality of pulses within an aggregation time window in the measurement signal.

In one embodiment, the device is further configured to issue an alarm subsequent to determining a reverse configuration of access devices.

In one embodiment, the parameter represents a deviation in transit time of the subject pulse from the subject pulse generator to the primary pressure sensor and the secondary pressure sensor.

A second aspect of the invention is a method for detecting a configuration of withdrawal and return devices coupling an extracorporeal blood flow circuit to a cardiovascular system of a subject, the method comprising: receiving a primary measurement signal obtained by a primary pressure sensor in the extracorporeal blood flow circuit, processing the primary measurement signal for extraction of primary pressure data originating from a subject pulse generator in the cardiovascular system or extracorporeal blood flow circuit, the primary pressure data comprising at least a part of a subject pulse from the subject pulse generator, calculating a parameter value from the primary pressure data, and determining the configuration based at least partly on the parameter value.

In one embodiment, the configuration is determined by comparing the parameter value with a reference parameter value.

In one embodiment, the method further comprises receiving a secondary measurement signal obtained from a secondary sensor.

In one embodiment, the method further comprises extracting shape indicative data from the primary pressure data and matching the shape indicative data with shape reference data.

In one embodiment, the method further comprises extracting the shape reference data from a secondary measurement signal received from a secondary sensor.

In one embodiment, the method further comprises aggregating a plurality of pulses within an aggregation time window in the measurement signal.

In one embodiment, the method further comprises issuing an alarm subsequent to determining a reverse configuration of access devices.

A third aspect of the invention is a computer-readable medium comprising computer instructions which, when executed by a processor, cause the processor to perform the method of the second aspect.

A fourth aspect of the invention is a device for detecting a configuration of withdrawal and return devices coupling an extracorporeal blood flow circuit to a cardiovascular system of a subject, said device comprising: means for receiving a primary measurement signal obtained by a primary pressure sensor in the extracorporeal blood flow circuit; means for processing the primary measurement signal for extraction of primary pressure data originating from a subject pulse generator in the cardiovascular system or extracorporeal blood flow circuit, the primary pressure data comprising at least a part of a subject pulse from the subject pulse generator; means for calculating a parameter value from the primary pressure data; and means for determining the configuration based at least partly on the parameter value.

According to one embodiment, a plurality of pulses are aggregated to enhance noise reduction. Preferably, an aggregate comprise at least twenty pulses to allow for sufficient extraction of parameter values associated with any of amplitude, phase, shape of a pulse profile or any combinations thereof.

Timing information from the measurement may be used to allow for accurate alignment in the aggregation process. The timing information may be obtained from the measurement signal or otherwise. The timing information is indicative of the timing of the pressure pulses in the measurement signal. Subsequently, the measurement signal is processed based on the timing information, to calculate a value of an evaluation parameter which is indicative of the relative configuration of access devices in a blood access. Based on the resulting value of the evaluation parameter, it is decided whether the access device configuration is normal or reversed, typically by comparing the resulting value to a threshold value.

Thus, the provision of timing information allows for signal enhancement by identifying and averaging pulse segments in one or more measurement signals.

Although the present invention preferably applies to on-line processing of measurement signals, i.e. during, e.g. concurrently, a treatment, it may also apply to off-line processing, for instance subsequent to or separate from a treatment such as upon studying the efficiency of a treatment. The processing may for instance involve pre-processing including general signal filtration, removal of particular signal noise and artefacts, such as from a running pump, and signal analysis. The cardiovascular system, for instance a blood circuit of a human or an animal, may also be referred to as a fluid system or fluid circuit.

Embodiments of the second to fourth aspects of the first inventive concept may correspond to the above-identified embodiments of the first aspect of the first inventive concept.

A fifth aspect of the invention is a device for detecting a reversed configuration of withdrawal and return devices coupling an extracorporeal blood flow circuit to a cardiovascular system of a subject, the device comprising a signal processor configured to: receive a primary measurement signal obtained by a primary pressure sensor in the extracorporeal blood flow circuit; process the primary measurement signal for extraction of primary pressure data originating from a pump pulse generator in the extracorporeal blood flow circuit, the primary pressure data comprising at least a part of a pump pulse from the pump pulse generator; calculate a parameter value from the primary pressure data, the parameter value being indicative of a cross-talk pressure pattern generated from a combination of pressure pulses from the pump pulse generator obtained by the primary pressure sensor from two directions, one passing through the cardiovascular system of the subject and the other from the pump pulse generator within the extracorporeal circuit; and determine the reversed configuration based at least partly on the parameter value. This may particularly be used for detection of the reversed configuration by comparing effects of pressure pulse cross-talk between venous and an arterial branch contributions in the extracorporeal circuit A sixth aspect of the invention is a method for detecting a configuration of withdrawal and return devices coupling an extracorporeal blood flow circuit to a cardiovascular system of a subject, the method comprising: receiving a primary measurement signal obtained by a primary pressure sensor in the extracorporeal blood flow circuit; processing the primary measurement signal for extraction of primary pressure data originating from a pump pulse generator in the extracorporeal blood flow circuit, the primary pressure data comprising at least a part of a subject pulse from the subject pulse generator; calculating a parameter value from the primary pressure data, the parameter value being indicative of a cross-talk pressure pattern generated from a combination of pressure pulses from the pump pulse generator obtained by the primary pressure sensor from two directions, one passing through the cardiovascular system of the subject and the other from the pump pulse generator within the extracorporeal circuit; and determining the configuration based at least partly on the parameter value.

The attributes primary and secondary have been used to distinguish equivalents, for instance primary and secondary pressure data and primary and secondary pressure sensors, and do not indicate certain order or importance.

The signal processor of the device of the first aspect of the invention may further be configured to carry out any of the steps of the methods according to the second and sixth aspects of the invention.

Still other objectives, features, aspects and advantages of the present invention will appear from the following detailed description, from the attached claims as well as from the drawings and the appendixes.

BRIEF DESCRIPTION OF THE DRAWINGS

Embodiments of the inventive concepts will now be described in more detail with reference to the accompanying schematic drawings.

FIG. 33(a)-(d), as presented in Appendix B, illustrate processing of candidate pulses identified in a measurement signal.

FIG. 34, as presented in Appendix B, is a flow chart of part of a monitoring process according to the second inventive concept.

DETAILED DESCRIPTION OF EXAMPLE

Embodiments

In the following, different embodiments for detecting a normal and/or reversed configuration of access devices will be described with reference to an exemplifying circuit for extracorporeal blood treatment. In particular, the present invention discloses a solution involving venous and/or arterial line pressure measurements during for instance dialysis for monitoring the configuration of withdrawal and return lines at a cardiovascular access.

Throughout the following description, like elements are designated by the same reference signs.

I. GENERAL

Figure 1:
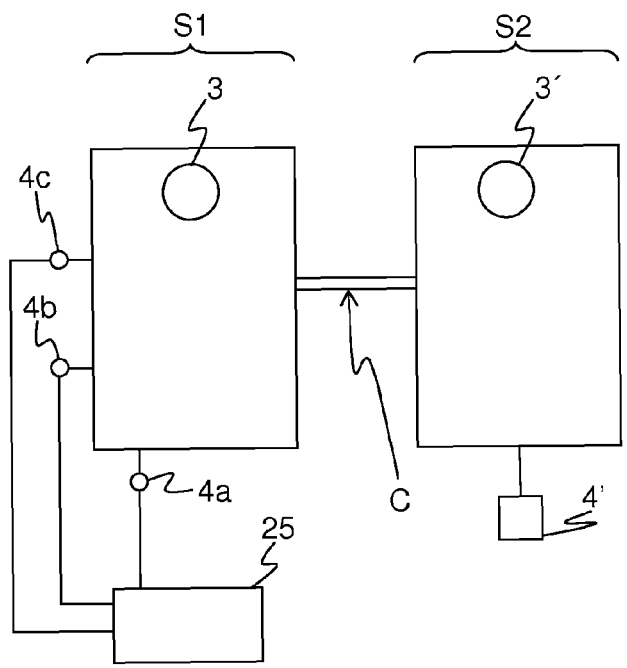
FIG. 1 is a schematic view of a general fluid arrangement in which the inventive concepts may be used for monitoring the configuration of a fluid connection.

FIG. 1 illustrates a general fluid arrangement in which a fluid connection C is established between a first fluid containing system S1 and a second fluid containing system S2. The fluid connection C may or may not transfer fluid from one system to the other. A first pulse generator 3 is arranged to generate a series of pressure waves in the fluid within the first system S1, and a second pulse generator 3' is arranged to generate a series of pressure waves in the fluid within the second system S2. Pressure sensors 4a to 4c are arranged to measure the fluid pressure in the first system S1. As long as the fluid connection C is intact, pressure waves generated by the second pulse generator 3' will travel from the second system S2 to the first system S1, and thus second pulses originating from the second pulse generator 3' will be detected by the pressure sensors 4a to 4c in addition to first pulses originating from the first pulse generator 3. It is to be noted that either one of the first and second pulse generators 3, 3' may include more than one pulse-generating device. Further, any such pulse-generating device may or may not be part of the respective fluid containing system S1, S2.

As used herein, a "pressure wave" denotes a mechanical wave in the form of a disturbance that travels or propagates through a material or substance. The pressure waves typically propagate in the fluid at a velocity of about 3-20 m/s. The pressure sensor generates measurement data that forms a pressure pulse for each pressure wave. A "pressure pulse" or "pulse" is thus a set of data samples that define a local increase or decrease (depending on implementation) in signal magnitude within a time-dependent measurement signal ("pressure signal"). The pressure pulses appear at a rate proportional to the generation rate of the pressure waves at the pulse generator. The pressure sensor may be of any type, e.g. operating by resistive, capacitive, inductive, magnetic or optical sensing, and using one or more diaphragms, bellows, Bourdon tubes, piezo-electrical components, semiconductor components, strain gauges, resonant wires, photo-plethysmography (PPG), accelerometers, bioimpedance, etc.

The fluid arrangement of FIG. 1 further includes a surveillance device 25 which is connected to the pressure sensor 4c, and possibly to one or more further pressure sensors 4a, 4b, as indicated in FIG. 1. Thereby, the surveillance device 25 acquires one or more measurement signals that are time-dependent to provide a real time representation of the fluid pressure in the first system S1. The surveillance device 25 monitors the configuration of the fluid connection C, based on the principle that characteristics, such as magnitude, shape and/or phase, of the first and/or second pulses vary depending on the configuration of the connection. A malfunction in the connection alter the characteristics of the pulse and upon detection of such an irregularity the surveillance device 25 may issue an alarm or warning signal, and/or alert a control system of the first or second fluid containing systems S1, S2 to take appropriate action.

The surveillance device 25 is thus configured to continuously process the time-dependent measurement signal(s) to determine whether pressure characteristics associated with a normal or irregular configuration are detected. Typically, the determination involves analyzing the measurement signal(s), or a pre-processed version thereof, in the time domain to calculate a value of an evaluation parameter which is indicative of the characteristics of the first and/or second pulses in the measurement signal(s). Depending on implementation, the surveillance device 25 may use digital components or analogue components, or a combination thereof, for receiving and processing the measurement signal(s).

In the following, references to a subject pulse generator or second pulse generator relates to a physiological pulse generator of the subject, such as the heart, breathing system or autonomous system or a pulse generator coupled to a subject, such as a blood pressure cuff or other external pulse generator. Subject pulses or second pulses, are generated from the subject pulse generator or second pulse generator. An interference pulse generator or first pulse generator may be present in the extracorporeal system, and may include a pump, such as a peristaltic pump. Interference pulses or first pulses are generated by the interference pulse generator or first pulse generator. The interference pulses or first pulses may also be used for detection of configuration of withdrawal and return devices due to a cross-talk effect in the pressure measurement signals differing in normal and reversed configurations.

II. EXAMPLE OF A VASCULAR ACCESS AND EXTRACORPOREAL CIRCUIT

Figure 2:
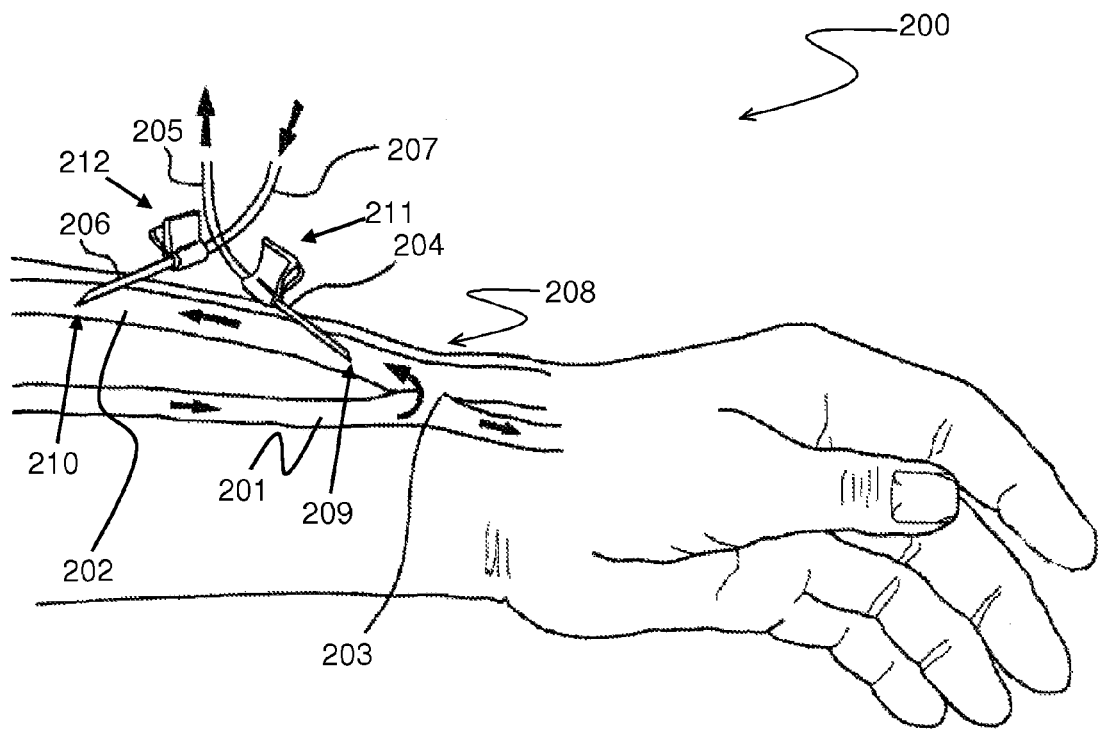
FIG. 2 is a partially schematic view of a forearm of a subject provided with an arterial/venous (AV) fistula.

FIG. 2. discloses a forearm 200 of a subject. The forearm 200 comprises an artery 201, in this case the radial artery, and a vein 202, in this case the cephalic vein. The blood flow in the artery (201) and vein (202) is indicated with arrows. Openings are surgically created in the artery 201 and the vein 202 and the openings are connected to form an anastomosis 203, in which the arterial blood flow is cross-circuited to the vein. Such a configuration with the anastomosis and nearby sections of the artery 201 and vein 202 are commonly referred to as a fistula 208. Due to the fistula, the blood flow through the artery and vein is increased and the vein forms a thickened area downstream of the connecting openings. When the fistula has matured a few months after surgery, the vein is thicker and may be punctured repeatedly. Normally, the thickened vein area is called a fistula.

An arterial or withdrawal device 211 in the form of a needle 204, to which is connected a piece of arterial or withdrawal tube 205, is placed in an upstream position 209 in the fistula, in the enlarged vein close to the connected anastomosis openings and a venous or return device 212 also in the form of a needle 206, to which is connected a piece of venous or return tube 207, is placed in a position downstream 210 of the arterial or withdrawal needle 204, normally at least five centimeters downstream thereof. The withdrawal 205 and return 207 tubes are connected to an extracorporeal circuit (not shown) such as described in FIG. 3. In use, the withdrawal tube 205 may transport blood from the artery 201 via the arterial or withdrawal needle 204 to an inlet of the extracorporeal circuit, and the return tube 207 then returns the treated blood from an outlet of the extracorporeal circuit to the vein 202 via the venous or return needle 206. Arrows at the ends of the blood lines (205, 207) indicate the direction of blood flow in a normal configuration. In a reversed configuration of the needles/catheters (204, 206), connection of blood lines (205, 207) to the needles or connection of the blood lines to the extracorporeal circuit, the arrows would be reversed.

The vascular access may also be an arterio-venous graft, Scribner-shunt, one or more catheters, a double lumen catheter or other similar arrangements. For the purpose of the following discussion, the blood vessel access is assumed to be a fistula. The withdrawal and return needles may also be catheters. The withdrawal and return devices generally comprises a needle or catheter, a tubing and a connector (not shown) connecting the tubing to the needle or catheter.

Figure 3:
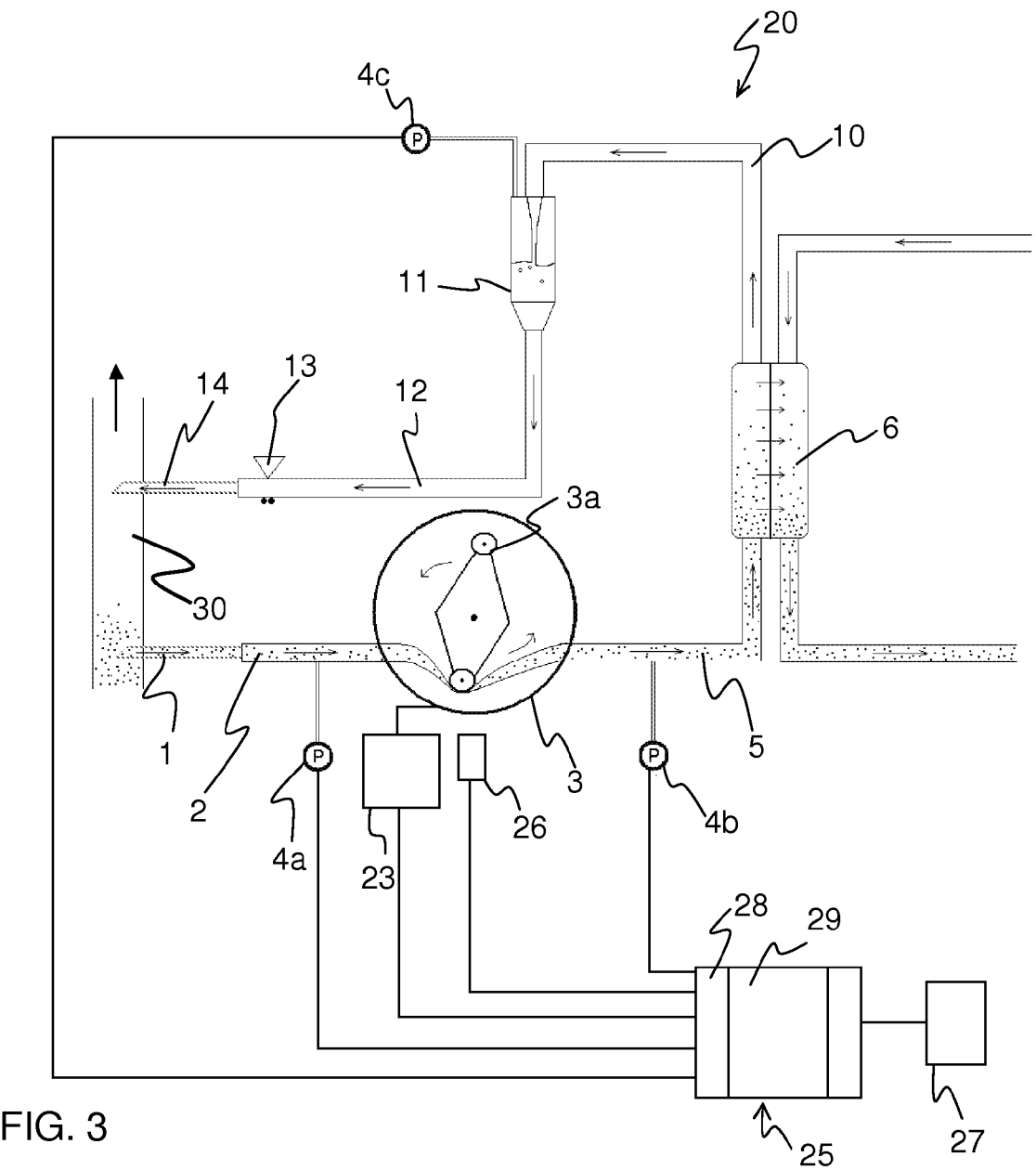
FIG. 3 is a schematic view of a system for hemodialysis treatment including an extracorporeal blood flow circuit.

The needles 204 and 206 of FIG. 2 are connected to a tube system, shown in FIG. 3, forming an extracorporeal blood flow circuit 20 of the type which is used for dialysis. Withdrawal or artery needle 1 and return or venous needle 14 are shown connected to a vessel 30 of the subject, which vessel is a part of the cardiovascular system of the subject. The extracorporeal blood flow circuit comprises a blood pump 3, such as a peristaltic pump. At the inlet of the pump 3 there is a pressure sensor 4a, hereafter referred to as arterial sensor, which measures the pressure before the pump in the withdrawal tube segment 2. The blood pump 3 propels the blood from the fistula, through the withdrawal needle 1, via a pre-dialyser tube segment 5, to the blood-side of a dialyser 6. Many dialysis machines are additionally provided with a pressure sensor 4b that measures the pressure between the blood pump 3 and the dialyser 6. The blood is lead via a post-dialyser tube segment 10 from the blood-side of the dialyser 6 to a venous drip chamber or deaeration chamber 11 and from there back to the subject via the return tube segment 12 and return needle 14. A pressure sensor 4c, hereafter referred to as venous sensor, is provided to measure the pressure on the venous side of the dialyser 6. In the illustrated example, the pressure sensor 4c measures the pressure in the venous drip chamber. Both the withdrawal needle 1 and the return needle 14 are connected to the subject by means of the vascular access.

As discussed by way of introduction, it may be vital to monitor the fluid connection to the blood vessel access with respect to anomalies. In many dialysis machines, one or more of said pressure detectors 4a-4c are not present. However, there will be at least one venous pressure sensor. The following description is focused on detection of the configuration of access devices in the fluid connection based on a measurement signal from one or more of the pressure sensors.

Further in FIG. 3, a control unit 23 is provided, i.e., to control the blood flow in the circuit 20 by controlling the revolution speed of the blood pump 3. The extracorporeal blood flow circuit 20 and the control unit 23 may form part of an apparatus for extracorporeal blood treatment, such as a dialysis machine. Although not shown or discussed further it is to be understood that such an apparatus performs many other functions, e.g. controlling the flow of dialysis fluid, controlling the temperature and composition of the dialysis fluid, etc.

Also in FIG. 3, a surveillance device 25 is configured to detect the configuration of the access devices in the fluid connection between blood accesses of the subject and the extracorporeal blood flow circuit 20, specifically by detecting the presence of a predetermined pressure response determined by magnitude, shape and phase, or timing, and indicative of a normal configuration of the access devices, the pressure response for instance originating from the patient's heart in a blood pressure signal. Absence of such a predetermined pressure response is taken as an indication of a reversed positioning of the access devices, and brings the device 25 to activate an alarm or notification for the staff to check the configuration of withdrawal and return devices and adjust the configuration if necessary. The surveillance device 25 is at least connected to receive a measurement signal of the pressure sensor 4c. The device 25 may also be connected to further pressure sensors such as 4a, 4b, as well as any additional pressure sensors included in the extracorporeal blood flow circuit 20. As indicated in FIG. 3, the device 25 may also be connected to the control unit 23. Alternatively or additionally, the device 25 may be connected to a measurement device 26, such as a rotary encoder (e.g. conductive, optical or magnetic) or the like, for indicating the frequency and phase of the blood pump 3. The device 25 is tethered or wirelessly connected to a local or remote device 27 for generating an audible/visual/tactile alarm or warning signal. The surveillance device 25 and/or the alarm device 27 may alternatively be incorporated as part of apparatus such as a dialysis monitor.

Additionally, in FIG. 3, the surveillance device 25 comprises a data acquisition part 28 for pre-processing the incoming signal(s), e.g. including an A/D converter with a required minimum sampling rate and resolution, one or more signal amplifiers, one or more filters to remove undesired components of the incoming signal(s), such as offset, high frequency noise and supply voltage disturbances.

In the examples given herein, the data acquisition part 28 comprises a DAQ card USB-6210 from National Instruments with a sampling rate of 1 kHz and resolution of 16 bits, an operation amplifying circuit AD620 from Analogue Devices, a high-pass filter with a cut-off frequency of 0.03 Hz (i.a., for removal of signal offset) together with a low-pass filter with a cut-off frequency of 402 Hz (i.a., for removal of high frequency noise). To obtain a short convergence time, a low-order filter is used for the high-pass filter. Furthermore, the data acquisition part 28 may include an additional fixed band-pass filter with upper and lower cut-off frequencies of 0.5 Hz and 2.7 Hz, respectively, which corresponds to heart pulse rates between 30 and 160 beats per minute. This filter may be used to suppress disturbances outside the frequency interval of interest. Corresponding filters may be applied to extract pressure pulses originating from breathing or other physiological signals, which may be used separately or in combination with the heart pulse rates to determine the configuration of access devices.

Figure 4:
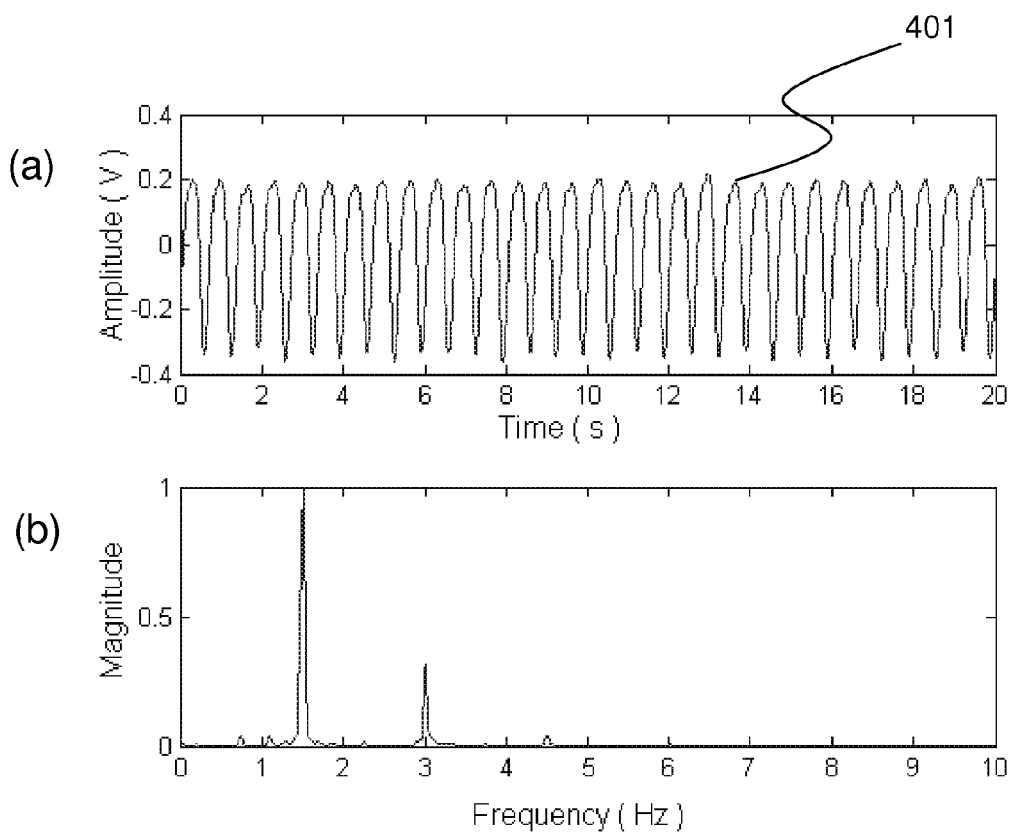
FIG. 4(a) is a plot in the time domain of a venous pressure signal containing both pump frequency components and heart frequency components.
FIG. 4(b) is a plot of the corresponding signal in the frequency domain.

After the pre-processing in the data acquisition part 28, the pre-processed pressure signal is provided as input to a main data processing part 29, which executes the inventive data processing. The data processing part 29 may also be referred to as a signal processor 29. FIG. 4(a) shows an example of such a pre-processed pressure signal 401 in the time domain, and FIG. 4(b) shows the corresponding power spectrum, i.e. the pre-processed pressure signal in the frequency domain. The power spectrum reveals that the detected pressure signal contains a number of different frequency components emanating from the blood pump 3. In the illustrated example, there is a frequency component at the base frequency ($f_0$) of the blood pump (at 1.5 Hz in this example), as well as its harmonics $2f_0$, $3f_0$ and $4f_0$. The base frequency, also denoted pump frequency in the following, is the frequency of the pump strokes that generate pressure waves in the extracorporeal circuit 20. For example, in a peristaltic pump of the type shown in FIG. 3, two pump strokes are generated for each full revolution of the rotor 3a. FIG. 4(b) also indicates the presence of a frequency component at half the pump frequency ($0.5f_0$) and harmonics thereof, in this example at least $f_0$, $1.5f_0$, $2f_0$ and $2.5f_0$. FIG. 4(b) also shows a heart signal (at 1.1 Hz) which in this example is approximately 40 times weaker than the blood pump signal at the base frequency $f_0$.

Typically, the surveillance device 25 is configured to continuously process the time-dependent pressure signal(s) to isolate any second pulses originating from a physiological pulse generator, such as the heart or breathing system. This processing is schematically depicted in the flow chart of FIG. 5. The illustrated processing involves a step 501 of obtaining a first pulse profile u(n) which is a predicted temporal signal profile of the second pulse(s), and a step 502 of filtering the pressure signal d(n), or a pre-processed version thereof, in the time-domain, using the first pulse profile u(n), to essentially eliminate or cancel the first pulse(s) while retaining the second pulse(s) contained in d(n). In the context of the present disclosure, n indicates a sample number and is thus equivalent to a (relative) time point in a time-dependent signal. In step 503, the resulting filtered signal e(n) is then analysed for the purpose of monitoring the aforesaid predetermined pressure response or parameter for a heart signal corresponding to a normal or reversed configuration.

The first pulse profile is a shape template or standard signal profile, typically given as a time-sequence of data values, which reflects the shape of the first pulse in the time domain. The first pulse profile is also denoted "predicted signal profile" in the following description.

By "essentially eliminating" is meant that the first pulse(s) is(are) removed from the pressure signal to such an extent that the second pulse(s) can be detected and analysed for the purpose of monitoring the aforesaid functional state or parameter.

By filtering the pressure signal in the time-domain, using the first pulse profile, it is possible to essentially eliminate the first pulses and still retain the second pulses, even if the first and second pulses overlap or nearly overlap in the frequency domain. Such a frequency overlap is not unlikely, e.g. if one or both of the first and second pulses is made up of a combination of frequencies or frequency ranges.

Figure 6:
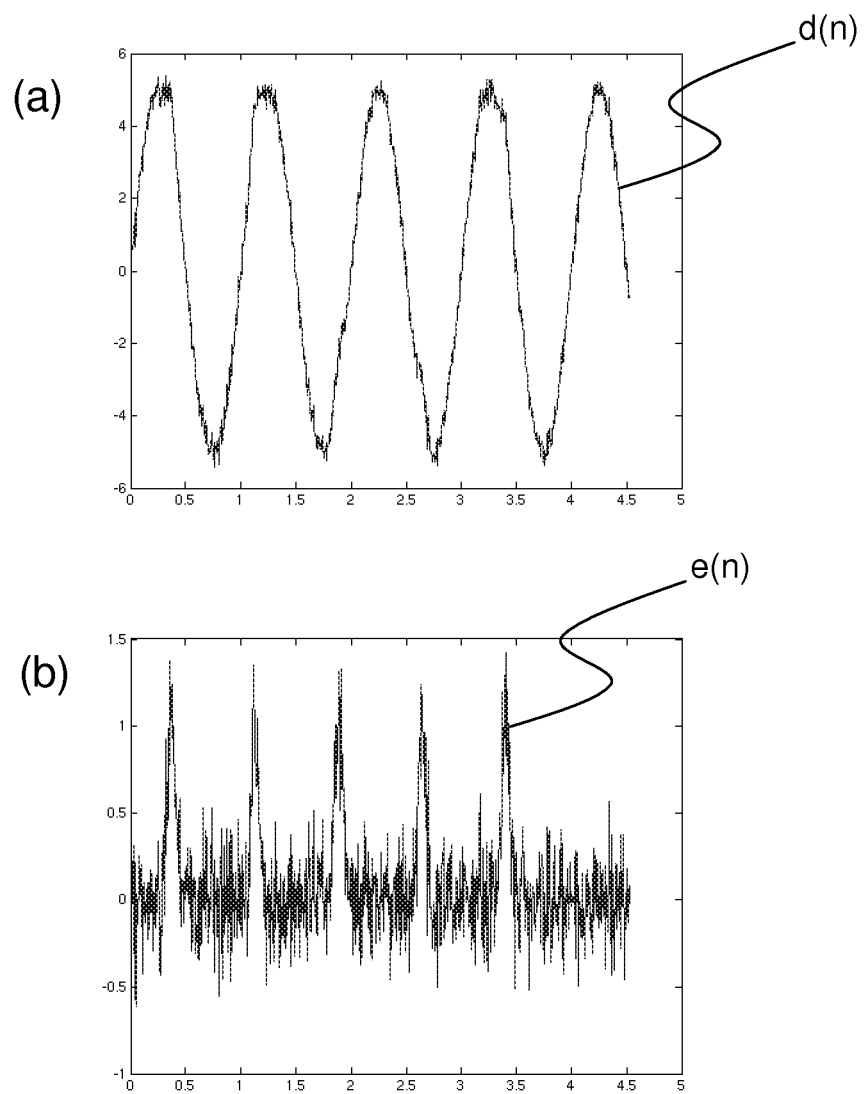
FIG. 6(a) is a plot of a pressure signal as a function of time.
FIG. 6(b) is a plot of the pressure signal after filtering.

The effectiveness of the inventive filtering is exemplified in FIG. 6, in which FIG. 6(a) shows an example of a time-dependent pressure signal d(n) containing first and second pulses with a relative magnitude of 10:1. The first and second pulses have a frequency of 1 Hz and 1.33 Hz, respectively. Due to the difference in magnitude, the pressure signal is dominated by the first pulses, i.e. pump pulses. FIG. 6(b) shows the time-dependent filtered signal e(n) that is obtained after applying the inventive filtering technique to the pressure signal d(n). The filtered signal e(n) is made up of second pulses and noise.

Figure 5:
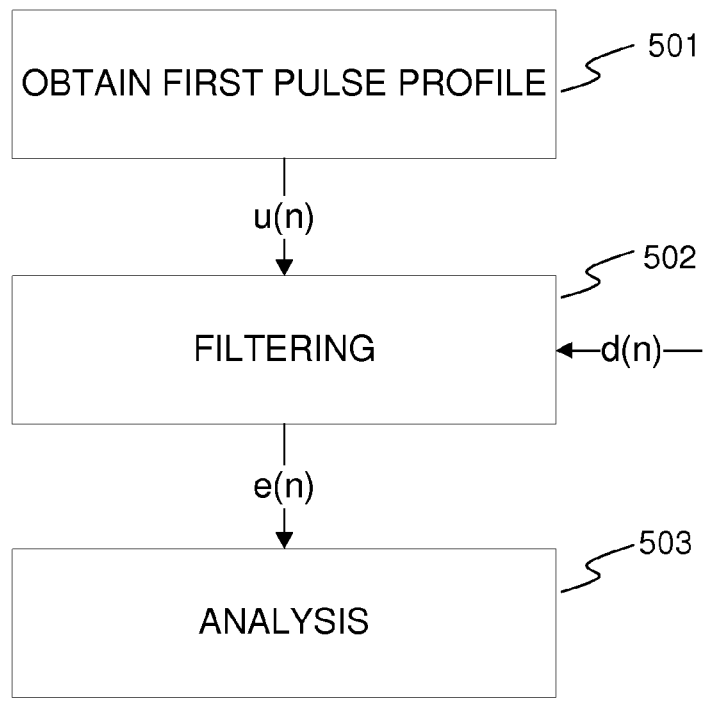
FIG. 5 is a flow chart of a monitoring process according to an embodiment of the invention.

The main data processing part 29 executes the aforesaid steps 501-503 of FIG. 5. In step 502, the main data processing part 29 operates to filter the pre-processed pressure signal in the time domain, and outputs a filtered signal or monitoring signal (e(n) in FIG. 5) in which the signal components of the blood pump 3 have been removed. The monitoring signal still contains any signal components that originate from the subject (cf. FIG. 6(b)), such as pressure pulses caused by the beating of the patient's heart, breathing or other physiological signals. There are a number of sources to cyclic physiological phenomena that may generate pressure pulses in the blood stream of the patient, including the heart, the breathing system, or the vasomotor, which is controlled by the autonomic nervous system. Thus, the monitoring signal may contain pressure pulses resulting from a combination of cyclic phenomena in the patient. Generally speaking, the signal components in the monitoring signal may originate from any type of physiological phenomenon in the patient, or combinations thereof, be it cyclic or non-cyclic, repetitive or non-repetitive, autonomous or non-autonomous. The signal components may additionally involve artificial origin, for instance by a separate, external pressure inducing component, such as integrated in a blood pressure cuff, or the blood pressure cuff itself with pressure waves induced by puffing air into the cuff.

Depending on implementation, the surveillance device 25 may be configured to apply further filtering to the monitoring signal to isolate signal components originating from a single cyclic phenomenon in the patient. Alternatively, such signal component filtering is done during the pre-processing of the pressure signal (by the data acquisition part 28). The signal component filtering may be done in the frequency domain, e.g. by applying a cut-off or band pass filter, since the signal components of the different cyclic phenomena in the patient are typically separated in the frequency domain. Generally, the heart frequency is about 0.5-4 Hz, the breathing frequency is about 0.15-0.4 Hz, the frequency of the autonomous system for regulation of blood pressure is about 0.04-0.14 Hz, the frequency of the autonomous system for regulation of body temperature is about 0.04 Hz.

Alternatively or additionally, vibrations, and thus pressure waves, resulting from coughing, sneezing, vomiting, seizures may also be used to detect the positioning of needles.

The surveillance device 25 may be configured to monitor the heart rate of the patient, by identifying heart pulses in the monitoring signal.

The surveillance device 25 may be configured to collect and store data on the evolution of the amplitude, phase, shape, etc, e.g. for subsequent analysis in connection with treatment efficiency and positioning of access devices since the reference signal may be corrected for the actual position of needles, e.g. distance.

The surveillance device 25 may be configured to monitor the configuration of the access devices coupling the patient with the extracorporeal circuit 20, in particular for detecting positioning according to a reverse configuration. This may be done by monitoring characteristics of a signal component originating from, e.g., the patient's heart or breathing system in the monitoring signal or the monitoring signal itself where the composite signal is analysed. It may further be done by monitoring the characteristics of a signal component originating from a pulse generator in the extracorporeal circuit, e.g. a pump, as a result of a cross-talk effect arising from influence of components arriving from two directions, i.e. the venous and arterials branches of the extracorporeal circuit.

The extracorporeal circuit 20 may have the option to operate in a hemodiafiltration mode (HDF mode), in which the control unit 23 activates a second pumping device (HDF pump, not shown) to supply an infusion solution into the blood line upstream and/or downstream of the dialyser 6, e.g. into one or more of tube segments 2, 5, 10 or 12.

The obtaining of the predicted signal profile of pulses originating from a pump will be described below in the section "Obtaining the predicted signal profile of first pulses".

In addition, one of the pressure sensors 4a, 4b, 4c or even an external signal source indicated by 4' in FIG. 1, such as a photoplethysmograph (PPG), an electrocardiograph (ECG) signal or a blood pressure cuff may be used as a timing reference to the pressure based signal originating from the actuation of the heart.

III. NORMAL AND REVERSED CONFIGURATIONS

Figure 7:
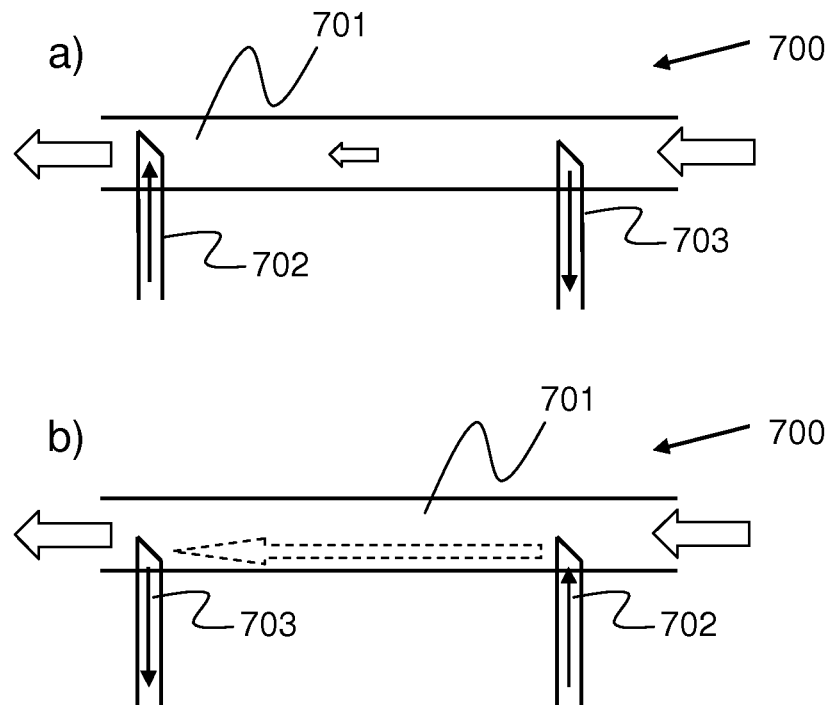
FIG. 7(a) is a schematically view of withdrawal and return devices in a normal configuration at an access site.
FIG. 7(b) is a plot of the corresponding access site with the withdrawal and return devices in a reversed configuration.

FIG. 7 illustrates an access site 700 with a blood vessel access 701 and access devices 702 and 703 in a normal a) and a reversed b) configuration. The blood flow in the blood vessel access and access devices are indicated by arrows. In normal configuration a), the arterial access device 703 is positioned upstream for extracting blood and the venous access device 702 is positioned downstream for returning blood to the blood vessel access. In reversed configuration b), the arterial access device 703 is positioned downstream and the venous access device upstream, with the consequence of treated blood being returned upstream and being extracted downstream by the arterial access device. In the reversed configuration, some of the blood is withdrawn and redialyzed without being passed through the blood circulating through the body, with significantly reduced treatment efficiency as a consequence.

Figure 8:
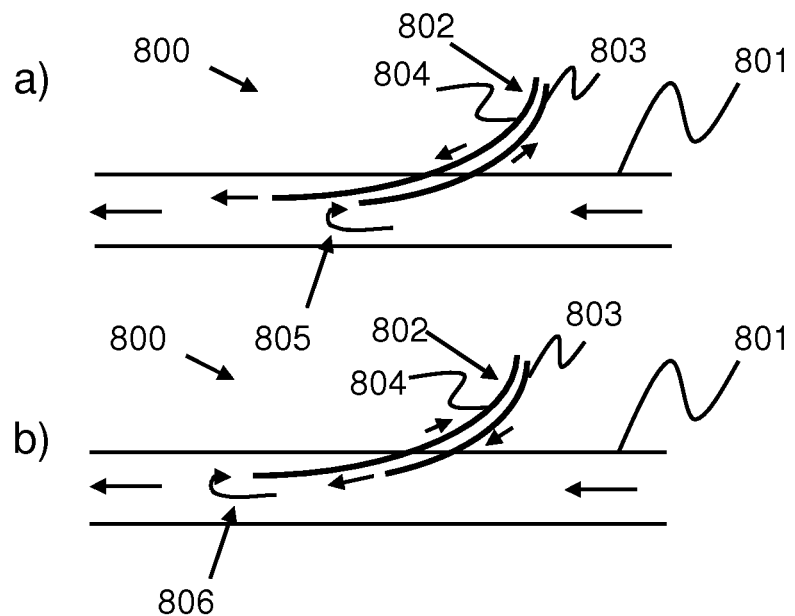
FIG. 8(a) is a schematically view of withdrawal and return lines of a double lumen needle or catheter in a normal configuration at an access site.
FIG. 8(b) is a plot of the corresponding access site with the withdrawal and return lines in a reversed configuration.

In extracorporeal blood treatments, two needles are commonly used to puncture the skin to gain access to the patient's blood supply. The arterial needle removes the blood, and the venous needle is used to return the treated blood to the patient. Alternatively, a double lumen catheter may be used as shown in FIG. 8. A double lumen catheter comprises two parallel channels which terminate at a distance from each other. One lumen removes the blood, and the other lumen is used to return the treated blood to the patient. FIG. 8 shows an access site 800 with a venous blood vessel access 801 and a double lumen needle 802 inserted and having an arterial lumen 803 and a venous lumen 804. Section a) of FIG. 8 illustrates a normal situation with the withdrawal and return blood lines (not shown) connected to the right respective lumen, hence the arterial lumen 803 is withdrawing blood and the venous lumen 804 is returning blood. Flow directions are indicated with arrows. Section b) of FIG. 8 illustrates a situation where the blood lines to the respective lumen have been reversed, such that the venous lumen 804 withdraws blood and the arterial lumen returns blood, resulting in recirculation since the arterial lumen 803 is upstream in relation to the venous 804 lumen. Another type of malfunction may occur if the double lumen catheter is inserted in a reversed direction into a blood vessel, then the inlet and outlet of the double lumen catheter will be reversed with respect to the flow in the blood vessel, i.e. with a configuration according to section a) of FIG. 8, but with blood flow of venous access directed towards the openings of the catheter.

IV. ANALYSIS

Figure 9:
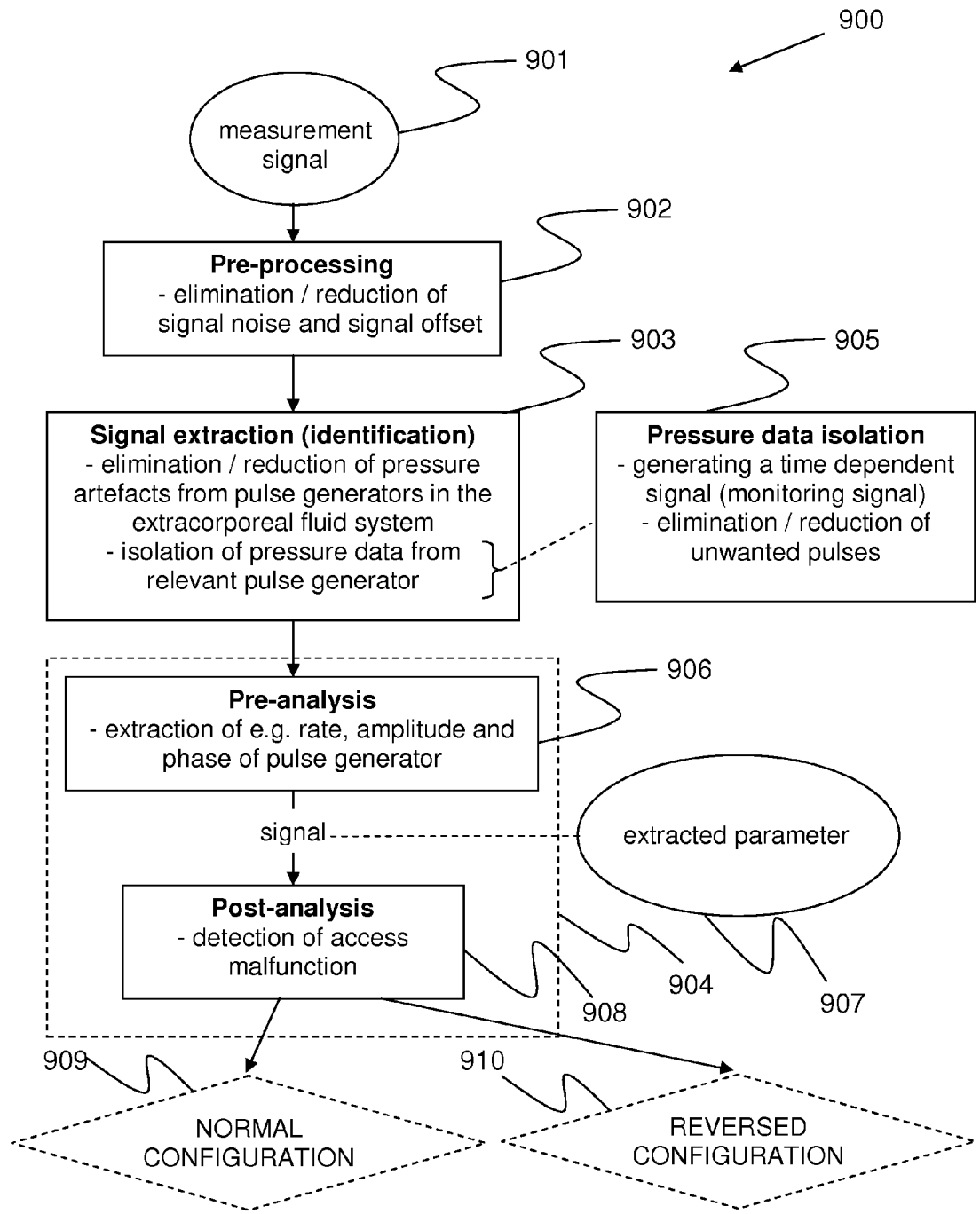
FIG. 9 is a flow chart of a monitoring process according to an embodiment of the invention.

FIG. 9 is a flow chart that illustrates steps of a signal analysis process 900 according to an embodiment of the present invention. It is initiated by receiving a measurement signal 901, e.g. from the venous, arterial and/or system pressure sensors, e.g. 4b of FIG. 3, comprising a number of pressure induced signal components.

The measurement signal comprises signals originating from one or more sources and thus constitutes a composite signal of the signals from said sources. The measurement signal may be used without further processing, although preferably, the measurement signal may be processed for extraction of pressure data originating from a pulse generator in the cardiovascular system. The extraction may be performed by filtering to remove unwanted pressure data.

In the cardiovascular system, the pulse generator may be a physiological phenomena, such as the pulse from the heart or breathing from the lungs. Other physiological phenomena pulse generators may be an autonomous system for blood pressure regulation and an autonomous system for body temperature regulation.

In the extracorporeal system, the pulse generator may be a fluid pump, such as a blood pump. The pump may be on the blood side or the fluid side of the extracorporeal blood flow circuit in a dialysis system. The pump may be of any type that generates pressure waves, for instance a peristaltic type of pump.

The pulse generators may be repetitive, such as the heart, breathing or pump or non-repetitive, such as pulses generated from coughing, sneezing, vomiting or seizures. Additionally, pulses may also be generated from separate, independent pulse generators, such as by rapid inflation of a blood pressure cuff to induce a pressure wave which propagates from the body part it is coupled to a blood vessel of the cardiovascular system.

The signal analysis process may be divided into a pre-processing part 902, a signal extraction part 903 and an analysis part 904. The pre-processing part 902 includes elimination or reduction of signal noise, e.g. measurement noise, and signal offset, as detailed in the section above relating to the data acquisition part 28. The signal extraction part 903 involves elimination or reduction of pressure artefacts originating from pulse generators in the extracorporeal blood flow circuit and isolation of pressure data originating from a relevant physiological phenomenon. In the context of the present disclosure, "pressure data isolation" 905 denotes a process of generating a time-dependent signal (also denoted monitoring signal herein) which is free or substantially free from pressure modulations caused by any unwanted physiological phenomena. Such unwanted physiological phenomena may vary between different applications, but generally include breathing, coughing, etc. In a case of cross-talk pressure modulations, all such unwanted physiological phenomena may be eliminated. The elimination of signal noise and signal offset, as well as the elimination of pressure artefacts, may be included in algorithms for pressure data isolation. For instance, the measurement signal may be band pass filtered or low pass filtered to isolate a heart signal, in a way such that signal noise and/or signal offset and/or pressure artefacts are eliminated from the measurement signal. The elimination of pressure artefacts may thus be performed before, after or during the pressure data isolation.

In pre-analysis step 906 of the analysis part 904, one or more specific signal analysis algorithm(s) are applied for extraction of e.g. rate, amplitude and phase or timing of the one or more physiological phenomena. In post-analysis step 908, based on predetermined criteria, the output 907 of the signal analysis algorithm(s) is analysed, e.g. by pattern recognition, for signs a withdrawal and return line configuration, for instance indicated by detection of a normal configuration 909 or detection of a reversed configuration 910. The pressure data is then analysed and a parameter value is calculated. The access configuration is then determined based at least partly on the parameter value. The parameter value is compared to a threshold value, interval or range to determine a specific condition. Alternatively or additionally, a signal feature may be extracted from pressure data and compared to a reference value, from which comparison a resulting parameter value may be compared to a threshold or interval. The reference data may comprise predicted data, predetermined data, secondary measurement data, or any combinations thereof.

The calculation may be designed such that the parameter value represents time, amplitude or shape of the pulse. However, the detection may also be performed in the frequency domain by analysis of the amplitude and/or phase spectrum.

In the general case, one or more pumps are running or other sources of cyclic or non-cyclic repetitive and non-repetitive artefacts are present during the data acquisition. Information on the cyclic disturbances may be known from external sources, e.g. other sensors, or may be estimated or reconstructed from system parameters.

Cyclic pressure artefacts may originate from operating a peristaltic pump, repetitive actuation of valves, movements of membranes in balancing chambers. According to the findings in connection with the present invention, artefacts may also originate from mechanical resonance of system components such as swinging movements of blood line energized by e.g. a pump. Frequencies of blood line movements are given by the tube lengths and harmonics thereof and by the beating between any frequencies involved, i.e. between different self-oscillations and pump frequencies. These frequencies may differ between the venous and arterial lines. Mechanical fixation of the blood lines and other free components may remedy the problem of mechanical resonance. Alternatively, an operator may be instructed to touch or jolt the blood lines to identify natural frequencies associated with the blood lines, which information may be used in the analysis for improved removal of components not belonging to the pressure data of interest.

Examples of non-cyclic artefacts are subject movement, valve actuation, movements of tubings etc.

Various techniques for signal extraction will be discussed in a section further below.

The invention has mainly been described above with reference to a few embodiments. However, as is readily appreciated by a person skilled in the art, other embodiments than the ones disclosed above are equally possible within the scope and spirit of the invention, which is defined and limited only be the appended patent claims.

For example, the illustrated embodiments are applicable for surveillance of all types of extracorporeal blood flow circuits in which blood is taken from a patient's circulation to have a process applied to it before it is returned to the circulation. Such blood flow circuits include hemodialysis, hemofiltration, hemodiafiltration, plasmapheresis, aphaeresis, extra-corporeal membrane oxygenation, assisted blood circulation, and extracorporeal liver support/dialysis, bloodbanking, blood fraction separation (e.g. cells) of donor blood, etc.

Further, the inventive monitoring techniques are applicable to any type of pumping device that generates pressure pulses in the first fluid containing system, not only rotary peristaltic pumps as disclosed above, but also other types of positive displacement pumps, such as linear peristaltic pumps, diaphragm pumps, as well as centrifugal pumps.

Tests have shown that different evaluation parameters may be preferable in different situations. For example, the use of variance or averaged sum of multiple pulses may increase the detectability in various situations. Pattern recognition may be resorted when other detection methods fail.

Furthermore, although it may generally be enough for evaluation purposes to involve one parameter value, it may be advantageous to base an evaluation on combinations of two or more parameter values, such as to improve the reliability of the detection of configuration. The reliability may also be enhanced by increasing the evaluation time period. It may further be advantageous to increase the resolution in the measurements to further improve the reliability.

In the following, a few examples of situations involving extraction of a fluid from a flow, where recirculation reduces the efficiency of the process. In these examples, any non-physiological pulse generator may be utilized, such as a pressure generator.

In one example, the fluid connection is provided between a blood processing circuit and a container/machine, wherein blood is pumped from one container/machine through a blood processing device in the blood processing circuit and back to the container/machine, or to another container/machine downstream of the blood processing device. The blood processing device could be any known device configured to modify and/or analyse the blood.

In another example, the fluid connection is provided in a heart lung machine, which mechanically circulates and oxygenates blood for the body while bypassing the heart and lungs.

In a further example, the fluid connection is provided in an arrangement for cleaning and disinfecting the dialysis solution flow path of a dialysis machine, which pumps a cleaning fluid via a flow path to a dialyser tubing. The cleaning fluid may e.g. be hot water, etc.

In all of these examples, and in other applications related to medical treatment of human or animal patients, it may be vital to monitor the positioning of access devices. Such monitoring can be accomplished according to the inventive concepts disclosed herein.

V. DETECTING REVERSED CONFIGURATION OF ACCESS DEVICES

This section relates to detection of an access configuration. It is based on analysis of one or more physiological or other signals that are extracted out of one or more pressure signals acquired from an extra-corporeal fluid system. Although mainly referring to a single signal, such as the heart amplitude in a venous (Hv) or arterial (Ha) pressure signal, the examples may be equally valid for combinations of signals, such as a ratio (R=Hv/Ha) between the heart amplitude in the venous and arterial pressure signals.

Although the strength of pulse pressure wave in the arterial signal in general is stronger than the pulse pressure wave in the venous signal, techniques described in the section Signal extraction and in greater detail in the Appendices A and B enables sufficient extraction of pressure data representing the pulse pressure wave in the venous signal.

On a general level, the detection, may involve calculating an evaluation parameter value based on the isolated pressure data resulting from the aforesaid signal extraction. The evaluation parameter value is then analysed as part of a process for detecting an access configuration.

In the context of the present disclosure, irregularities in the characteristics of a pulse may imply that the pulse has deviating magnitude, shape, phase, timing or other measurable attributes. The assessment of normal or irregularity may involve calculating an evaluation parameter value based on the measurement signal(s) and comparing the parameter value to a threshold value. The assessment may further involve a comparing the parameter value to a predetermined reference value such as a previous measurement of pressure pulses from the same pulse generator, but with a deliberate normal or irregular configuration.

Different techniques for calculating such an evaluation parameter value are further disclosed and exemplified in Appendix B, in which the isolated pressure data is a time-dependent monitoring signal including pressure pulses originating from the relevant physiological phenomenon, and in which the monitoring signal is subjected to a time domain analysis. Thus, all techniques disclosed in Appendix B with respect to the evaluation of heart pulses, including the use of timing information, are equally applicable to other physiological phenomena, such as breathing, autonomic regulation of body temperature, and autonomic regulation of blood pressure, or combinations thereof. In addition to Appendix B, reference is also made to Applicant's International patent publication WO2009/156174, entitled "Methods and Devices for Monitoring the Integrity of a Fluid Connection", which is incorporated herein in its entirety by this reference.

For instance, the timing information from Appendix B may be used to compare arrival of pulses with withdrawal and return devices in normal and reversed configurations respectively, particularly for detection of a reversed configuration.

There are of course other techniques for calculating the evaluation parameter value, including other types of time domain analyses, as well as different types of frequency domain analyses, e.g. as indicated in the following.

Other factors, such as the medical history of the patient, e.g. heart status, blood pressure and heart rate may also be utilized for improving the performance of the detection and monitoring of the configuration of the withdrawal and return devices.

There are many different markers or measurements of a pulse which may indicate the relative location of access devices, such as pulse amplitude, local maximum, local average, shape/contour.

Pressure data extracted from the measurement signal may be represented as a temporal pulse profile in the time domain. The temporal pulse profile may be transformed into a frequency spectrum and a phase spectrum, or only a frequency spectrum and thus loosing the timing information. From the pressure data, a parameter value may be calculated. The parameter value may be related to the amplitude, shape or timing of the pressure pulse.

Figure 10A:
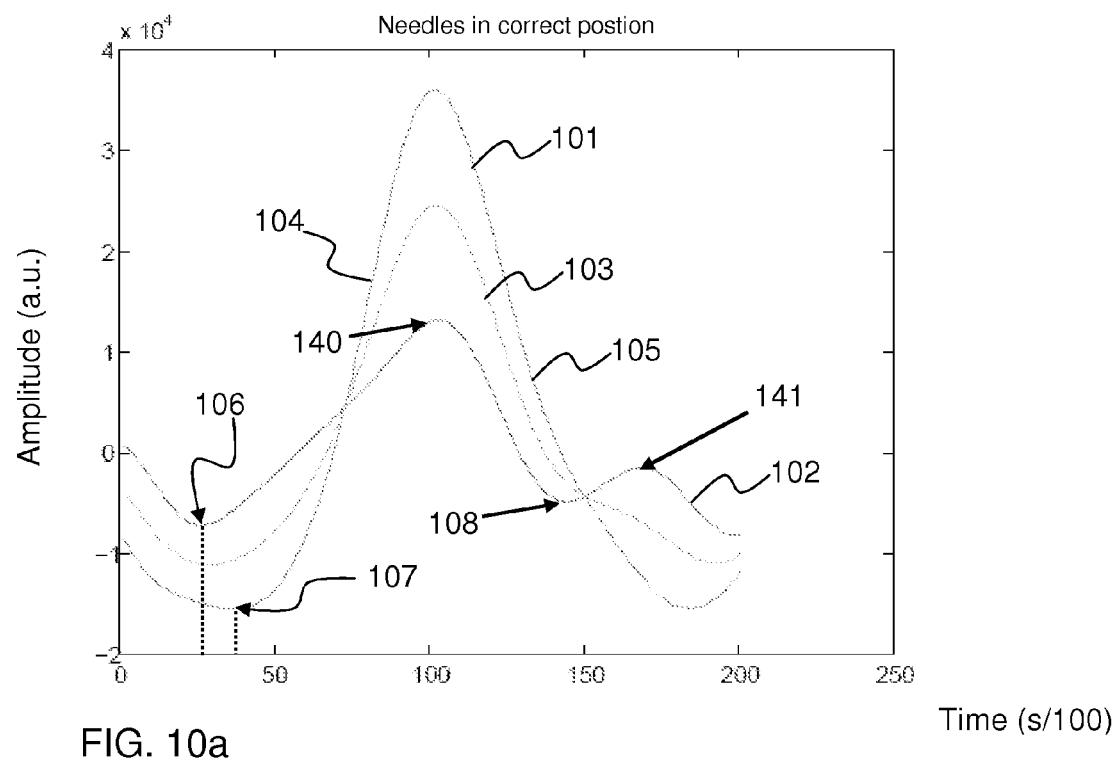
FIG. 10(a) is a plot in the time domain of venous and arterial pressure signal segments with the withdrawal and return devices in a normal configuration.
Figure 10B:
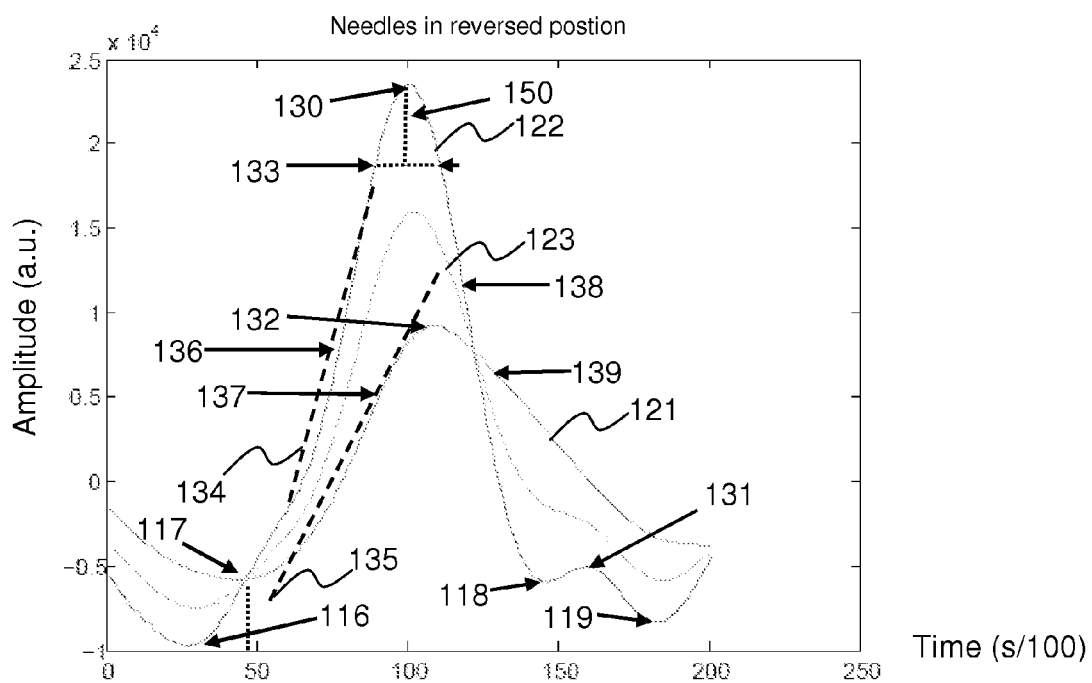
FIG. 10(b) is a plot of the corresponding venous and arterial pressure signal segments in a reverse configuration.

FIG. 10 a) and b) show signal segments of the heart pulse in the arterial and venous lines. 101 and 121 represents the arterial signal in a a) normal and b) reversed configuration respectively. Other pulse sources such as the blood pump have been removed. The duration of each signal segment is two seconds. Also shown is an average of the signals 103 and 123 respectively. FIG. 10(a) shows the signals with the needles in a normal configuration (also denoted "correct positions"), and FIG. 10(b) shows the signals with the needles in a reverse configuration (also denoted "incorrect positions" or "backward positions"). Various measures may be extracted and compared to thresholds in determining the configuration.

Detection by Amplitude

The needle that is positioned closest to the upstream anastomosis is expected to pick up the strongest heart pressure signal. Normally, the amplitude of the heart pulse is larger in the arterial pressure than in venous pressure when the needles are inserted in correct positions with the arterial needle closest to the upstream anastomosis. This may be explained by the pressure drop between the needles due to the access blood flow and the flow resistance of the fistula/graft. In addition, the compliance of the blood line components e.g. the venous drip chamber cause the venous signal to be attenuated to a larger degree than the arterial signal. Therefore, a reverse needle configuration may be detected if e.g. the amplitude or integral of amplitudes of the heart pulse in the venous pressure is larger than in the arterial pressure, or if the relationship between them is outside a specific range, which could be generic or personalized.

This is for instance illustrated in section b) of FIG. 10 with needles in reverse configuration. For instance, a local maximum 130 of the heart signal of the venous needle pressure 122 is greater than a local maximum 132 of the heart signal of the arterial needle pressure 121 may indicate a reverse configuration. The quotient between two local maxima 130 and 131 of the venous component exceeding a threshold may also be an indicator of reverse configuration, e.g. the quotient of the reversed configuration indicated with reference numbers 131/130 is less than the quotient of the normal configuration 141/140. Alternatively, the detection may be performed in the frequency domain by analysis of the amplitude and/or phase spectrum.

To illustrate the principles of detection by amplitude, examples with the R=Hv/Ha ratio measure from simulations performed based on a model explained in a separate section will be shown and discussed briefly in the following. Although the examples show a ratio measure, other amplitude measures may be used, such as Hv or Ha alone.

Figure 12:
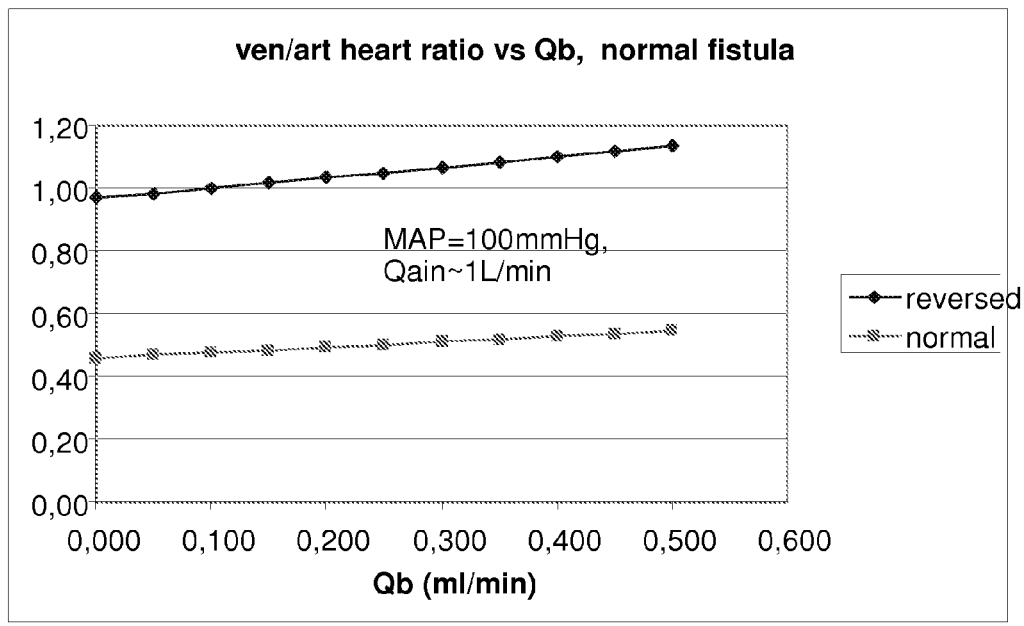
FIG. 12 is a plot of a venous/arterial heart signal amplitude ratio of a normal fistula with the needles in reversed and normal positions compared to the blood flow.

FIG. 12 shows a venous/arterial heart ratio compared to blood flow with a normal fistula at constant mean arterial pressure (MAP). It is seen that the ratio $R_R$ in the reversed configuration is greater than the ratio $R_N$ in the normal configuration.

Figure 13:
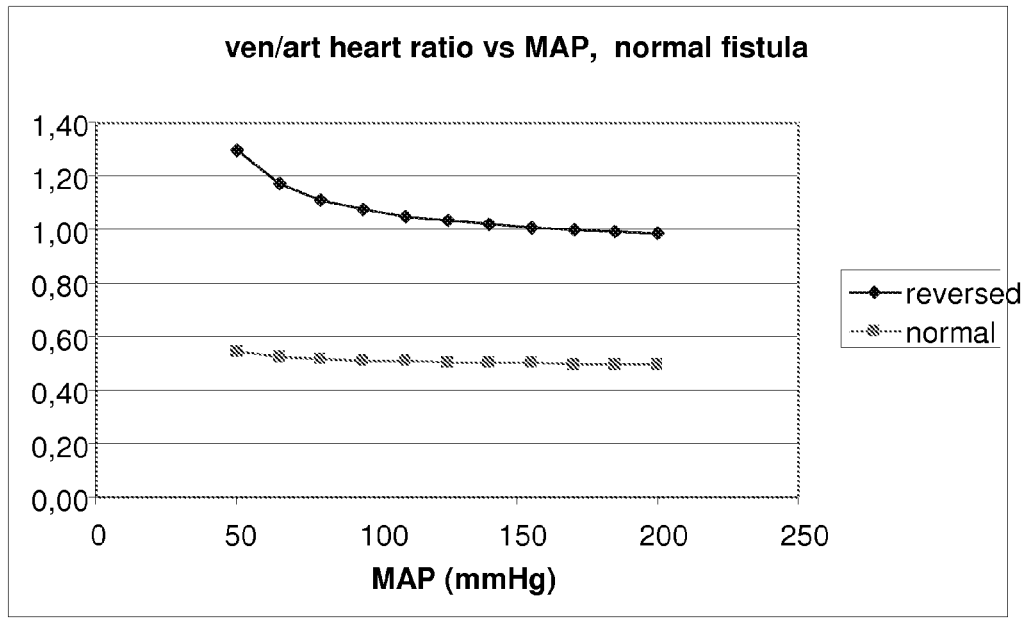
FIG. 13 is a plot of a venous/arterial heart ratio of a normal fistula with the needles in reversed and normal positions compared to the dialysis monitor blood flow Qb in a normal fistula.

FIG. 13 shows a venous/arterial heart ratio compared to the mean arterial pressure (MAP) with a normal fistula. It is again seen that the ratio $R_R$ in the reversed configuration is greater than the ratio $R_N$ in the normal configuration also in varying blood flow Qb.

Figure 14:
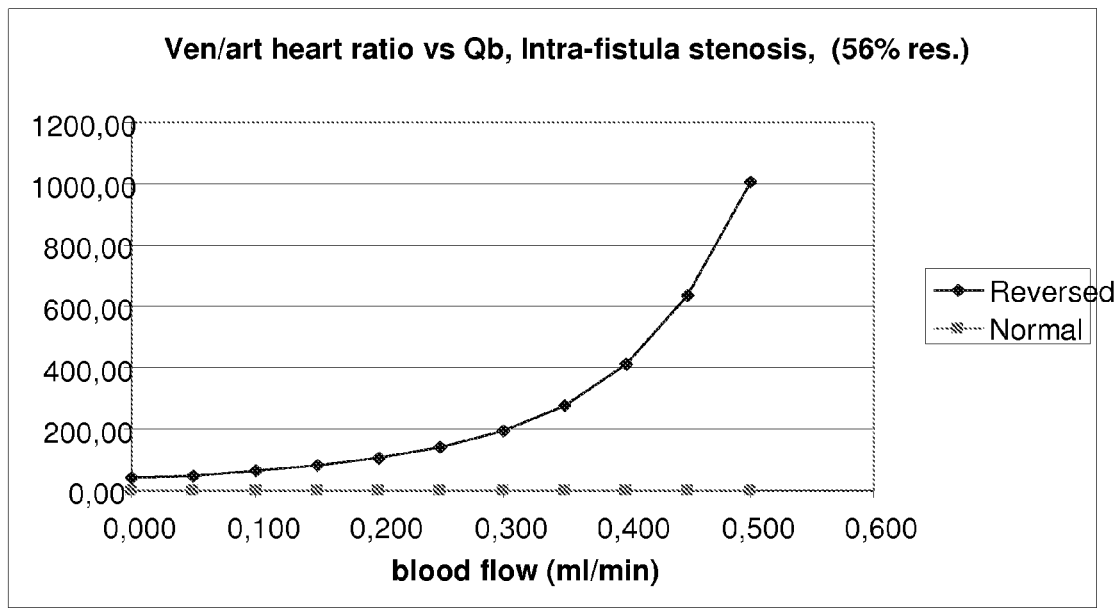
FIG. 14 is a plot of a venous/arterial heart ratio compared to the dialysis monitor blood flow Qb in a fistula having intra-fistula stenosis FIG. 15, as presented in Appendix A, is a schematic view of a general fluid containing system in which the inventive data processing may be used for filtering a pressure signal.

FIG. 14 shows a venous/arterial heart ratio compared to the dialysis monitor blood flow Qb in a fistula having intra-fistula stenosis, i.e. stenosis between the access sites. It is seen an extreme difference between the ratio $R_R$ in the reversed configuration is greater than the ratio $R_N$ in the normal configuration.

Detection by Phase

Generally, a normal configuration of the needles is recognized in that the heart pulse arrives to the arterial needle before it arrives to the venous needle. Analogous to the cardiovascular system, it is assumed that the pressure pulse velocity is higher in a pressurized tube than in an evacuated tube. This may cause a delay of the heart pulse in the arterial line compared to the venous line. Since the average arterial pressure is lower than the venous pressure, the difference in arrival time of the sensor will show up as a phase difference. The phase difference will change in the reverse configuration since the arterial pressure in this case is even lower and the venous pressure is higher in this configuration. So, if the phase difference is larger than a threshold, the reverse configuration may be detected. In FIG. 10(a) for instance, the arterial signal 101 is greater in amplitude but is lagging a bit compared to the venous signal 102, which is seen in that the venous signal 102 has its lowest point 106 at around 0.3 seconds and where the arterial signal has its lowest point 107 at around 0.4 seconds. In FIG. 10(b) on the other hand, the arterial signal 121 is smaller and is lagging much compared to the venous signal 122 which has its lowest point 116 at around 0.3 seconds and the arterial signal 121 has its lowest point 117 at around 0.5 seconds.

The detection may also be performed in the frequency domain by analysis of the amplitude and/or phase spectrum.

Detection by Shape

Damping and delay of the frequency components of the heart pulses affecting their shape depend the on the compliance of the fluid system. The compliance is a function of the actual pressure, flows and the physical properties of the system comprising fistula and extra-corporeal circuit. In a blood vessel with normal elasticity and/or exposed to moderate pressures, the heart pulse may present a more complex shape such as with a greater number of troughs and/or peaks, whereas the heart pulse in situations with a stiffer vessel and/or exposed to higher pressures may present a less complex shape with fewer troughs/peaks. The venous and arterial pressures and the blood flow between the needles in the fistula change with the arrangement of the needles. Therefore the shape of the heart pulses may be different in the reverse configuration compared to the normal configuration of the needles and may be used for detection of the reverse configuration. In the following, a few examples denoted i)-iv) will be described. A first example of an indicator may be i) the accentuation of bi- and tri-phases in the pulse. For instance, as seen in FIG. 10a) representing a normal configuration, the venous signal 102 exhibits an anacrotic or "bi-phasic" shape determined by the troughs 106 and 108. However, in FIG. 10b), the venous signal 122 exhibits an catacrotic or "triphasic" shape determined by the troughs 116, 118 and 119. A second indicator example may be ii) comparison of the shape of a temporal pulse profile with a reference pulse, for instance by cross-correlating the measured pulse with a reference pulse for identifying a best match with a reference pulse representing normal or reverse configuration. In particular, the reference pulse may have been derived from a subject's individual pulse characteristics for a normal and a reverse configuration respectively. A third indicator example is a iii) comparison with another measurement, for instance the venous pulse compared to the arterial pulse. Alternatively, in a fourth indicator example, iv) the venous or arterial pulse may be compared to a measurement of the venous or arterial pulse by an independent sensor. According to fifth indicator example, v) the width 133 of a component at a predetermined distance from a local maximum exceeding a threshold may be a further indicator of reverse configuration. Other indicator examples may involve vi) the slope, or rate of change, 134 and 135 of the pressure pulse may also be an indicator of the configuration. The slope may be measured on the leading edge 136, 137 or the trailing edge 138, 139. In the frequency domain, the corresponding frequency and phase spectra, which represent shape, may be compared with reference data.

The parameter value may further comprise a quotient between amplitudes of a first and a second local maxima in the pulse.

The parameter value may comprise a rate of change of the amplitude on a first side, second side or both sides of a local maximum in the pulse, for instance the raise and/or fall time or slope of the pulse. Alternatively, the rate of decrease in amplitude from an amplitude maximum may be cross-correlated with an exponential function $e^{-kt}$ by varying a factor k of exponential change.

The parameter value may further comprise the width 133 of the pulse at a predetermined distance 150 from a local maximum in the pulse.

The temporal pulse profile may also be compared to a reference pulse profile on a more general basis, such as matching profiles by cross-correlation of the signal profiles. A match between a measured temporal pulse profile with a reference temporal pulse profile representative of a normal or reversed configuration may thus be indicated by a cross-correlation value exceeding a predetermined threshold. Comparison with different reference temporal pulse profiles may be advantageous where the representation of normal or reversed configurations may vary. Additionally, references pulse profiles may be compensated for distances between needles, mean arterial pressure, access flow Qb etc.

The parameter value may further comprise a quotient between a relative time difference between the artery and vein signal components in a normal versus a reversed position.

Artery and vein arrival times may also be visible as a phase shift in the phase spectrum of the frequency domain.

All measures or relation/ratio of these, i.e. magnitude, shape, phase etc, of the heart, breathing or other pulse signals in the venous and/or arterial pressures may also be compared to previous corresponding data and utilized for detection of reversed positioning of detection devices. For instance, if for a particular subject, the breathing signal based on arterial pressure normally is larger than breathing based on the venous signal, but the opposite relation appears during a treatment, it may be an indication of accidental access misplacement or faulty connection such as misplaced needles or reversed connections of needles or catheters to the blood lines.

Detection by Pump Signal Analysis.

The pump pressure profiles in the venous line and in the arterial line may differ if the needles are reversed than in normal position. Detection may be carried out analogous to the previous cases.

The detection process may operate on the pressure signal(s) obtained from one or more of the pressure sensors in the extracorporeal circuit, optionally after pre-processing.

However, it may be advantageous to operate the detection process on isolated pressure data which is extracted from the pressure signal(s). For example, the isolated pressure data may be obtained by proper filtering, which suppresses/removes the physiological pulses from the pressure signal(s) while retaining at least part of pressure pulses originating from a pulse generator in the extracorporeal system, or in the dialysis machine (i.e. the pressure pulses that have been denoted "pressure artefacts" in the foregoing). The filtering may involve one or more of the filtering techniques described in Section VI below, and in particular the techniques disclosed under "Isolating pressure data from a physiological phenomenon", albeit adapted to isolate the pressure artefacts instead of the pulses from a physiological phenomenon). The skilled person should have no difficulty adapting the techniques in that chapter to achieve the desired filtering. With respect to time domain filtering, it should be noted that the techniques of Appendix A are applicable. Thus, although Appendix A is concerned with eliminating pressure pulses originating from a pulse generator in an extracorporeal circuit, such as a pumping device, it is equally applicable for eliminating pressure pulses originating from unwanted physiological phenomena. For example, an adaptive filter may be fed with a reconstructed pressure profile originating from all of the physiological phenomena to be removed, and the signal of interest may be extracted as an error signal of the adaptive filter. Alternatively, the adaptive filter may be fed with a reconstructed pressure profile of the pressure artefacts, and the signal of interest may be extracted as an estimated measurement signal of the adaptive filter. In addition to Appendix A, reference is also made to Applicant's PCT publication WO2009/156175, entitled "Method and device for processing a time-dependent measurement signal", which is incorporated herein in its entirety by this reference.

A particular embodiment relates to a cross-talk effect that may be detected in one of the pressure sensors in the extracorporeal circuit. When for instance a blood pump is running, its generated pressure pulses are transported in two directions from the pump along the extracorporeal circuit. A pressure sensor may then obtain the pressure pulses from two directions, i.e. a first set of pressure pulses which have been transported through the extracorporeal circuit only and a second set of pressure pulses having been transported through the cardiovascular system on its way.

Detection by Timing Information

According to an embodiment of the present invention, detection of a reversed configuration may be detected by analysing the transit time of heart pulse waves to the pressure sensors, which differs since the pressure sensors are located at different distances from the heart and the length of blood lines interconnecting the heart and pressure sensors are different. Hence, a deviation in transit time from expected values associated with a normal configuration would represent a reversed configuration. For instance, in a reversed configuration, the heart pulse wave would arrive earlier to the venous pressure transducer and later to the arterial pressure transducer. The difference of the arrival times, i.e. between the arterial pressure transducer and the venous pressure transducer would be greater, it would be approximately twice the distance between needle access sites divided by the heart wave velocity greater in a reversed position. According to an example, assuming a distance of between the access devices and a pulse propagation speed of 10 m/s, we have 0.1 m*2/(10 m/s), which is approximately 20 ms.

VI. SIGNAL EXTRACTION OF PHYSIOLOGICAL PULSE

In the following, embodiments for eliminating or reducing various pressure artefacts (also denoted "pump pulses" or "interference pulses") originating from one or more pulse generators in or associated with extracorporeal circuit will be described. Then, embodiments for isolating pressure data originating from a relevant physiological phenomenon among pressure pulses or pressure modulations originating from other physiological phenomena are described.

The pressure data to be extracted is not limited to a single physiological phenomenon and may originate from one or more physiological phenomena, including the heart. As used herein, the pressure data to be isolated is also denoted "subject pulses" or "patient pulses".

Elimination of Artefacts

Elimination of artefacts may be provided by:
  Controlling a pulse generator in the extracorporeal blood flow circuit, such as a pump
    By temporarily shutting down the pulse generator;
    Shifting the frequency of the pulse generator;
  Low pass, band pass or high pass filtering;
  Spectral analysis and filtering in the frequency domain;
  Time domain filtering.

Controlling a Pulse Generator

Artefacts from a pulse generator, such as a pump, in the extracorporeal fluid circuit may be avoided by temporarily shutting down (disabling) the pulse generator, or by shifting the frequency of the pulse generator away from frequencies of one or more relevant physiological phenomena.

A feedback control with respect to the heart rate, e.g. obtained from a dedicated pulse sensor attached to the patient or obtained via analysis of previous parts of the monitoring signal, may be used to set the pump frequency optimally for detection of heart pulses. Similar feedback control may be used to eliminate artefacts with respect to pressure pulses originating from breathing, e.g. based on a breathing signal from an independent source, such as a capnograph instrument. Hence, the control unit 23 of FIG. 1 may be operated to control the pump frequency in order to facilitate the detection of the subject pulses, e.g. the pump frequency is controlled to minimize any overlap in frequency between the pump pulses and the subject pulses. For example, the pump frequency may be periodically increased and decreased around the overlap frequency, so as to maintain the overall blood flow rate. In a variant, the pump frequency is instead controlled so as to synchronize the rate of pump pulses with the rate of subject pulses while applying a phase difference between the pump pulses and the subject pulses. Thereby, the pump pulses and the subject pulses will be separated in time, and the subject pulses may be detected in the time domain, even without removal of the pump pulses. The phase difference may be approximately 180°, since this may maximize the separation of the pump pulses and the subject pulses in the time domain. This so-called phase-locking technique may be activated when it is detected that the rate of subject pulses approaches the rate of pump pulses, or vice versa.

Applying Low Pass, Band Pass or High Pass Filters

The input signal to step 903 (FIG. 9) may be fed into a filter, e.g. digital or analogue, with frequency characteristics, such as frequency range and/or centre of frequency range, matched to the frequencies generated by a pulse generator, such as a pump, in the extracorporeal circuit. For instance, in a case where the pulse generator, such as a pump, operates within the frequency range of 1 Hz, a suitable low pass filter may be applied in order to remove pressure artefacts above 1 Hz while retaining frequency components of the physiological phenomenon below 1 Hz. Correspondingly, a high pass filter may be applied to retain frequency components above the frequency of the pulse generator. Alternatively, one or more notch filters or the like may be utilised to remove/attenuate frequencies in one or more confined ranges.

Spectral Analysis and Filtering in the Frequency Domain;

The input signal to part 133 may be subjected to a spectral analysis, e.g. by applying a Fourier transformation technique, such as FFT (Fast Fourier Transform) to convert the input signal into the frequency domain. The resulting energy spectrum (amplitude spectrum) may then be multiplied by an appropriate filter function and then re-transformed into the time domain. There are many alternative and equivalent filtering techniques available to the skilled person. The Fourier transformation technique may also be used for tailoring/adjusting filters used for eliminating artefacts.

Time Domain Filtering

Artefact elimination by filtering in the time domain is further disclosed and exemplified in Appendix A. In the context of Appendix A, the input signal to step 903 (FIG. 9) is denoted "measurement signal", and the resulting "filtered signal e(n)" corresponds to, or may be processed for extraction of, the monitoring signal. In addition to Appendix A, reference is also made to Applicant's International patent publication WO2009/156175, entitled "Method and device for processing a time-dependent measurement signal", which is incorporated herein in its entirety by this reference.

Isolating Pressure Data from a Physiological Phenomenon

Isolating pressure data originating from a relevant physiological phenomenon may be provided by any or a combination of:
  Low pass, band pass or high pass filtering;
  Spectral analysis and filtering in the frequency domain; or
  Time domain filtering.

Applying Low Pass, Band Pass or High Pass Filters

The input signal to step 905 may be fed into a filter, e.g. digital or analogue, with frequency characteristics, such as frequency range and/or centre of frequency range, matched to the frequencies of pressure pulses from a relevant physiological phenomenon where e.g. in case the isolation concerns:
  Heart pulses, a frequency range substantially of 0.5-4 Hz will be allowed to pass the filter;
  Breathing, a frequency range substantially of 0.15-0.4 Hz will be allowed to pass the filter;
  Blood pressure regulation due to the autonomous system, a frequency range substantially of 0.04-0.15 Hz will be allowed to pass the filter; and
  Temperature regulation due to the autonomous system, a frequency range substantially of 0.001-0.1 Hz will be allowed to pass the filter.

Spectral Analysis and Filtering in the Frequency Domain

The input signal to step 905 may be subjected to a spectral analysis, e.g. by applying a Fourier transformation technique, such as FFT (Fast Fourier Transform) to convert the input signal into the frequency domain. The resulting energy spectrum (amplitude spectrum) may then be multiplied by an appropriate filter function and then re-transformed into the time domain. There are many alternative and equivalent filtering techniques available to the skilled person.

Time Domain Filtering

The signal of interest may be extracted from the input signal to step 905 as an error signal of an adaptive filter. The adaptive filter is fed with both the measured pressure signal and a predicted signal profile of a cyclic disturbance. The cyclic disturbance may be any of the other physiological signals (e.g. heart pulsation or breathing). Particularly, a reconstructed pressure profile originating from the unwanted physiological phenomenon may be input to the adaptive filter. This and other time domain filtering techniques for removing unwanted signal components from a measurement signal is further disclosed and exemplified in Appendix A. Although Appendix A is concerned with eliminating first pulses originating from a pulse generator in an extracorporeal circuit, such as a pumping device, it is equally applicable for eliminating first pulses originating from unwanted physiological phenomena, as long as a predicted signal profile of the first pulses may be obtained. The skilled person realizes that such a predicted signal profile may be obtained in any of the ways described in Appendix A. In addition to Appendix A, reference is also made to aforesaid WO2009/156175.

Some of the filtering techniques described above may automatically be achieved by down-sampling, since it may be taken care of by the anti-aliasing filter included in a down-sampling signal processing algorithm. Additionally, some of the above described filtering techniques may also be achieved directly in hardware, e.g., in the Analogue-to-Digital conversion by choosing an appropriate sample frequency, i.e. due to the anti-aliasing filter which is applied before sampling.

VII. MODELLING OF A FISTULA

For a better understanding of the inventive concept, modelling of an exemplary fistula of FIG. 2 will be described in the following. Other fistula configurations may be modelled according to the same principles, although requiring adjustments to the actual configuration.

Figure 11:
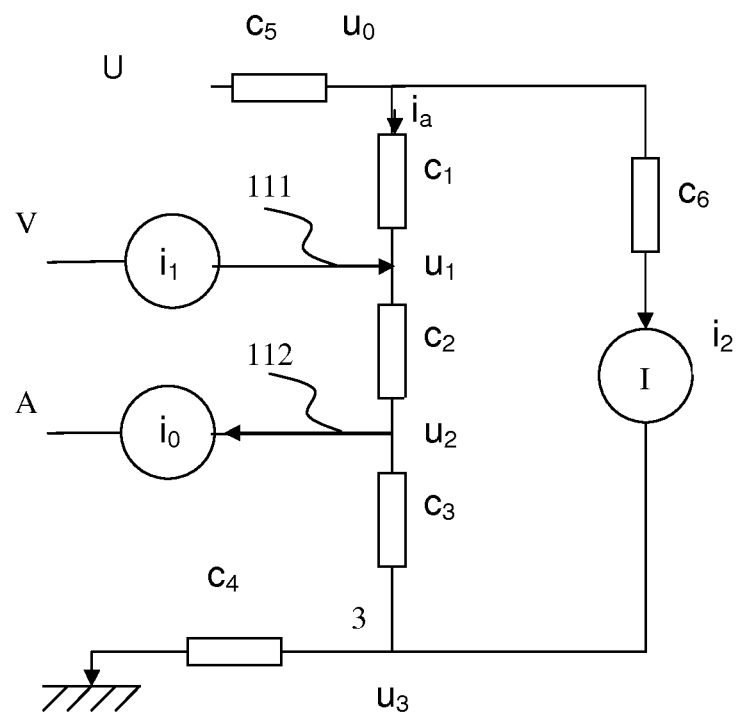
FIG. 11 is a block diagram of a hydraulic model to simulate the characteristics in normal and reversed configurations according to the present invention.

The fistula configuration may be translated into a hydraulic model as is shown in FIG. 11, where the blood flow in the access devices (111, 112) are in a reversed configuration, i.e. with blood withdrawal 112 at venous access site and blood return 111 at arterial access site. U represents a systemic blood pressure such as the mean arterial pressure MAP or a pressure pulse close to the heart. Table 1 below lists the parameter definitions that are used in FIG. 11.

Since the model is dynamic, it may be applied to pressure levels as well as pressure variations.

TABLE 1

Parameter definitions

UFR: ultrafiltration rate (i.e. fluid removal rate)
$Q_b$: blood flow of dialysis machine
$c_1$: flow admittance between anastomosis and first access point, 'pre-fistula admittance'
$c_2$: flow admittance between first and second access points, 'intra-fistula admittance'
$c_3$: flow admittance between second access point and common venous return vessel, 'post-fistula admittance
$c_4$: flow admittance in vein between common venous return vessel and venous return to heart
$c_5$: flow admittance in artery entering the fistula
$c_6$: flow admittance in vessels to hand
$u_0$: arterial blood pressure, e.g. mean arterial pressure (MAP)
Reversed position of access needles:
u1: blood pressure at access point 1
u2: blood pressure at access point 2
u3: blood pressure at common venous return vessel
Normal position of access needles:
u'1: blood pressure at access point 1
u'2: blood pressure at access point 2
u'3: blood pressure at common venous return vessel
$i_0$: blood flow pumped out of the fistula, $Q_b$
$i_i$: blood flow pumped back to the fistula: $Q_b$-UFR
$i_2$: arterial blood flow required by the tissues downstream of the fistula,
$i_a$: blood access flow entering the fistula
Ha: heart pressure amplitude at "A" in fig 11, i.e. at arterial pressure transducer
Han: Ha when normal needle position
Har: Ha when reversed needle position
Hv: heart pressure amplitude at "V" in fig 11, i.e. at venous pressure transducer
Hvn: Hv when normal needle position
Hvr: Hv when reversed needle position
R: Ven/Art heart amplitude ratio, i.e. R = Hv/Ha,
Rn: Hvn/Han
Rr: Hvr/Har
Rrhist: "average of Rr over a number of previous treatments"
Rrmod: "detection limit for R in reversed position that is based on modelling"

In the model, it has been assumed that the blood pressure of the artery e.g. mean arterial pressure MAP is controlled to a constant value ($u_0$), the demand of nutrition and oxygen of tissue, the fistula arm is constant ($i_2$) and that all flow admittances ($c_1$-$c_4$) do not vary. Moreover, it is assumed that in a normal fistula configuration the pre-fistula admittance ($c_1$) is less than the post-fistula admittance ($c_3$) which, in turn, is less than the intra-fistula admittance ($c_2$). Both $c_5$ and $c_6$ are omitted in the modelling, since they are assumed to be very large. Moreover, the magnitude of total fistula flow admittance is chosen as to result in a physiological range of fistula flow.

The sum of the flows entering each of connections 1, 2 and 3 are zero—therefore the following equations can be defined:

$$c_1(u_0-u_1)+i_1+c_2(u_2-u_1)=0 \qquad (1)$$

$$c_2(u_1-u_2)-i_0+c_3(u_3-u_2)=0 \qquad (2)$$

$$c_3(u_2-u_3)+i_2-c_4u_3=0 \qquad (3)$$

$u_1$, $u_2$ and $u_3$ may then be calculated if $u_0$, $i_1$ to $i_2$ and $c_1$ to $c_4$ are known.

With the blood flowing in a direction according to a normal configuration, blood pressures $u_1'$ and $u_2'$ at the first and second access points respectively, may be determined analogously after replacing $i_1$ with $-i_0$ and $i_0$ with $-i_1$ in the equations above.

Several simulations have been performed with the needles in reversed and normal position to illustrate R, Ha and Hv at different settings of blood pressure, blood flow, absolute and relative flow resistances (inverse of conductances). Results from the simulations are shown in FIGS. 12 to 14, explained above under section V.

VIII. SIGNAL PROCESSING

According to one embodiment of the present invention, it relates to a method for automatic detection of needle reversal based on analysis of readings given by one or more pressure sensors integrated in a dialysis monitor. The pressure readings of each pressure sensor form a measurement signal. The measurement signal may comprise pressure data from different pulse generators in the extracorporeal circuit and in the subject. Such pulse generators include the blood pump, the heart and other physiological phenomena in the subject, such as breathing. Before analysis, the measurement signal may be processed to isolate a pressure data from a particular origin, for instance the heart, breathing or a pump in the extracorporeal circuit. Alternatively, the amplitude and/or phase spectra of the composite signal may be analysed. The aforesaid measurement signal comprises continuously detected measurements from the pressure sensor(s), thus representing an inherently time-dependent signal, and the aforesaid pressure data comprises at least a part of a pressure pulse or one or more pressure pulses originating from one or more pulse generators, such as the heart, the breathing system of the subject, one or more pumps or valves in the extracorporeal circuit, etc. Unless otherwise stated, it will in the following be assumed that the heart pulse is used, although the text is also applicable to the use of the breathing pulse or the pump pulse.

The isolation of pressure data from a particular origin may involve filtering. However, in situations where no efficient filtration can be accomplished, for instance where the noise-to-signal ratio is too large, it may be advantageous to control the pump behaviour. Methods of filtering are detailed above in a separate section.

The signal extraction part 903 involves elimination or reduction of pressure artefacts originating from pulse generators in the extracorporeal blood flow circuit and isolation of pressure data originating from a relevant pulse generator. In the context of the present disclosure, "pressure data isolation" 905 denotes a process of generating a time-dependent signal (also denoted monitoring signal herein) which is free or substantially free from pressure modulations caused by any unwanted pressure generator. Such unwanted pressure generators may vary between different applications, but generally include a blood pump and/or breathing signal components. The elimination of signal noise and signal offset, as well as the elimination of pressure artefacts, may be included in algorithms for pressure data isolation. For instance, the measurement signal may be band pass filtered or low pass filtered to isolate a breathing signal, in a way such that signal noise and/or signal offset and/or pressure artefacts are eliminated from the measurement signal. The elimination of pressure artefacts may thus be performed before, after or during the pressure data isolation.

For instance, in situations where harmonics of the pump ($f_0/2$, $f_0$, $2f_0$, $3f_0$, etc) overlap or are near the frequency of the physiological signal, such as the heart or breathing, the rotation speed of the pump may be adjusted so that the frequencies are separated. For instance, where the fundamental frequency of the pump $f_0$ is 1 Hz, the pump may be adjusted to a new frequency of ⅔ Hz, such that the heart frequency operates in the frequency range between the fundamental frequency of the pump and its first harmonic $2f_0$. Alternatively, the rotation speed of the pump may be adjusted to a relative level, such as 25 percent, from the frequency of the heart. Removal of the pump pulses, or vice versa, may then be accomplished easier.

Alternatively, the blood pump may be temporarily stopped to accomplish complete removal of influence caused by the pump. In order to obtain the necessary measurement data, while avoiding blood coagulation, it may be advantageous to stop the pump for at least 30 seconds and maximum five minutes. Longer duration of the stop increases the precision of the determination, which may also be achieved by repeatedly stopping the pump for shorter time periods.

The test for detection of configuration may be activated manually by a nurse or medical technician, although preferably the test is initiated automatically by an algorithm implemented in the dialysis machine, such as during a treatment start-up initiating routine.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

It is to be understood that Appendix A and Appendix B are to be treated as integral parts of the present application. However, reference numerals are defined within the context of each Appendix separately. In the event of conflicting use of terminology between the Appendix A, Appendix B and the main specification, the terminology should be interpreted within the context of Appendix A, Appendix B and the main specification, respectively.

APPENDIX A

Brief Description of the Drawings

Exemplifying embodiments of the invention will now be described in more detail with reference to the accompanying schematic drawings.

Figure 15:
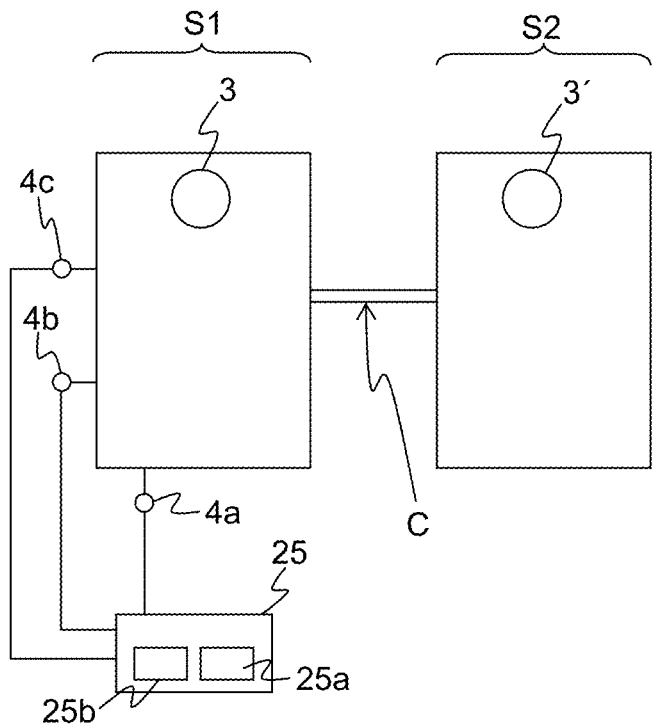

FIG. 15 is a schematic view of a general fluid containing system in which the inventive data processing may be used for filtering a pressure signal.

Figure 16:
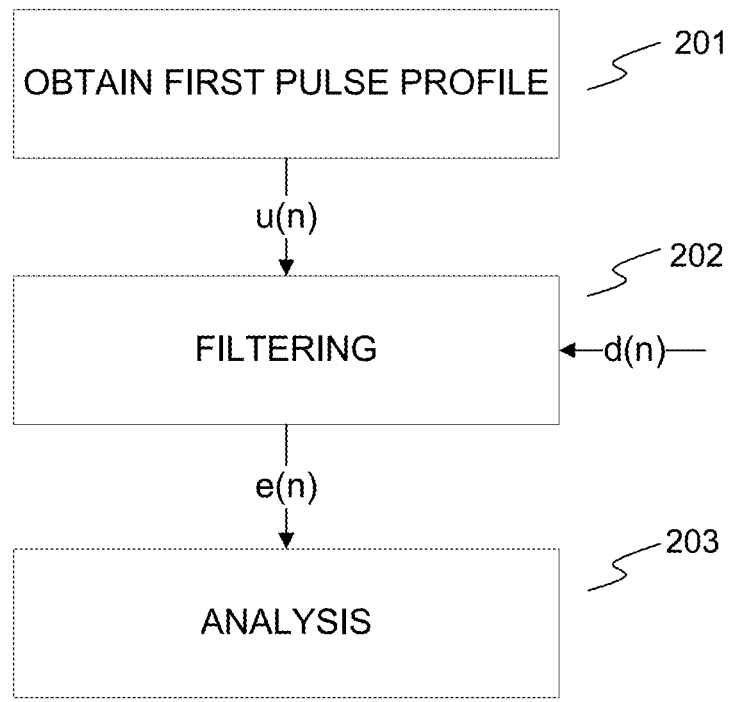
FIG. 16, as presented in Appendix A, is a flow chart of a monitoring process according to an embodiment of the invention.

FIG. 16 is a flow chart of a monitoring process according to an embodiment of the invention.

Figure 17:
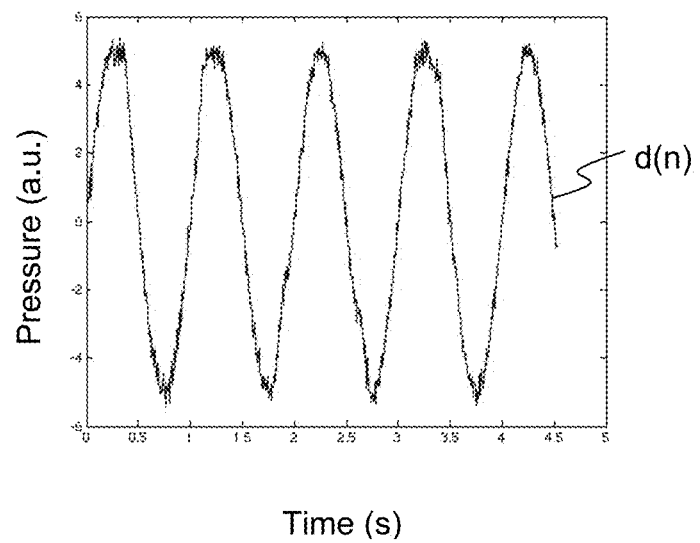
FIG. 17(a), as presented in Appendix A, is a plot of a pressure signal as a function of time, and FIG. 17(b), as presented in Appendix A, is a plot of the pressure signal after filtering.
Figure 17:
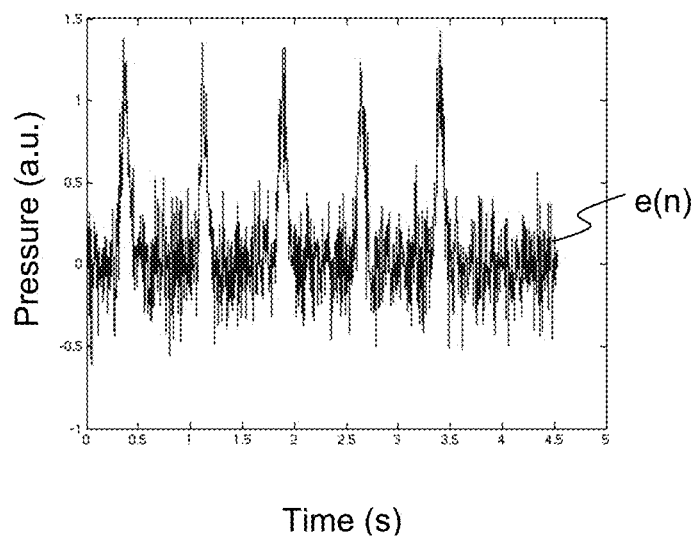

FIG. 17(*a*) is a plot of a pressure signal as a function of time, and FIG. 17(*b*) is a plot of the pressure signal after filtering.

Figure 18:
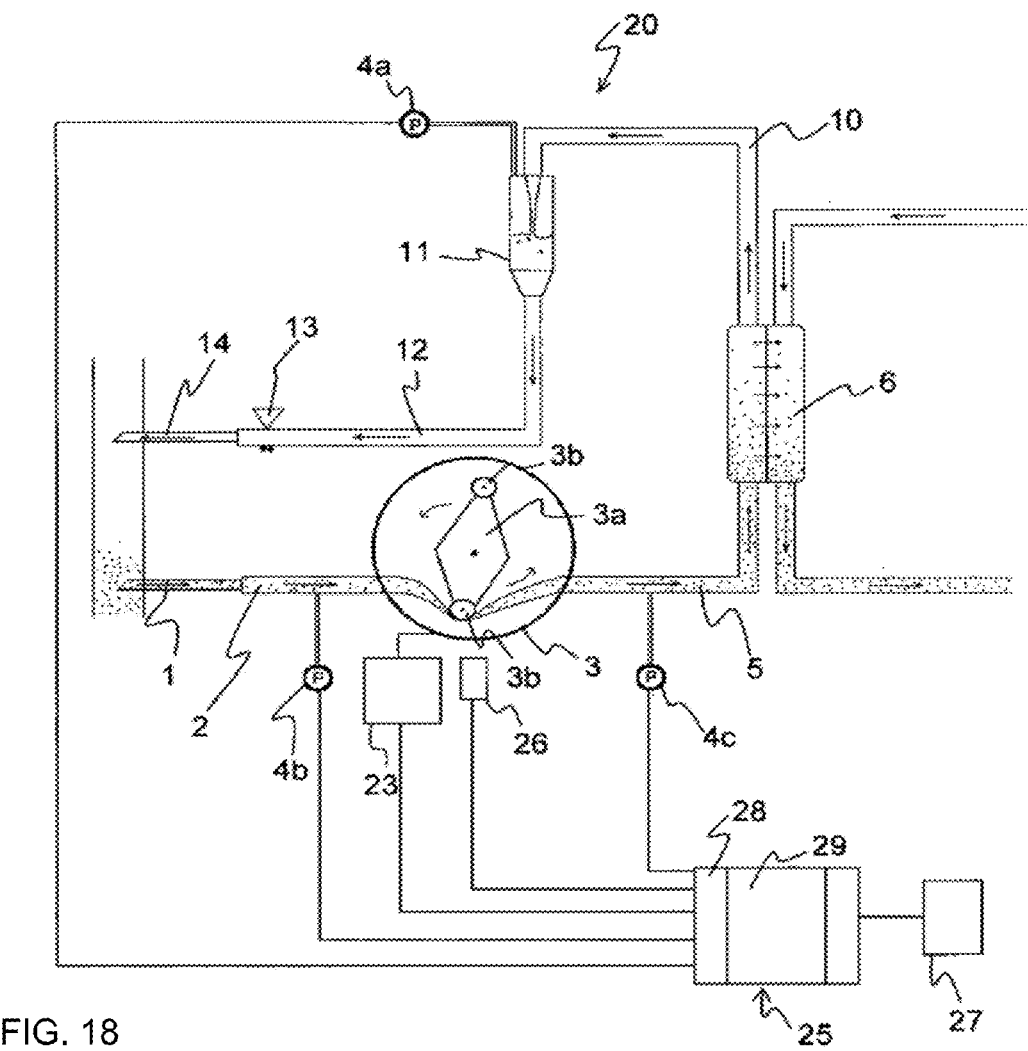
FIG. 18, as presented in Appendix A, is a schematic view of a system for hemodialysis treatment including an extracorporeal blood flow circuit.

FIG. 18 is a schematic view of a system for hemodialysis treatment including an extracorporeal blood flow circuit.

FIG. 19(a) is a plot in the time domain of a venous pressure signal containing both pump frequency components and a heart signal, and FIG. 19(b) is a plot of the corresponding signal in the frequency domain.

Figure 20:
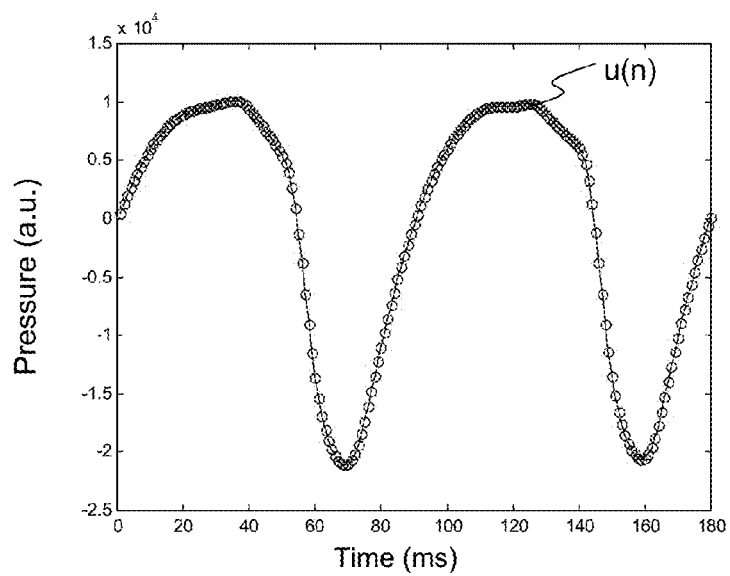
FIG. 20, as presented in Appendix A, is a plot of a predicted signal profile originating from a peristaltic pump in the system of FIG. 18.

FIG. 20 is a plot of a predicted signal profile originating from a peristaltic pump in the system of FIG. 18.

Figure 21:
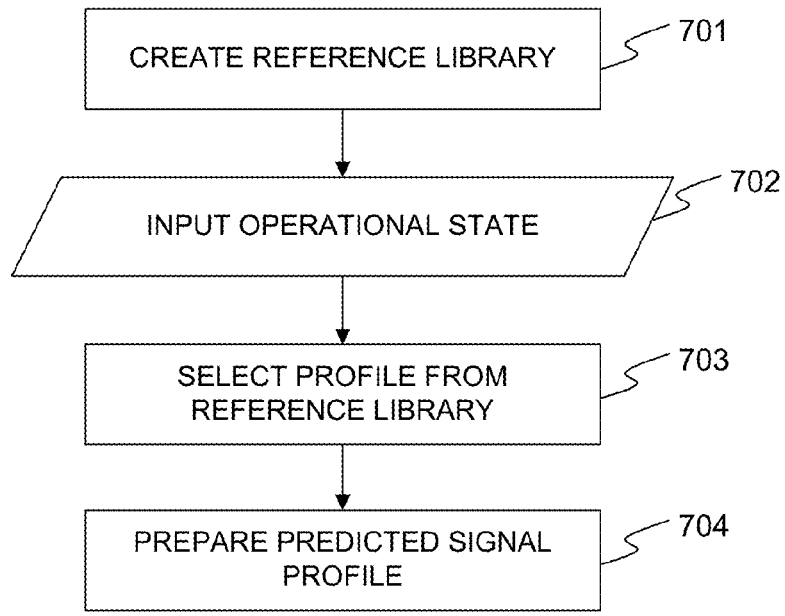
FIG. 21, as presented in Appendix A, is a flow chart of a process for obtaining the predicted signal profile.

FIG. 21 is a flow chart of a process for obtaining the predicted signal profile.

Figure 22:
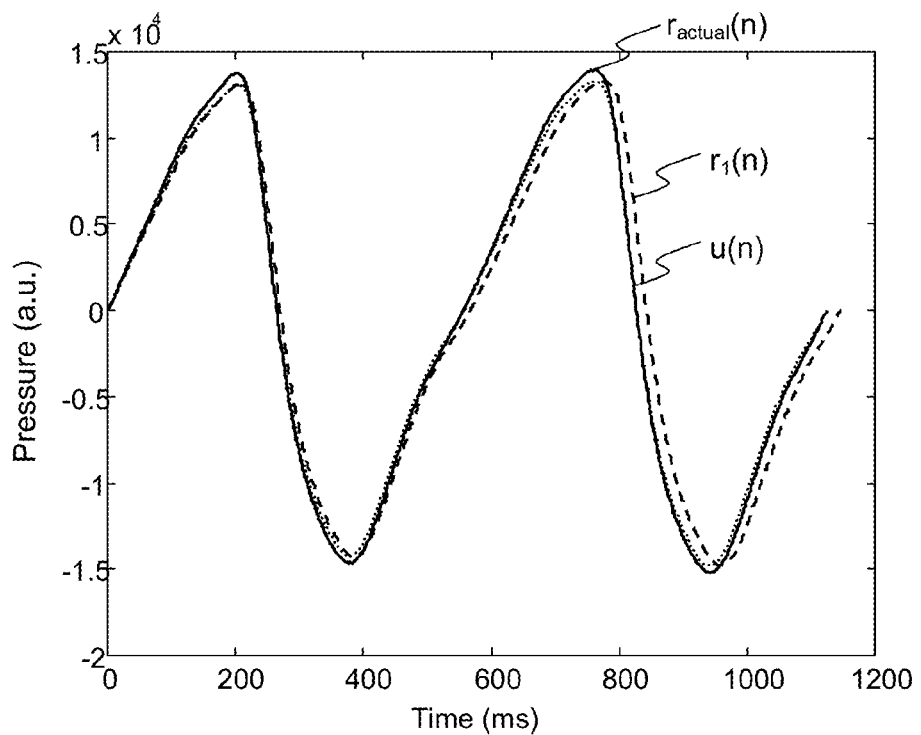
FIG. 22, as presented in Appendix A, is a plot to illustrate an extrapolation process for generating the predicted signal profile.

FIG. 22 is a plot to illustrate an extrapolation process for generating the predicted signal profile.

Figure 23A:
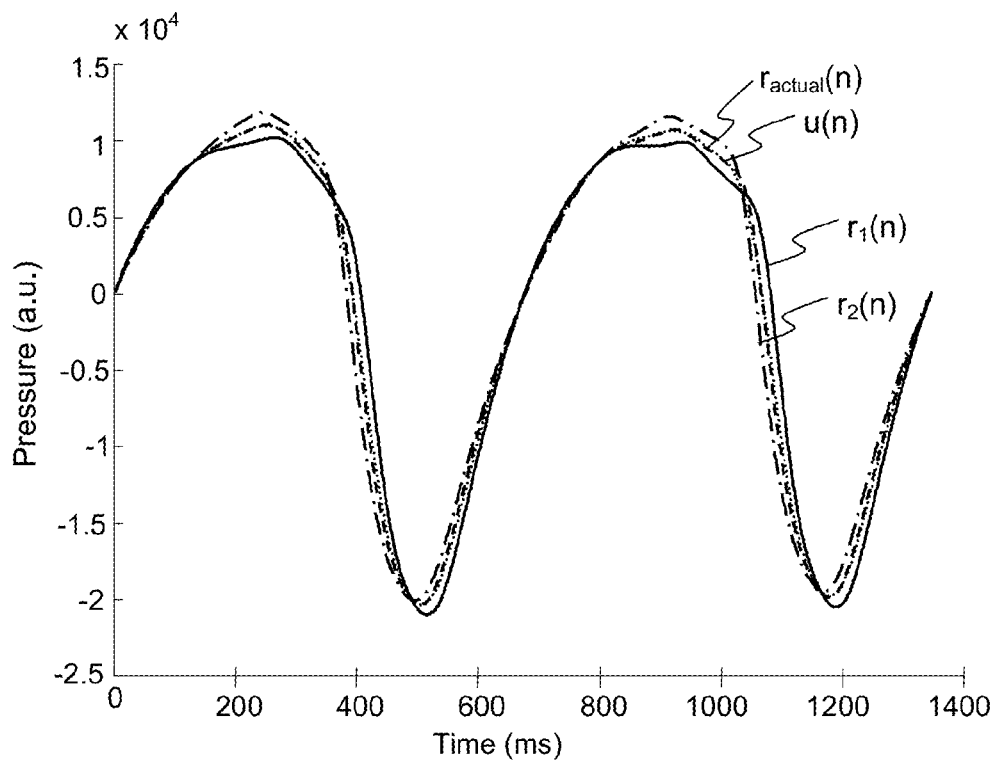
FIG. 23(a), as presented in Appendix A, is a plot to illustrate an interpolation process for generating the predicted signal profile, and FIG. 23(b), as presented in Appendix A, is an enlarged view of FIG. 23(a).
Figure 23B:
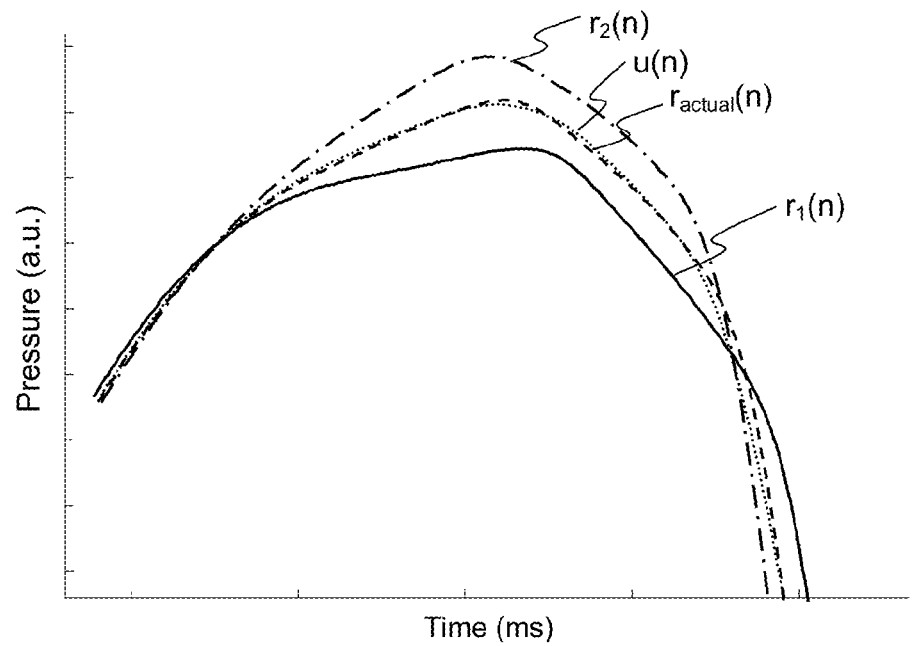

FIG. 23(a) is a plot to illustrate an interpolation process for generating the predicted signal profile, and FIG. 23(b) is an enlarged view of FIG. 23(a).

Figure 24A:
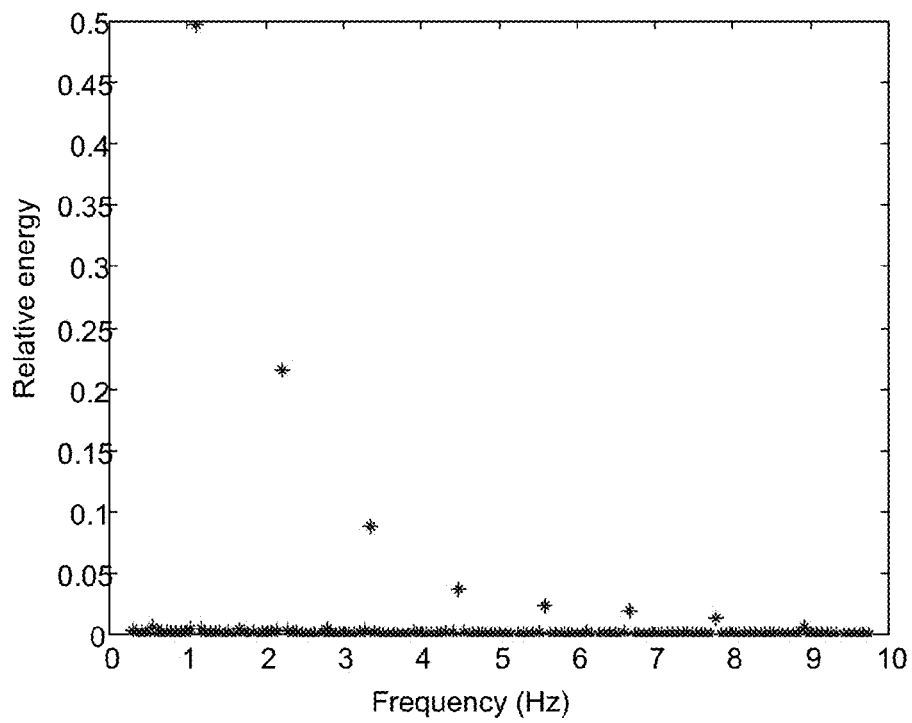
FIG. 24(a), as presented in Appendix A, represents a frequency spectrum of a pressure pulse originating from a pumping device at one flow rate, FIG. 24(b), as presented in Appendix A, represents corresponding frequency spectra for three different flow rates, wherein each frequency spectrum is given in logarithmic scale and mapped to harmonic numbers, FIG. 24(c), as presented in Appendix A, is a plot of the data in FIG. 24(b) in linear scale, and FIG. 24(d), as presented in Appendix A, is a phase angle spectrum corresponding to the frequency spectrum in FIG. 24(a).
Figure 24B:
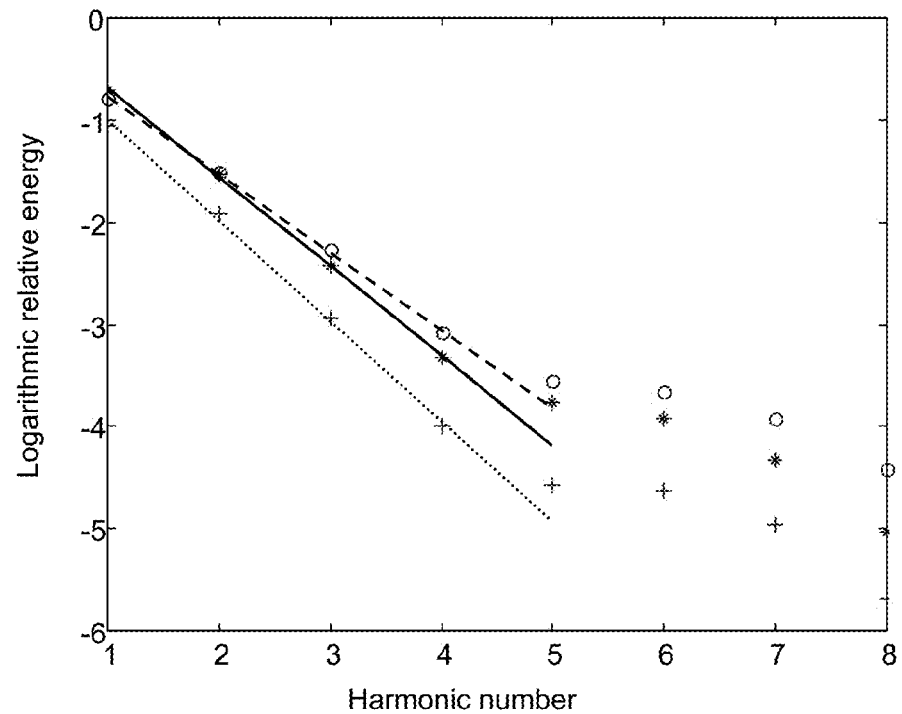
Figure 24C:
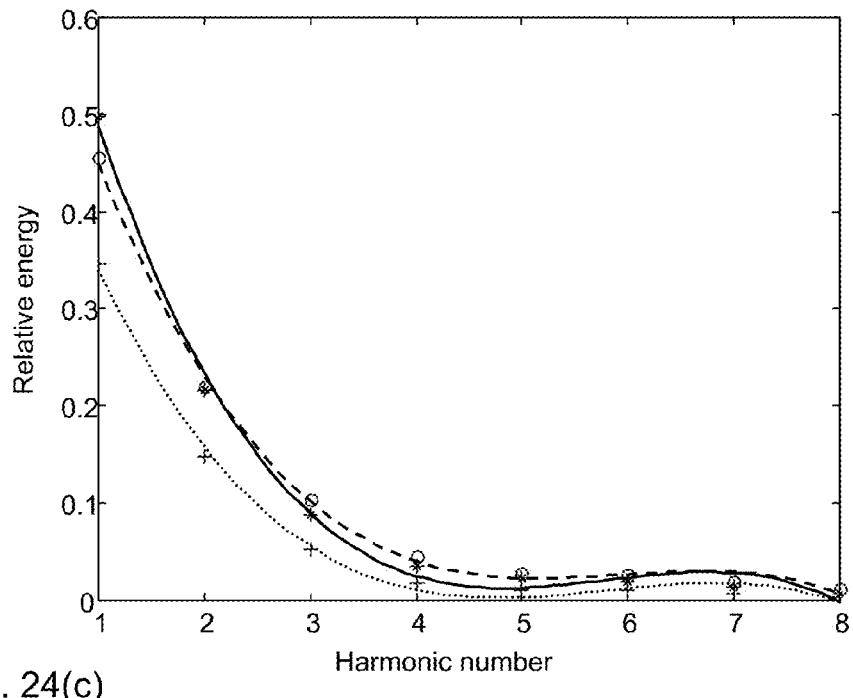
Figure 24D:
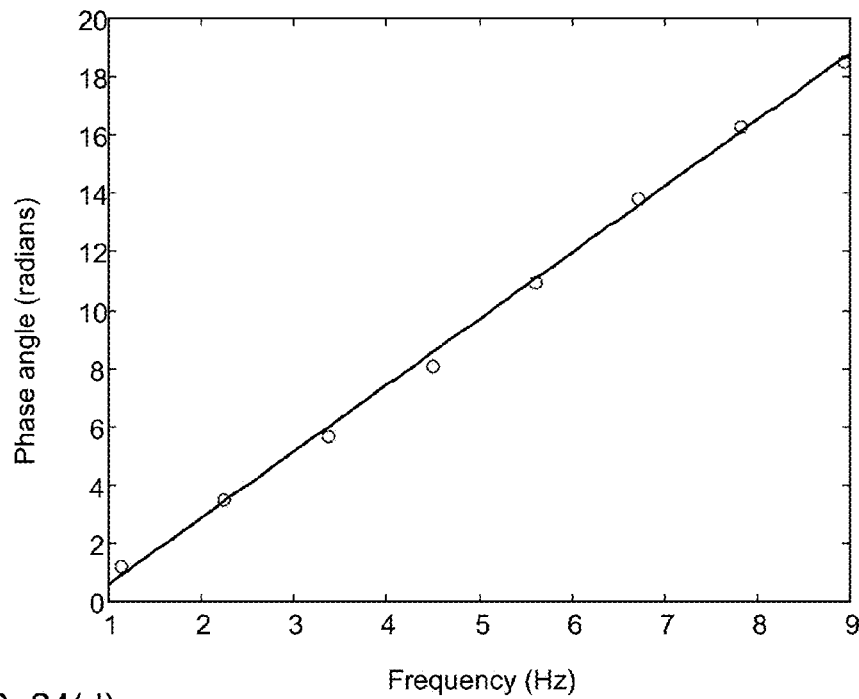

FIG. 24(a) represents a frequency spectrum of a pressure pulse originating from a pumping device at one flow rate, FIG. 24(b) represents corresponding frequency spectra for three different flow rates, wherein each frequency spectrum is given in logarithmic scale and mapped to harmonic numbers, FIG. 24(c) is a plot of the data in FIG. 24(b) in linear scale, and FIG. 24(d) is a phase angle spectrum corresponding to the frequency spectrum in FIG. 24(a).

Figure 25:
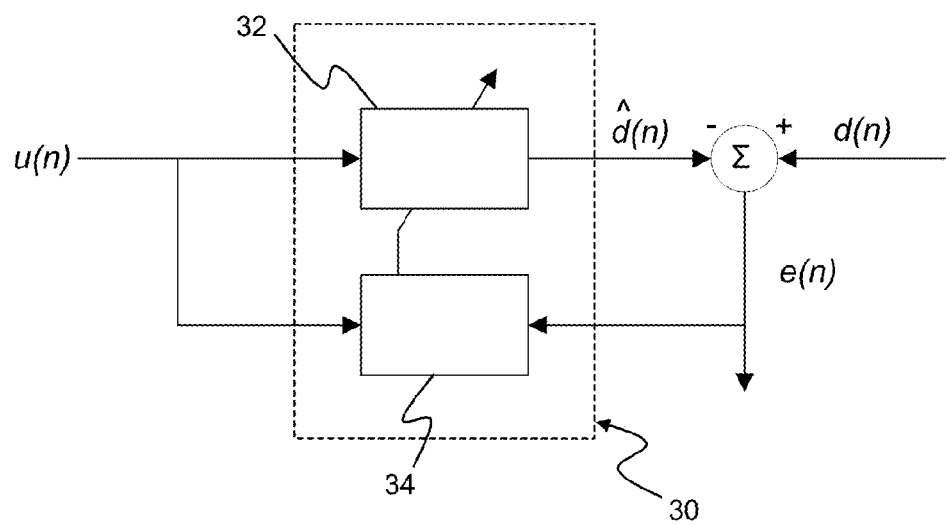
FIG. 25, as presented in Appendix A, is schematic view of an adaptive filter structure operable to filter a measurement signal based on a predicted signal profile.

FIG. 25 is schematic view of an adaptive filter structure operable to filter a measurement signal based on a predicted signal profile.

Figure 26A:
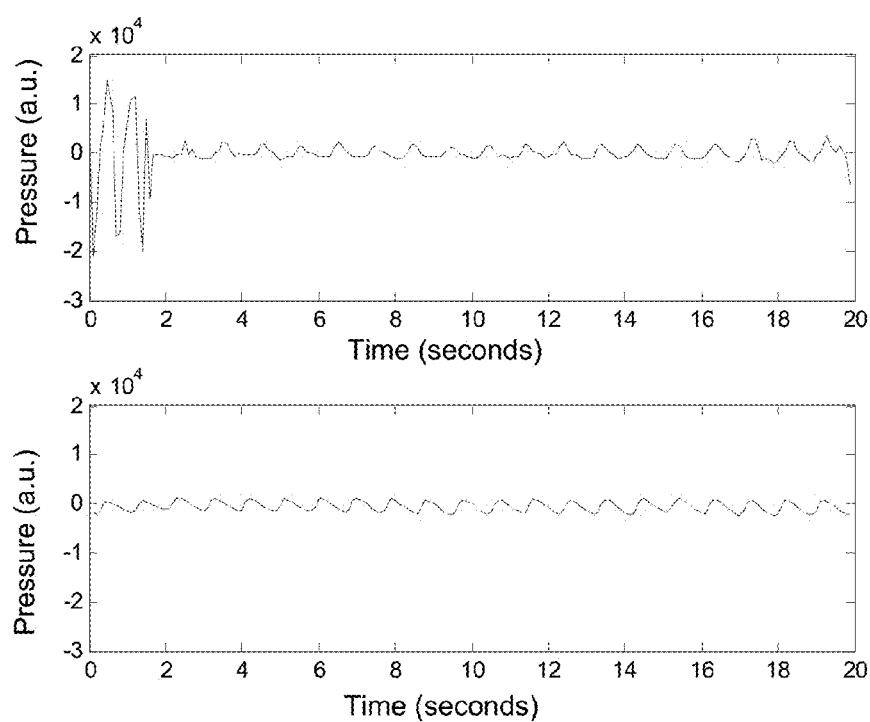
FIG. 26(a), as presented in Appendix A, illustrates a filtered pressure signal (top) and a corresponding heart signal (bottom), obtained from a venous pressure sensor, and FIG. 26(b), as presented in Appendix A, illustrates a filtered pressure signal (top) and a corresponding heart signal (bottom), obtained from an arterial pressure sensor.
Figure 26B:
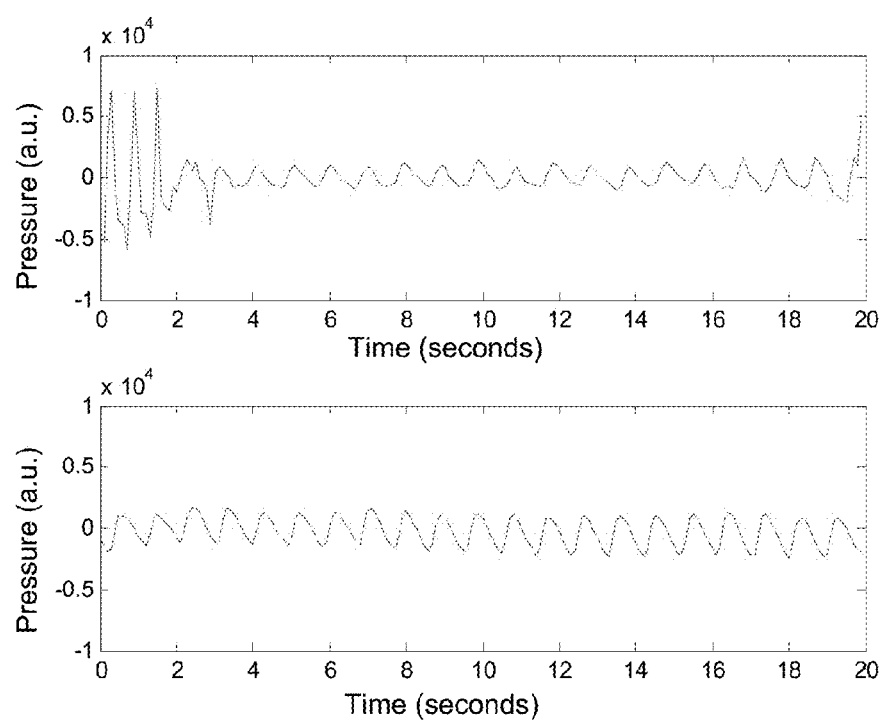

FIG. 26(a) illustrates a filtered pressure signal (top) and a corresponding heart signal (bottom), obtained from a venous pressure sensor, and FIG. 26(b) illustrates a filtered pressure signal (top) and a corresponding heart signal (bottom), obtained from an arterial pressure sensor.

DETAILED DESCRIPTION OF EXEMPLIFYING EMBODIMENTS

In the following, exemplifying embodiments of the invention will be described with reference to fluid containing systems in general. Thereafter, the embodiments and implementations of the invention will be further exemplified in the context of systems for extracorporeal blood treatment.

Throughout the following description, like elements are designated by the same reference signs.

GENERAL

FIG. 15 illustrates a fluid containing system in which a fluid connection C is established between a first fluid containing sub-system S1 and a second fluid containing sub-system S2. The fluid connection C may or may not transfer fluid from one sub-system to the other. A first pulse generator 3 is arranged to generate a series of pressure waves in the fluid within the first sub-system S1, and a second pulse generator 3' is arranged to generate a series of pressure waves in the fluid within the second sub-system S2. A pressure sensor 4a is arranged to measure the fluid pressure in the first sub-system S1. Pressure waves generated by the second pulse generator 3' will travel from the second sub-system S2 to the first sub-system S1, via the connection C, and thus second pulses originating from the second pulse generator 3' will be detected by the pressure sensor 4a in addition to first pulses originating from the first pulse generator 3. It is to be noted that either one of the first and second pulse generators 3, 3' may include more than one pulse-generating device. Further, any such pulse-generating device may or may not be part of the respective sub-system S1, S2.

The system of FIG. 15 further includes a surveillance device 25 which is connected to the pressure sensor 4a, and possibly to one or more additional pressure sensors 4b, 4c, as indicated in FIG. 15. Thereby, the surveillance device 25 acquires one or more pressure signals that are time-dependent to provide a real time representation of the fluid pressure in the first sub-system S1.

Generally, the surveillance device 25 is configured to monitor a functional state or functional parameter of the fluid containing system, by isolating and analysing one or more second pulses in one of the pressure signals. As will be further exemplified in the following, the functional state or parameter may be monitored to identify a fault condition, e.g. in the first or second sub-systems S1, S2, the second pulse generator 3' or the fluid connection C. Upon identification of a fault condition, the surveillance device 25 may issue an alarm or warning signal and/or alert a control system of the first or second sub-systems S1, S2 to take appropriate action. Alternatively or additionally, the surveillance device 25 may be configured to record or output a time sequence of values of the functional state or parameter.

Depending on implementation, the surveillance device 25 may use digital components or analog components, or a combination thereof, for receiving and processing the pressure signal. The device 25 may thus be a computer, or a similar data processing device, with adequate hardware for acquiring and processing the pressure signal in accordance with different embodiments of the invention. Embodiments of the invention may e.g. be implemented by software instructions that are supplied on a computer-readable medium for execution by a processor 25a in conjunction with a memory unit 25b in the computer.

Typically, the surveillance device 25 is configured to continuously process the time-dependent pressure signal(s) to isolate any second pulses. This processing is schematically depicted in the flow chart of FIG. 16. The illustrated processing involves a step 201 of obtaining a first pulse profile u(n) which is a predicted temporal signal profile of the first pulse(s), and a step 202 of filtering the pressure signal d(n), or a pre-processed version thereof, in the time-domain, using the first pulse profile u(n), to essentially eliminate or cancel the first pulse(s) while retaining the second pulse(s) contained in d(n). In the context of the present disclosure, n indicates a sample number and is thus equivalent to a (relative) time point in a time-dependent signal. In step 203, the resulting filtered signal e(n) is then analysed for the purpose of monitoring the aforesaid functional state or parameter.

The first pulse profile is a shape template or standard signal profile, typically given as a time-sequence of data values, which reflects the shape of the first pulse in the time domain. The first pulse profile is also denoted "predicted signal profile" in the following description.

By "essentially eliminating" is meant that the first pulse(s) is(are) removed from the pressure signal to such an extent that the second pulse(s) can be detected and analysed for the purpose of monitoring the aforesaid functional state or parameter.

By filtering the pressure signal in the time-domain, using the first pulse profile, it is possible to essentially eliminate the first pulses and still retain the second pulses, even if the first and second pulses overlap or nearly overlap in the frequency domain. Such a frequency overlap is not unlikely, e.g. if one or both of the first and second pulses is made up of a combination of frequencies or frequency ranges.

Furthermore, the frequency, amplitude and phase content of the first pulse or the second pulse may vary over time. Such variations may be the result of an active control of the first and/or second pulse generator 3, 3', or be caused by drifts in the first and/or second pulse generator 3, 3' or by changes in the hydrodynamic properties of the sub-systems S1, S2 or the fluid connection C. Frequency variations may occur, e.g., when the second pulse generator 3' is a human heart, and the second sub-system S2 thus is the blood system of a human. In healthy subjects under calm conditions, variations in heart rhythm (heart rate variability, HRV) may be as large as 15%. Unhealthy subjects may suffer from severe heart conditions such as atrial fibrillation and supraventricular ectopic beating, which may lead to an HRV in excess of 20%, and ventricular ectopic beating, for which HRV may be in excess of 60%. These heart conditions are not uncommon among, e.g., dialysis patients.

Any frequency overlap may make it impossible or at least difficult to isolate the second pulses in the pressure signal by conventional filtering in the frequency domain, e.g. by operating a comb filter and/or a combination of band-stop or notch filters, typically cascade coupled, on the pressure signal to block out all frequency components originating from the first pulse generator 3. Furthermore, frequency variations make it even harder to successfully isolate second pulses in the pressure signal, since the frequency overlap may vary over time. Even in the absence of any frequency overlap, frequency variations make it difficult to define filters in the frequency domain.

Depending on how well the first pulse profile represents the first pulse(s) in the pressure signal, it may be possible to isolate the second pulses by means of the inventive filtering in the time-domain even if the first and second pulses overlap in frequency, and even if the second pulses are much smaller in amplitude than the first pulses.

Still further, the inventive filtering in the time domain may allow for a faster isolation of second pulses in the pressure signal than a filtering process in the frequency domain. The former may have the ability to isolate a single second pulse in the pressure signal whereas the latter may need to operate on a sequence of first and second pulses in the pressure signal. Thus, the inventive filtering may enable faster determination of the functional state or functional parameter of the fluid containing system.

The effectiveness of the inventive filtering is exemplified in FIG. 17, in which FIG. 17($a$) shows an example of a time-dependent pressure signal d(n) containing first and second pulses with a relative magnitude of 10:1. The first and second pulses have a frequency of 1 Hz and 1.33 Hz, respectively. Due to the difference in magnitude, the pressure signal is dominated by the first pulses. FIG. 17($b$) shows the time-dependent filtered signal e(n) that is obtained after applying the inventive filtering technique to the pressure signal d(n). The filtered signal e(n) is made up of second pulses and noise. It should be noted that there is an absence of second pulses after about 4 seconds, which may be observed by the surveillance device (25 in FIG. 15) and identified as a fault condition of the fluid containing system.

Reverting to FIG. 16, the inventive data processing comprises two main steps: a determination of the first pulse profile u(n) (step 201) and a removal of one or more first pulses from a measurement signal d(n) using the first pulse profile u(n) (step 202).

There are many ways to implement these main steps. For example, the first pulse profile (standard signal profile) may be obtained in a reference measurement, based on a measurement signal from one or more of the pressure sensors 4a-4c in the first sub-system S1, suitably by identifying and possibly averaging a set of first pulse segments in the measurement signal(s). The first pulse profile may or may not be updated intermittently during the actual monitoring of the aforesaid functional state or parameter. Alternatively, a predetermined (i.e. predefined) standard signal profile may be used, which optionally may be modified according to a mathematical model accounting for wear in the first pulse generator, fluid flow rates, tubing dimensions, speed of sound in the fluid, etc. Further, the removal may involve subtracting the first pulse profile from the measurement signal at suitable amplitude and phase. The phase may be indicated by phase information which may be obtained from a signal generated by a phase sensor coupled to the first pulse generator 3, or from a control signal for the first pulse generator 3.

The inventive filtering may also be combined with other filtering techniques to further improve the quality of the filtered signal e(n). In one embodiment, the filtered signal e(n) could be passed through a bandpass filter with a passband in the relevant frequency range for the second pulses. If the second pulses originate from a human heart, the passband may be located within the approximate range of 0.5-4 Hz, corresponding to heart pulse rates of 30-240 beats per minute. In another embodiment, if the current frequency range (or ranges) of the second pulses is known, the passband of the bandpass filter could be actively controlled to a narrow range around the current frequency range. For example, such an active control may be applied whenever the rates of first and second pulses are found to differ by more than a certain limit, e.g. about 10%. The current frequency range may be obtained from the pressure signal, either by intermittently shutting off the first pulse generator 3, or intermittently preventing the first pulses from reaching the relevant pressure sensor 4a-4c. Alternatively, the current frequency range may be obtained from a dedicated sensor in either the first or the second sub-systems S1, S2, or based on a control unit (not shown) for the second pulse generator 3'. According to yet another alternative, the location and/or width of the passband could be set, at least in part, based on patient-specific information, i.e. existing data records for the patient, e.g. obtained in earlier treatments of the same patient. The patient-specific information may be stored in an internal memory of the surveillance device (25 in FIG. 15), on an external memory which is made accessible to the surveillance device, or on a patient card where the information is e.g. transmitted wirelessly to the surveillance device, e.g. by RFID (Radio Frequency IDentification).

These and other embodiments will be explained in further detail below, within the context of a system for extracorporeal blood treatment. To facilitate the following discussion, details of an exemplifying extracorporeal blood flow circuit will be first described.

Monitoring in an Extracorporeal Blood Flow Circuit

FIG. 18 shows an example of an extracorporeal blood flow circuit 20 of the type which is used for dialysis. The extracorporeal blood flow circuit 20 (also denoted "extracorporeal circuit") comprises components 1-14 to be described in the following. Thus, the extracorporeal circuit 20 comprises an access device for blood extraction in the form of an arterial needle 1, and an arterial tube segment 2 which connects the arterial needle 1 to a blood pump 3 which may be of peristaltic type, as indicated in FIG. 18. At the inlet of the pump there is a pressure sensor 4b (hereafter referred to as "arterial sensor") which measures the pressure before the pump in the arterial tube segment 2. The blood pump 3 forces the blood, via a tube segment 5, to the blood-side of a dialyser 6. Many dialysis machines are additionally provided with a pressure sensor 4c (hereafter referred to as "system sensor") that measures the pressure between the blood pump 3 and the dialyser 6. The blood is lead via a tube segment 10 from the blood-side of the dialyser 6 to a venous drip chamber or deaeration chamber 11 and from there back to the patient via a venous tube segment 12 and an access device for blood reintroduction in the form of a venous needle 14. A pressure sensor 4a (hereafter referred to as "venous sensor") is provided to measure the pressure on the venous side of the dialyser 6. In the illustrated example, the pressure sensor 4a measures the pressure in the venous drip chamber. Both the arterial needle 1 and the venous needle 14 are connected to the patient by means of a blood vessel access. The blood vessel access may be of any suitable type, e.g. a fistula, a Scribner-shunt, a graft, etc. Depending on the type of blood vessel access, other types of access devices may be used instead of needles, e.g. catheters. The access devices 1, 14 may alternatively be combined into a single unit.

In relation to the fluid containing system in FIG. 15, the extracorporeal circuit 20 corresponds to the first sub-system S1, the blood pump 3 (as well as any further pulse source(s) within or associated with the extracorporeal circuit 20, such as a dialysis solution pump, valves, etc) corresponds to the first pulse generator 3, the blood system of the patient corresponds to the second sub-system S2, and the fluid connection C corresponds to at least one of the venous-side and arterial-side fluid connections between the patient and the extracorporeal circuit 20.

In FIG. 18, a control unit 23 is provided, i.a., to control the blood flow in the extracorporeal circuit 20 by controlling the revolution speed of the blood pump 3. The extracorporeal circuit 20 and the control unit 23 may form part of an apparatus for extracorporeal blood treatment, such as a dialysis machine. Although not shown or discussed further it is to be understood that such an apparatus performs many other functions, e.g. controlling the flow of dialysis fluid, controlling the temperature and composition of the dialysis fluid, etc.

The system in FIG. 18 also includes a surveillance/monitoring device 25, which is connected to receive a pressure signal from at least one of the pressure sensors 4a-4c and which executes the inventive data processing. In the example of FIG. 18, the surveillance device 25 is also connected to the control unit 23. Alternatively or additionally, the device 25 may be connected to a pump sensor 26 for indicating the revolution speed and/or phase of the blood pump 3. It is to be understood that the surveillance device 25 may include inputs for further data, e.g. any other system parameters that represent the overall system state (see e.g. discussion with reference to FIG. 21 below). The device 25 is tethered or wirelessly connected to a local or remote device 27 for generating an audible/visual/tactile alarm or warning signal. Alternatively or additionally, either device 25, 27 may include a display or monitor for displaying the functional state or parameter resulting from the analysis step (203 in FIG. 16), and/or the filtered signal e(n) resulting from the filtering step (202 in FIG. 16), e.g. for visual inspection.

In FIG. 18, the surveillance device 25 comprises a data acquisition part 28 for pre-processing the incoming signal(s), e.g. including an A/D converter with a required minimum sampling rate and resolution, one or more signal amplifiers, and one or more filters to remove undesired components of the incoming signal(s), such as offset, high frequency noise and supply voltage disturbances.

Figure 19:
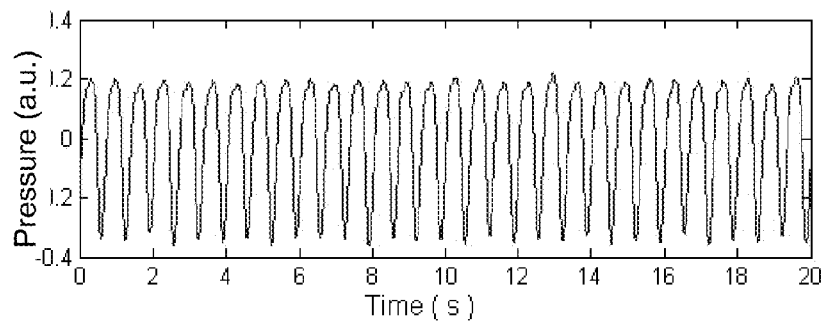
FIG. 19(a), as presented in Appendix A, is a plot in the time domain of a venous pressure signal containing both pump frequency components and a heart signal, and FIG. 19(b), as presented in Appendix A, is a plot of the corresponding signal in the frequency domain.
Figure 19:
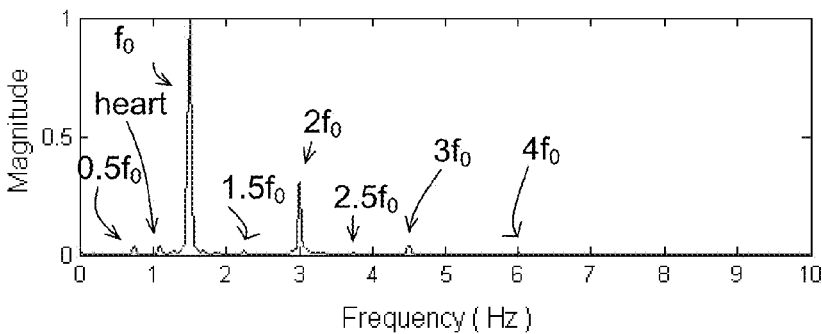

After the pre-processing in the data acquisition part 28, the pre-processed pressure signal is provided as input to a main data processing part 29, which executes the inventive data processing. FIG. 19(*a*) shows an example of such a pre-processed pressure signal in the time domain, and FIG. 19(*b*) shows the corresponding power spectrum, i.e. the pre-processed pressure signal in the frequency domain. The power spectrum reveals that the detected pressure signal contains a number of different frequency components emanating from the blood pump 3. In the illustrated example, there is a frequency component at the base frequency ($f_0$) of the blood pump (at 1.5 Hz in this example), as well as its harmonics $2f_0$, $3f_0$ and $4f_0$. The base frequency, also denoted pump frequency in the following, is the frequency of the pump strokes that generate pressure waves in the extracorporeal circuit 20. For example, in a peristaltic pump of the type shown in FIG. 18, two pump strokes are generated for each full revolution of the rotor 3a. FIG. 19(*b*) also indicates the presence of a frequency component at half the pump frequency ($0.5f_0$) and harmonics thereof, in this example at least $f_0$, $1.5f_0$, $2f_0$ and $2.5f_0$. FIG. 19(*b*) also shows a heart signal (at 1.1 Hz) which in this example is approximately 40 times weaker than the blood pump signal at the base frequency $f_0$.

The main data processing part 29 executes the aforesaid steps 201-203. In step 202, the main data processing part 29 operates to filter the pre-processed pressure signal in the time domain, and outputs a filtered signal or monitoring signal (e(n) in FIG. 16) in which the signal components of the blood pump 3 have been removed. The monitoring signal still contains any signal components that originate from the patient (cf. FIG. 17(*b*)), such as pressure pulses caused by the beating of the patient's heart. There are a number of sources to cyclic physiological phenomena that may generate pressure pulses in the blood stream of the patient, including the heart, the breathing system, or the vasomotor, which is controlled by the autonomic nervous system. Thus, the monitoring signal may contain pressure pulses resulting from a combination of cyclic phenomena in the patient. Generally speaking, the signal components in the monitoring signal may originate from any type of physiological phenomenon in the patient, or combinations thereof, be it cyclic or non-cyclic, repetitive or non-repetitive, autonomous or non-autonomous.

Depending on implementation, the surveillance device 25 may be configured apply further filtering to the monitoring signal to isolate signal components originating from a single cyclic phenomenon in the patient. Alternatively, such signal component filtering is done during the pre-processing of the pressure signal (by the data acquisition part 28). The signal component filtering may be done in the frequency domain, e.g. by applying a cut-off or bandpass filter, since the signal components of the different cyclic phenomena in the patient are typically separated in the frequency domain. Generally, the heart frequency is about 0.5-4 Hz, the breathing frequency is about 0.15-0.4 Hz, the frequency of the autonomous system for regulation of blood pressure is about 0.04-0.14 Hz, the frequency of the autonomous system for regulation of body temperature is about 0.04 Hz.

The surveillance device 25 could be configured to monitor the breathing pattern of the patient, by identifying breathing pulses in the monitoring signal. The resulting information could be used for on-line surveillance for apnoea, hyperventilation, hypoventilation, asthmatic attacks or other irregular breathing behaviours of the patient. The resulting information could also be used to identify coughing, sneezing, vomiting or seizures. The vibrations resulting from coughing/sneezing/vomiting/seizures might disturb other measurement or surveillance equipment that is connected to the patient or the extracorporeal circuit 20. The surveillance device 25 may be arranged to output information about the timing of any coughing/sneezing/vomiting/seizures, such that other measurement or surveillance equipment can take adequate measures to reduce the likelihood that the coughing/sneezing/vomiting/seizures results in erroneous measurements or false alarms. Of course, the ability of identifying coughing/sneezing/vomiting/seizures may also have a medical interest of its own.

The surveillance device 25 could be configured to monitor the heart rate of the patient, by identifying heart pulses in the monitoring signal.

The surveillance device 25 could be configured to collect and store data on the time evolution of the heart rate, the breathing pattern, etc, e.g. for subsequent trending or statistical analysis.

The surveillance device 25 may be configured to monitor the integrity of the fluid connection between the patient and the extracorporeal circuit 20, in particular the venous-side fluid connection (via access device 14). This could be done by monitoring the presence of a signal component originating from, e.g., the patient's heart or breathing system in the monitoring signal. Absence of such a signal component may be taken as an indication of a failure in the integrity of the fluid connection C, and could bring the device 25 to activate an alarm and/or stop the blood flow, e.g. by stopping the blood pump 3 and activating a clamping device 13 on the tube segment 12. For monitoring the integrity of the venous-side fluid connection, also known as VNM (Venous Needle Monitoring), the surveillance device 25 may be configured to generate the monitoring signal based on a pressure signal from the venous sensor 4a. The device 25 may also be connected to pressure sensors 4b, 4c, as well as any additional pressure sensors included in the extracorporeal circuit 20.

The extracorporeal circuit 20 may have the option to operate in a hemodiafiltration mode (HDF mode), in which the control unit 23 activates a second pumping device (HDF pump, not shown) to supply an infusion solution into the blood line upstream and/or downstream of the dialyser 6, e.g. into one or more of tube segments 2, 5, 10 or 12.

Obtaining the Predicted Signal Profile of First Pulses

This section describes different embodiments for predicting or estimating the signal profile of first pulses in the system shown in FIG. 18. The predicted signal profile is typically given as a series of pressure values over a period of time normally corresponding to at least one complete pump cycle of the blood pump 3.

FIG. 20 illustrates an example of a predicted signal profile for the system in FIG. 18. Since the blood pump 3 is a peristaltic pump, in which two rollers 3b engage a tube segment during a full revolution of the rotor 3a, the pressure profile consists of two pump strokes. The pump strokes may result in different pressure values (pressure profiles), e.g. due to slight differences in the engagement between the rollers 3b and the tube segment, and thus it may be desirable for the predicted signal profile to represent both pump strokes. If a lower accuracy of the predicted signal profile can be tolerated, i.e. if the output of the subsequent removal process is acceptable, the predicted signal profile might represent one pump stroke only.

On a general level, the predicted signal profile may be obtained in a reference measurement, through mathematical simulation of the fluid system, or combinations thereof Reference Measurement A first main group of methods for obtaining the predicted signal profile is based on deriving a time-dependent reference pressure signal ("reference signal") from a pressure sensor in the system, typically (but not necessarily) from the same pressure sensor that provides the measurement signal (pressure signal) that is to be processed for removal of first pulses. During this reference measurement, the second pulses are prevented from reaching the relevant pressure sensor, either by shutting down/deactivating the second pulse generator 3' or by isolating the pressure sensor from the second pulses. In the system of FIG. 18, the reference measurement could be carried out during a priming phase, in which the extracorporeal circuit 20 is detached from the patient and a priming fluid is pumped through the blood lines. Alternatively, the reference measurement could be carried in a simulated treatment with blood or any other fluid. Optionally, the reference measurement could involve averaging a plurality of pressure profiles to reduce noise. For example, a plurality of relevant signal segments may be identified in the reference signal, whereupon these segments are aligned to achieve a proper overlap of the pressure profiles in the different segments and then added together. The identifying of relevant signal segments may be at least partially based on timing information which indicates the expected position of each first pulse in the reference signal. The timing information may be obtained from a trigger point in the output signal of the pump sensor 26, in a control signal of the control unit 23, or in the pressure signal from another one of the pressure sensors 4a-4c. For example, a predicted time point of a first pulse in the reference signal can be calculated based on a known difference in arrival time between the trigger point and the pressure sensor that generates the reference signal. In variant, if the reference signal is periodic, relevant signal segments may be identified by identifying crossing points of the reference signal with a given signal level, wherein the relevant signal segments are identified to extend between any respective pairs of crossing points.

In a first embodiment, the predicted signal profile is directly obtained in a reference measurement before the extracorporeal circuit 20 is connected to the patient, and is then used as input to the subsequent removal process, which is executed when the extracorporeal circuit 20 is connected to the patient. In this embodiment, it is thus assumed that the predicted signal profile is representative of the first pulses when the system is connected to the patient Suitably, the same pump frequency/speed is used during the reference measurement and during the removal process. It is also desirable that other relevant system parameters are maintained essentially constant.

FIG. 21 is a flow chart of a second embodiment. In the second embodiment, a reference library or database is first created based on the reference measurement (step 701). The resulting reference library is typically stored in a memory unit, e.g. RAM, ROM, EPROM, HDD, Flash, etc (cf. 25b in FIG. 15) of the surveillance device (cf. 25 in FIG. 15). During the reference measurement, reference pressure signals are acquired for a number of different operational states of the extracorporeal circuit. Each operational state is represented by a unique combination of system parameter values. For each operational state, a reference profile is generated to represent the signal profile of the first pulses. The reference profiles together with associated system parameter values are then stored in the reference library, which is implemented as a searchable data structure, such as a list, look-up table, search tree, etc.

During the actual monitoring process, i.e. when first pulses are to be eliminated from the measurement signal, current state information indicating the current operational state of the fluid containing system is obtained from the system, e.g. from a sensor, a control unit or otherwise (step 702). The current state information may include a current value of one or more system parameters. The current value is then matched against the system parameter values in the reference library. Based on the matching, one or more reference profiles are selected (step 703) and used for preparing the predicted signal profile (step 704).

Generally, the aforesaid system parameters represent the overall system state, including but not limited to the structure, settings, status and variables of the fluid containing system or its components. In the system of FIG. 18, exemplary system parameters may include:

Pump-related parameters: number of active pumps connected directly or indirectly (e.g. in a fluid preparation system for the dialyser) to the extracorporeal circuit, type of pumps used (roller pump, membrane pump, etc), flow rate, revolution speed of pumps, shaft position of pump actuator (e.g. angular or linear position), etc Dialysis machine settings: temperature, ultrafiltration rate, mode changes, valve position/changes, etc Disposable dialysis equipment/material: information on pump chamber/pump segment (material, geometry and wear status), type of blood line (material and geometry), type of dialyser, type and geometry of access devices, etc Dialysis system variables: actual absolute pressures of the system upstream and downstream of the blood pump, e.g. venous pressure (from sensor 4a), arterial pressure (from sensor 4b) and system pressure (from sensor 4c), gas volumes trapped in the flow path, blood line suspension, fluid type (e.g. blood or dialysis fluid), etc Patient status: blood access properties, blood properties such as e.g. hematocrit, plasma protein concentration, etc It is to be understood that any number or combination of system parameters may be stored in the reference library and/or used as search variables in the reference library during the monitoring process.

In the following, the second embodiment will be further explained in relation to a number of examples. In all of these examples, the pump revolution frequency ("pump frequency"), or a related parameter (e.g. blood flow rate) is used to indicate the current operational state of the fluid containing system during the monitoring process. In other words, the pump frequency is used as search variable in the reference library. The pump frequency may e.g. be given by a set value for the blood flow rate output from the control unit, or by an output signal of a sensor that indicates the frequency of the pump (cf. pump sensor 26 in FIG. 18). Alternatively, the pump frequency could be obtained by frequency analysis of the pressure signal from any of the sensors 4a-4c during operation of the fluid system. Such frequency analysis could be achieved by applying any form of harmonics analysis to the pressure signal, such as Fourier or wavelet analysis. As indicated in FIG. 19(b), the base frequency $f_0$ of the pump can be identified in a resulting power spectrum.

In a first example, the reference library is searched for retrieval of the reference profile that is associated with the pump frequency that lies closest to the current pump frequency. If no exact match is found to the current pump frequency, an extrapolation process is executed to generate the predicted signal profile. In the extrapolation process, the retrieved reference profile is scaled in time to the current pump cycle, based on the known difference ("pump frequency difference") between the current pump frequency and the pump frequency associated with the retrieved reference profile. The amplitude scale may also be adjusted to compensate for amplitude changes due to pump frequency, e.g. based on a known function of amplitude as a function of pump frequency. FIG. 22 illustrates a reference profile $r_1(n)$ obtained at a flow rate of 470 ml/min, and predicted signal profile u(n) which is obtained by scaling the reference profile to a flow rate of 480 ml/min. For comparison only, a reference profile $r_{actual}(n)$ obtained at 480 ml/min is also shown, to illustrate that extrapolation process indeed may yield a properly predicted signal profile.

In a second example, the reference library is again searched based on current pump frequency. If no exact match is found to the current pump frequency, a combination process is executed to generate the predicted signal profile. Here, the reference profiles associated with the two closest matching pump frequencies are retrieved and combined. The combination may be done by re-scaling the pump cycle time of the retrieved reference profiles to the current pump frequency and by calculating the predicted signal profile via interpolation of the re-scaled reference profiles. For example, the predicted signal profile u(n) at the current pump frequency v may be given by:

$$u(n)=g(v-v_i)\cdot r_i(n)+(1-g(v-v_i))\cdot r_j(n),$$

wherein $r_i(n)$ and $r_j(n)$ denotes the two retrieved reference profiles, obtained at a pump frequency $v_i$ and $v_j$, respectively, after re-scaling to the current pump frequency v, and g is a relaxation parameter which is given as a function of the frequency difference $(v-v_i)$, wherein $v_i \leq v \leq v_j$ and $0 \leq g \leq 1$. The skilled person realizes that the predicted signal profile u(n) may be generated by combining more than two reference profiles.

FIG. 23(a) illustrates a predicted signal profile u(n) at a current flow rate of 320 ml/min for a measurement signal obtained from the venous sensor 4a in the system of FIG. 18. The predicted signal profile u(n) has been calculated as an average of a reference profile $r_1(n)$ obtained at a flow rate of 300 ml/min from the venous sensor and a reference profile $r_2(n)$ obtained at a flow rate of 340 ml/min from the venous sensor. For comparison only, a reference profile $r_{actual}(n)$ obtained at 320 ml/min is also shown, to illustrate that the combination process indeed may yield a properly predicted signal profile. In fact, the differences are so small that they are only barely visible in the enlarged view of FIG. 23(b).

The first and second examples may be combined, e.g. by executing the extrapolation process of the first example if the pump frequency difference is less than a certain limit, and otherwise executing the combination process of the second example.

In a third embodiment, like in the second embodiment shown in FIG. 21, a number of reference signals are acquired in the reference measurement, wherein each reference signal is obtained for a specific combination of system parameter values. The reference signals are then processed for generation of reference spectra, which are indicative of the energy and phase angle as function of frequency. These reference spectra may e.g. be obtained by Fourier analysis, or equivalent, of the reference signals. Corresponding energy and phase data are then stored in a reference library together with the associated system parameter values (cf. step 701 in FIG. 21). The implementation of the reference library may be the same as in the second embodiment.

During the actual monitoring process, i.e. when first pulses are to be eliminated from the measurement signal, a current value of one or more system parameters is obtained from the fluid containing system (cf. step 702 in FIG. 21). The current value is then matched against the system parameter values in the reference library. Based on the matching, a specific set of energy and phase data may be retrieved from the reference library to be used for generating the predicted signal profile (cf. step 703 in FIG. 21). Generally, the predicted signal profile is generated by adding sinusoids of appropriate frequency, amplitude and phase, according to the retrieved energy and phase data (cf. step 704 in FIG. 21).

Generally speaking, without limiting the present disclosure, it may be advantageous to generate the predicted signal profile from energy and phase data when the first pulses (to be removed) contain only one or a few base frequencies (and harmonics thereof), since the predicted signal profile can be represented by a small data set (containing energy and phase data for the base frequencies and the harmonics). One the other hand, when the power spectrum of the first pulses is more complex, e.g. a mixture of many base frequencies, it may instead be preferable to generate the predicted signal profile from one or more reference profiles.

FIG. 24(a) represents an energy spectrum of a reference signal acquired at a flow rate of 300 ml/min in the system of FIG. 18. In this example, the reference signal essentially consists of a basic pump frequency at 1.2 Hz ($f_0$, first harmonic) and a set of overtones of this frequency (second and further harmonics). Compared to the power spectrum of FIG. 19(b), the pressure signals used for generating the graphs in FIG. 24(a)-24(d) do not contain any significant frequency component at $0.5f_0$ and its harmonics. The graph in FIG. 24(a) displays the relative energy distribution, wherein the energy values have been normalized to the total energy for frequencies in the range of 0-10 Hz. FIG. 24(b) represents energy spectra of reference signals acquired at three different flow rates in the system of FIG. 18. The energy spectra are given in logarithmic scale versus harmonic number (first, second, etc). As shown, an approximate linear relationship can be identified between the logarithmic energy and harmonic number for the first four to five harmonic numbers. This indicates that each energy spectrum may be represented by a respective exponential function. FIG. 24(c) illustrates the data of FIG. 24(b) in linear scale, wherein a respective polynomial function has been fitted to the data. As indicated in FIGS. 24(a)-24(c), the energy spectra may be represented in different formats in the reference library, e.g. as a set of energy values associated with discrete frequency values or harmonic numbers, or as an energy function representing energy versus frequency/harmonic number.

FIG. 24(d) illustrates a phase angle spectrum acquired together with the energy spectrum in FIG. 24(a), i.e. for a flow rate of 300 ml/min. The graph in FIG. 24(d) illustrates phase angle as a function of frequency, and a linear function has been fitted to the data. In an alternative representation (not shown), the phase spectrum may be given as a function of harmonic number. Like the energy spectra, the phase spectra may be represented in different formats in the reference library, e.g. as a set of phase angle values associated with discrete frequency values or harmonic numbers, or as a phase function representing phase angle versus frequency/harmonic number.

From the above, it should be understood that the energy and phase data that are stored the reference library can be used to generate the predicted signal profile. Each energy value in the energy data corresponds to an amplitude of a sinusoid with a given frequency (the frequency associated with the energy value), wherein the phase value for the given frequency indicates the proper phase angle of the sinousoid. This method of preparing the predicted signal profile by combining (typically adding) sinusoids of appropriate frequency, amplitude and phase angle allows the predicted signal profile to include all harmonics of the pump frequency within a desired frequency range.

When a predicted signal profile is to be generated, the reference library is first searched based on a current value of one or more system parameters, such as the current pump frequency. If no exact match is found in the reference library, a combination process may be executed to generate the predicted signal profile. For example, the two closest matching pump frequencies may be identified in the reference library and the associated energy and phase data may be retrieved and combined to form the predicted signal profile. The combination may be done by interpolating the energy data and the phase data. In the example of FIGS. 24(a)-24(d), an interpolated energy value may be calculated for each harmonic number, and similarly an interpolated phase value could be calculated for each harmonic number. Any type of interpolation function could be used, be it linear or non-linear.

In the first, second and third embodiments, the reference signals and the measurement signals are suitably obtained from the same pressure sensor unit in the fluid containing system. Alternatively, different pressure sensor units could be used, provided that the pressure sensor units yield identical signal responses with respect to the first pulses or that the signal responses can be matched using a known mathematical relationship.

To further improve the first, second and third embodiments, the process of generating the predicted signal profile may also involve compensating for other potentially relevant factors that differ between the reference measurement and the current operational state. These so-called confounding factors may comprise one or more of the system parameters listed above, such as absolute average venous and arterial pressures, temperature, blood hematocrit/viscosity, gas volumes, etc. This compensation may be done with the use of predefined compensation formulas or look-up tables.

In further variations, the second and third embodiments may be combined, e.g. in that the reference library stores not only energy and phase data, but also reference profiles, in association with system parameter value(s). When an exact match is found in the library, the reference profile is retrieved from the library and used as the predicted signal profile, otherwise the predicted signal profile is obtained by retrieving and combining (e.g. interpolating) the energy and phase data, as in the third embodiment. In a variant, the predicted signal profile u(n) at the current pump frequency v is obtained by:

$$u(n)=r_i(n)-r^r_i(n)+r^v(n),$$

wherein $r_i(n)$ denotes a reference profile that is associated with the closest matching pump frequency $v_i$ in the reference library, $r^r_i(n)$ denotes a reference profile that is reconstructed from the energy and phase data associated with the closest matching pump frequency $v_i$ in the reference library, and $r^v(n)$ denotes an estimated reference profile at the current pump frequency v. The estimated reference profile $r^v(n)$ may be obtained by applying predetermined functions to estimate the energy and phase data, respectively, at the current pump frequency v based on the energy and phase data associated with the closest matching pump frequency $v_i$. With reference to FIGS. 24(b)-24(c), such a predetermined function may thus represent the change in energy data between different flow rates. Alternatively, the estimated reference profile $r^v(n)$ may be obtained by retrieving and combining (e.g. interpolating) energy and phase data for the two closest matching pump frequencies $v_i$ and $v_j$ as in the third embodiment.

In a further variant, the reference measurement is made during regular operation of the fluid containing system, instead of or in addition to any reference measurements made before regular operation (e.g. during priming or simulated treatments with blood). Such a variant presumes that it is possible to intermittently shut off the second pulse generator, or to intermittently prevent the second pulses from reaching the relevant pressure sensor. This approach is more difficult in the extracorporeal circuit 20 of FIG. 18 if the reference signals and the measurement signals are obtained from the one and the same pressure sensor. However, this approach can e.g. be applied if the fluid system includes one pressure sensor that is substantially isolated from the second pulses. In such a situation, the reference profile (or reference spectra) may be obtained from the isolated sensor, and used for generating the predicted signal profile (optionally after adjustment/modification for differences in confounding factors), which is then used for removing first pulses from a measurement signal that contains both first and second pulses. For example, the pressure signal from the system sensor 4c in the circuit 20 of FIG. 18 may be essentially isolated from the second pulses that originate from the patient, and this pressure signal may thus be used in a reference measurement.

As explained above, the extracorporeal circuit 20 in FIG. 18 may be switched into a HDF mode, in which an additional HDF pump is activated to supply an infusion liquid into the blood line of the extracorporeal circuit 20. Such a change of operating mode may cause a change in the signal characteristics of the first pulses in the measurement signal. Thus, it may necessary to account for this change, by ensuring that the reference library includes appropriate reference data (reference profiles and/or energy and phase angle data) associated with this operational state.

Alternatively, it may be desirable to isolate the pressure pulses originating from the HDF pump. This could be achieved by obtaining a reference profile from the pressure signal of the arterial sensor 4b (FIG. 18). The arterial pressure signal includes pressure pulses originating from the patient and from the blood pump 3, whereas pressure pulses originating from the HDF pump are significantly damped by the patient and the blood pump 3, respectively, and thus barely reach the arterial sensor 4b. On the other hand, the pressure signals of the venous sensor 4a and the system sensor 4c contain pressure pulses originating from both the patient, the blood pump 3 and the HDF pump. Thus, the arterial pressure signal may be used for obtaining the predicted signal profile of the combined pressure pulses originating from the blood pump 3 and the patient as they should look in the pressure signal from the venous sensor 4a or the system sensor 4c. The predicted signal profile may then be used for isolating the pressure pulses originating from the HDF pump in the pressure signal from the venous sensor 4a or the system sensor 4c. In this example, the patient and the extracorporeal circuit 20 could be regarded as a first sub-system (S1 in FIG. 15) and the HDF pump and the associated infusion tubing could be regarded as a second sub-system (S2 in FIG. 15), which are connected via a fluid connection. Thus, in this example, the inventive data processing is not applied to isolate pulses originating from a cyclic physiological phenomenon in the patient, but pulses originating from another pump in the fluid system. It should be realized that in other arrangements, the reference profile may be obtained from the pressure signal of the venous sensor 4a (FIG. 18), and used for processing the pressure signal of the arterial sensor 4b or system sensor 4c.

Simulations

As an alternative to the use of reference measurements, the predicted signal profile may be obtained directly through simulations, i.e. calculations using a mathematical model of the fluid containing system, based on current state information indicating the current operational state of the system. Such current state information may include a current value of one or more of the above-mentioned system parameters. The model may be based on known physical relationships of the system components (or via an equivalent representation, e.g. by representing the system as an electrical circuit with fluid flow and pressure being given by electrical current and voltage, respectively). The model may be expressed, implicitly or explicitly, in analytical terms. Alternatively, a numerical model may be used. The model could be anything from a complete physical description of the system to a simple function. In one example, such a simple function could convert data on the instantaneous angular velocity of the pump rotor 3a to a predicted signal profile, using empirical or theoretical data. Such data on the instantaneous angular velocity might be obtained from the pump sensor 26 in FIG. 18.

In another embodiment, simulations are used to generate reference profiles for different operational states of the system. These reference profiles may then be stored in a reference library, which may be accessed and used in the same way as described above for the second and third embodiments. It is also to be understood that reference profiles (and/or corresponding energy and phase angle data) obtained by simulations may be stored together with reference profiles (and/or corresponding energy and phase angle data) obtained by reference measurement.

Removal of First Pulses

There are several different ways of removing one or more first pulses from the measurement signal, using the predicted signal profile. Here, two different removal processes will be described: Single Subtraction and Adaptive Filtering. Of course, the description of removal processes and their implementations is not comprehensive (neither of the different alternatives nor of the implementations), which is obvious to a person skilled in the art.

Depending on implementation, the predicted signal profile may be input to the removal process as is, or the predicted signal profile may be duplicated to construct an input signal of suitable length for the removal process.

Single Subtraction

In this removal process, a single predicted signal profile is subtracted from the measurement signal. The predicted signal profile may be shifted and scaled in time and scaled in amplitude in any way, e.g. to minimize the error of the removal. Different minimization criterions may be used for such an auto-scaling, e.g., minimizing the sum of the squared errors, or the sum of the absolute errors. Alternatively or additionally, the predicted signal profile is shifted in time based on timing information that indicates the expected timing of the first pulse(s) in the measurement signal. The timing information may be obtained in the same way as described above in relation to the averaging of pressure segments in the reference signal.

One potential limitation of this removal process is that the relationship between different frequencies in the predicted signal profile is always the same, since the process only shifts and scales the predicted signal profile. Thus, it is not possible to change the relationship between different harmonic frequencies, neither is it possible to use only some of the frequency content in the predicted signal profile and to suppress other frequencies. To overcome this limitation, adaptive filtering may be used since it uses a linear filter before subtraction, e.g. as described in the following.

Adaptive Filtering

FIG. 25 is a schematic overview of an adaptive filter 30 and an adaptive filter structure which is designed to receive the predicted signal profile u(n) and a measurement signal d(n), and to output an error signal e(n) which forms the aforesaid monitoring signal in which the first pulses are removed.

Adaptive filters are well-known electronic filters (digital or analog) that self-adjust their transfer function according to an optimizing algorithm. Specifically, the adaptive filter 30 includes a variable filter 32, typically a finite impulse response (FIR) filter of length M with filter coefficients w(n).

Even if adaptive filters are known in the art, they are not readily applicable to cancel the first pulses in the measurement signal d(n). In the illustrated embodiment, this has been achieved by inputting the predicted signal profile u(n) to the variable filter 32, which processes the predicted signal profile u(n) to generate an estimated measurement signal $\hat{d}(n)$, and to an adaptive update algorithm 34, which calculates the filter coefficients of the variable filter 32 based on the predicted signal profile u(n) and the error signal e(n). The error signal e(n) is given by the difference between the measurement signal d(n) and the estimated measurement signal d̂(n).

Basically, the adaptive filtering also involves a subtraction of the predicted signal profile u(n) from the measurement signal d(n), since each of the filter coefficients operates to shift and possibly re-scale the amplitude of the predicted signal profile u(n). The estimated measurement signal d̂(n), which is subtracted from the measurement signal d(n) to generate the error signal e(n), is thus formed as a linear combination of M shifted predicted signal profiles u(n), i.e. a linear filtering of u(n).

The adaptive update algorithm 34 may be implemented in many different ways, some of which will be described below. The disclosure is in no way limited to these examples, and the skilled person should have no difficulty of finding further alternatives based on the following description.

There are two main approaches to adaptive filtering: stochastic and deterministic. The difference lies in the minimization of the error signal e(n) by the update algorithm 34, where different minimization criteria are obtained whether e(n) is assumed to be stochastic or deterministic. A stochastic approach typically uses a cost function J with an expectation in the minimization criterion, while a deterministic approach typically uses a mean. The squared error signal $e^2(n)$ is typically used in a cost function when minimizing e(n), since this results in one global minimum. In some situations, the absolute error |e(n)| may be used in the minimization, as well as different forms of constrained minimizations. Of course, any form of the error signal may be used, however convergence towards a global minimum is not always guaranteed and the minimization may not always be solvable.

In a stochastic description of the signal, the cost function may typically be according to, $$J(n)=E\{|e(n)|^2\},$$

and in a deterministic description of the signal the cost function may typically be according to, $$J(n)=\Sigma e^2(n).$$

The first pulses will be removed from the measurement signal d(n) when the error signal e(n) (cost function J(n)) is minimized. Thus, the error signal e(n) will be cleaned from first pulses while retaining the second pulses, once the adaptive filter 30 has converged and reached the minimum error.

In order to obtain the optimal filter coefficients w(n) for the variable filter 32, the cost function J needs to be minimized with respect to the filter coefficients w(n). This may be achieved with the cost function gradient vector ∇J, which is the derivative of J with respect to the different filter coefficients $w_0, w_1, \ldots, w_{M-1}$. Steepest Descent is a recursive method (not an adaptive filter) for obtaining the optimal filter coefficients that minimize the cost function J. The recursive method is started by giving the filter coefficients an initial value, which is often set to zero, i.e., w(0)=0. The filter coefficients is then updated according to, $$w(n+1)=w(n)+\tfrac{1}{2}\mu[-\nabla J(n)],$$

where w is given by, $$w=[w_0\, w_1 \ldots w_{M-1}]^T M\times 1.$$

Furthermore, the gradient vector ∇J points in the direction in which the cost is growing the fastest. Thus, the filter coefficients are corrected in the direction opposite to the gradient, where the length of the correction is influenced through the step size parameter μ. There is always a risk for the Steepest Descent algorithm to diverge, since the algorithm contains a feedback. This sets boundaries on the step size parameter μ in order to ensure convergence. It may be shown that the stability criterion for the Steepest Descent algorithm is given by, $$0<\mu<\frac{2}{\lambda_{max}}$$

where $\lambda_{max}$ is the largest eigenvalue of R, the correlation matrix of the predicted signal profile u(n), given by $$R = E[\bar{u}(n)\bar{u}^T(n)] = \begin{bmatrix} r(0) & r(1) & \ldots & r(M-1) \\ r(1) & r(0) & & r(M-2) \\ \vdots & \vdots & \ddots & \vdots \\ r(M-1) & r(M-2) & \ldots & r(0) \end{bmatrix},$$

where ū(n) is given by, $$\bar{u}(n)=[u(n)u(n-1)\ldots u(n-M+1)]^T M\times 1.$$

If the mean squared error (MSE) cost function (defined by $J=E\{|e(n)|^2\}$) is used, it may be shown that the filter coefficients are updated according to, $$w(n+1)=w(n)+\mu E[\bar{u}(n)e(n)],$$

where e(n) is given by, $$e(n)=d(n)-\bar{u}^T(n)w(n).$$

The Steepest Descent algorithm is a recursive algorithm for calculation of the optimal filter coefficients when the statistics of the signals are known. However, this information is often unknown. The Least Mean Squares (LMS) algorithm is a method that is based on the same principles as the Steepest Descent algorithm, but where the statistics is estimated continuously. Thus, the LMS algorithm is an adaptive filter, since the algorithm can adapt to changes in the signal statistics (due to continuous statistic estimations), although the gradient may become noisy. Because of the noise in the gradient, the LMS algorithm is unlikely to reach the minimum error $J_{min}$, which the Steepest Descent algorithm does. Instantaneous estimates of the expectation are used in the LMS algorithm, i.e., the expectation is removed. Thus, for the LMS algorithm, the update equation of the filter coefficients becomes $$w(n+1)=w(n)+\mu\bar{u}(n)e(n).$$

The convergence criterion of the LMS algorithm is the same as for the Steepest Descent algorithm. In the LMS algorithm, the step size is proportional to the predicted signal profile u(n), i.e., the gradient noise is amplified when the predicted signal profile is strong. One solution to this problem is to normalize the update of the filter coefficients with $$\|\bar{u}(n)\|^2=\bar{u}^T(n)\bar{u}(n)$$

The new update equation of the filter coefficients is called the Normalized LMS, and is given by $$w(n+1) = w(n) + \frac{\tilde{\mu}}{a+\|\bar{u}(n)\|^2}\bar{u}(n)e(n),$$

where 0<ũ<2, and a is a positive protection constant.

There are many more different alternatives to the LMS algorithm, where the step size is modified. One of them is to use a variable adaptation step, $$w(n+1)=w(n)+\alpha(n)\bar{u}(n)e(n),$$

where α(n) for example may be, $$\alpha(n) = \frac{1}{n+c},$$

where c is a positive constant. It is also possible to choose independent adaptation steps for each filter coefficient in the LMS algorithm, e.g., according to, $$w(n+1)=w(n)+A\bar{u}(n)e(n),$$

where A is given by, $$A = \begin{bmatrix} \alpha_1 & 0 & 0 & \cdots & 0 \\ 0 & \alpha_2 & 0 & \cdots & 0 \\ 0 & 0 & \alpha_3 & \cdots & 0 \\ \vdots & \vdots & \vdots & \ddots & \vdots \\ 0 & 0 & 0 & \cdots & \alpha_M \end{bmatrix}.$$

If instead the following cost function $$J(n)=E\{|e(n)|\}$$

is used, then the update equation becomes $$w(n+1)=w(n)+\alpha\,\mathrm{sign}[e(n)]\bar{u}(n).$$

This adaptive filter is called the Sign LMS, which is used in applications with extremely high requirements on low computational complexity.

Another adaptive filter is the Leaky LMS, which uses a constrained minimization with the following cost function $$J(n)=E\{|e(n)|^2\}+\alpha\|w(n)\|^2.$$

This constraint has the same effect as if white noise with variance α was added to the predicted signal profile u(n). As a result, the uncertainty in the input signal u(n) is increased, which tends to hold the filter coefficients back. The Leaky LMS is preferably used when R, the correlation matrix of u(n), has one or more eigenvalues equal to zero. However, in systems without noise, the Leaky LMS makes performance poorer. The update equation of the filter coefficients for the Leaky LMS is given by, $$w(n+1)=(1-\mu a)w(n)+\mu\bar{u}(n)e(n).$$

Instead of minimizing the MSE cost function as above, the Recursive Least Squares (RLS) adaptive filter algorithm minimizes the following cost function $$J(n) = \sum_{i=1}^{n} \lambda^{n-i}|e(i)|^2,$$

where λ is called forgetting factor, $0<\lambda\le 1$, and the method is called Exponentially Weighted Least Squares. It may be shown that the update equations of the filter coefficients for the RLS algorithm are, after the following initialization $$w(0)=0_{M\times 1}$$

$$P(0)=\delta^{-1}I_{M\times M}$$

where $I_{M\times M}$ is the identity matrix M×M, given according to $$k(n) = \frac{\lambda^{-1}P(n-1)\bar{u}(n)}{1+\lambda^{-1}\bar{u}^T(n)P(n-1)\bar{u}(n)}$$

$$\xi(n) = d(n) - w^T(n-1)\bar{u}(n)$$

$$w(n) = w(n-1) + k(n)\xi(n)$$

$$P(n) = \lambda^{-1}P(n-1) - \lambda^{-1}k(n)\bar{u}^T(n)P(n-1),$$

where δ is a small positive constant for high signal-to-noise ratio (SNR), and a large positive constant for low SNR, $\delta<<0.01\sigma^2$, and ξ(n) corresponds to e(n) in the preceding algorithms. During the initialization phase the following cost function $$J(n) = \sum_{i=1}^{n} \lambda^{n-i}|e(i)|^2 + \delta\lambda^n\|w(n)\|^2,$$

is minimized instead, due to the use of the initialization $P(0)=\delta^{-1}$ I. The RLS algorithm converges in approximately 2M iterations, which is considerably faster than for the LMS algorithm. Another advantage is that the convergence of the RLS algorithm is independent of the eigenvalues of R, which is not the case for the LMS algorithm.

Several RLS algorithms running in parallel may be used with different λ and δ, which may be combined in order to improve performance, i.e., λ=1 may also be used in the algorithm (steady state solution) with many different δ:s.

It should be noted that both the LMS algorithm and the RLS algorithm can be implemented in fixed-point arithmetic, such that they can be run on a processor that has no floating point unit, such as a low-cost embedded microprocessor or microcontroller.

To illustrate the effectiveness of the removal process using an adaptive filter, the top graph in FIG. 26(a) illustrates the error signal e(n) output by the adaptive filter structure in FIG. 25, using an RLS algorithm as adaptive update algorithm 32, operating on a measurement signal from the venous sensor 4a in FIG. 18, at a flow rate of 430 ml/min. The adaptive filter structure is provided with a predicted signal profile obtained in a reference measurement at the same flow rate. The RLS algorithm, designed with M=15, converges after about 2M, which equals 3 seconds with the current sampling frequency of 10 Hz. The top graph thus shows the measurement signal after elimination of the first pulses. The bottom graph in FIG. 26(a) is included for reference, and shows the measurement signal from the venous sensor 4a while the blood pump 3 is stopped. Clearly, the adaptive filtering is operable to provide, after a convergence period, a monitoring signal that properly represents the second pulses.

FIG. 26 (b) corresponds to FIG. 26 (a), but is obtained for a measurement signal from the arterial sensor 4b in FIG. 18.

Irrespective of implementation, the performance of the adaptive filter 30 (FIG. 25) may be further improved by switching the adaptive filter 30 to a static mode, in which the update algorithm 34 is disabled and thus the filter coefficients of the filter 32 (FIG. 25) are locked to a current set of values. The switching of the adaptive filter 30 may be controlled by an external process that analyses the second pulses in the error signal e(n), typically in relation to first pulse data. The first pulse data may be obtained from the measurement signal, a reference signal (see above), a dedicated pulse sensor, a control unit for the first pulse generator, etc. The adaptive filter 30 may be switched into the static mode if the external process reveals that the rate of second pulses starts to approach the rate of the first pulses and/or that the amplitude of the second pulses is very weak (in relation to an absolute limit, or in relation to a limit given by the amplitude of the first pulses). The adaptive filter may remain in static mode for a predetermined time period, or until released by the process.

The invention has mainly been described above with reference to a few embodiments. However, as readily appreciated by a person skilled in the art, other embodiments than the ones disclosed above are equally possible with the scope and spirit of the invention, which is defined and limited only by the appended patent "items".

For example, the measurement and reference signals may originate from any conceivable type of pressure sensor, e.g. operating by resistive, capacitive, inductive, magnetic or optical sensing, and using one or more diaphragms, bellows, Bourdon tubes, piezo-electrical components, semiconductor components, strain gauges, resonant wires, accelerometers, etc.

Although FIG. 15 indicates that the pressure sensor 4a-4c is connected to the first sub-system S1, it may instead be connected to measure the fluid pressure in the second sub-system S2. Further, the fluid containing system need not be partitioned into first and second sub-systems S1, S2 connected via a fluid connection C, but could instead be a unitary fluid containing system associated with a first pulse generator and a second pulse generator, wherein the each pressure sensor is arranged in the fluid containing system to detect a first pulse originating from the first pulse generator and a second pulse originating from the second pulse generator.

Further, the inventive technique is applicable for monitoring in all types of extracorporeal blood flow circuits in which blood is taken from the systemic blood circuit of the patient to have a process applied to it before it is returned to the patient. Such blood flow circuits include circuits for hemodialysis, hemofiltration, hemodiafiltration, plasmapheresis, apheresis, extracorporeal membrane oxygenation, assisted blood circulation, and extracorporeal liver support/dialysis. The inventive technique is likewise applicable for monitoring in other types of extracorporeal blood flow circuits, such as circuits for blood transfusion, infusion, as well as heart-lung-machines.

The inventive technique is also applicable to fluid systems containing other liquids than blood.

Further, the inventive technique is applicable to remove pressure pulses originating from any type of pumping device, not only rotary peristaltic pumps as disclosed above, but also other types of positive displacement pumps, such as linear peristaltic pumps, diaphragm pumps, as well as centrifugal pumps. In fact, the inventive technique is applicable for removing pressure pulses that originate from any type of pulse generator, be it mechanic or human.

Likewise, the inventive technique is applicable to isolate pressure pulses originating from any type of pulse generator, be it human or mechanic.

The inventive technique need not operate on real-time data, but could be used for processing off-line data, such as a previously recorded measurement signal.

APPENDIX A

Items

1. A method for processing a time-dependent measurement signal (d(n)) obtained from a pressure sensor (4a-4c) in a fluid containing system associated with a first pulse generator (3) and a second pulse generator (3"), wherein the pressure sensor (4a-4c) is arranged in the fluid containing system to detect a first pulse originating from the first pulse generator (3) and a second pulse originating from the second pulse generator (3'), said method comprising:
receiving the measurement signal (d(n)),
obtaining a first pulse profile (u(n)) which is a predicted temporal signal profile of the first pulse, and
filtering the measurement signal (d(n)) in the time-domain, using the first pulse profile (u(n)), to essentially eliminate the first pulse while retaining the second pulse.

2. The method of item 1, wherein the step of filtering comprises subtracting the first pulse profile (u(n)) from the measurement signal (d(n)).

3. The method of item 2, wherein step of subtracting comprises adjusting a phase of the first pulse profile (u(n)) in relation to the measurement signal (d(n)), wherein said phase is indicated by phase information obtained from a phase sensor (26) coupled to the first pulse generator (3), or from a control unit (23) for the first pulse generator (3).

4. The method of any preceding item, wherein the first pulse profile (u(n)) is obtained in a reference measurement in said fluid containing system, wherein the reference measurement comprises the steps of: operating the first pulse generator (3) to generate at least one first pulse, and obtaining the first pulse profile (u(n)) from a reference signal generated by a reference pressure sensor (4a-4c) in the fluid containing system.

5. The method of item 4, wherein the first pulse generator (3) is operated to generate a sequence of first pulses during the reference measurement, and wherein the first pulse profile (u(n)) is obtained by identifying and averaging a set of first pulse segments in the reference signal.

6. The method of item 4 or 5, wherein the reference measurement is effected intermittently during operation of the fluid containing system to provide an updated first pulse profile (u(n)).

7. The method of any one of items 4-6, wherein the pressure sensor (4a-4c) is used as said reference pressure sensor.

8. The method of any one of items 1-3, wherein the step of obtaining comprises obtaining a predetermined signal profile.

9. The method of item 8, wherein the step of obtaining further comprises modifying the predetermined signal profile according to a mathematical model based on a current value of one or more system parameters of the fluid containing system.

10. The method of any one of items 4-7, wherein the fluid containing system is operated, during the reference measurement, such that the reference signal contains a first pulse and no second pulse.

11. The method of any one of items 4-7, wherein the reference measurement comprises: obtaining a combined pulse profile based on a first reference signal containing a first pulse and a second pulse; obtaining a second pulse profile based on a second reference signal containing a second pulse and no first pulse, and obtaining the predicted signal profile by subtracting the second pulse profile from the combined pulse profile.

12. The method of item 1, further comprising the step of obtaining a current value of one or more system parameters of the fluid containing system, wherein the first pulse profile (u(n)) is obtained as a function of the current value.

13. The method of item 12, wherein said step of obtaining the first pulse profile (u(n)) comprises: identifying, based on the current value, one or more reference profiles ($r_1(n)$, $r_2(n)$) in a reference database; and obtaining the first pulse profile (u(n)) based on said one or more reference profiles ($r_1(n)$, $r_2(n)$).

14. The method of item 13, wherein said one or more system parameters is indicative of the rate of first pulses in the fluid containing system.

15. The method of item 14, wherein the first pulse generator (3) comprises a pumping device and the system parameter is indicative of a pump frequency of the pumping device.

16. The method of any one of items 13-15, wherein each reference profile ($r_1(n)$, $r_2(n)$) in the reference database is obtained by a reference measurement in the fluid containing system for a respective value of said one or more system parameters.

17. The method of item 12, wherein said step of obtaining the first pulse profile (u(n)) comprises: identifying, based on the current value, one or more combinations of energy and phase angle data in a reference database; and obtaining the first pulse profile (u(n)) based on said one or more combinations of energy and phase angle data.

18. The method of item 17, wherein the first pulse profile (u(n)) is obtained by combining a set of sinusoids of different frequencies, wherein the amplitude and phase angle of each sinousoid is given by said one or more combinations of energy and phase angle data.

19. The method of item 12, wherein said step of obtaining the first pulse profile (u(n)) comprises: inputting the current value into an algorithm which calculates the response of the pressure sensor (4a-4c) based on a mathematical model of the fluid containing system.

20. The method of any preceding item, wherein the step of filtering comprises subtracting the first pulse profile (u(n)) from the measurement signal (d(n)), and wherein the step of subtracting is preceded by an adjustment step, in which at least one of the amplitude, the time scale and the phase of the first pulse profile (u(n)) is adjusted with respect to the measurement signal (d(n)).

21. The method of item 20, wherein the adjustment step comprises minimizing a difference between the first pulse profile (u(n)) and the measurement signal (d(n)).

22. The method of any one of items 1-19, wherein the step of filtering comprises: supplying the first pulse profile (u(n)) as input to an adaptive filter (30); calculating an error signal (e(n)) between the measurement signal (d(n)) and an output signal ($\hat{d}(n)$) of the adaptive filter (30); and providing the error signal (e(n)) as input to the adaptive filter (30), whereby the adaptive filter (30) is arranged to essentially eliminate the first pulse in the error signal (e(n)).

23. The method of item 22, wherein the adaptive filter (30) comprises a finite impulse response filter (32) with filter coefficients that operate on the first pulse profile (u(n)) to generate the output signal ($\hat{d}(n)$), and an adaptive algorithm (34) which optimizes the filter coefficients as a function of the error signal (e(n)) and the first pulse profile (u(n)).

24. The method of item 22 or 23, further comprising the step of controlling the adaptive filter (30) to lock the filter coefficients, based on a comparison of the rate and/or amplitude of the second pulses to a limit value.

25. The method of any preceding item, wherein the fluid containing system comprises an extracorporeal blood flow circuit (20) for connection to a blood system in a human body, and wherein the first pulse generator comprises a pumping device (3) in the extracorporeal blood flow circuit (20), and wherein the second pulse generator (3') comprises a physiological pulse generator in the human body.

26. The method of item 25, wherein the second pulse generator (3') is at least one of a heart, a breathing system, and a vasomotor affected by an autonomic nervous system.

27. The method of item 25 or 26, wherein the extracorporeal blood flow circuit (20) comprises an arterial access device (1), a blood processing device (6), and a venous access device (14), wherein the human blood system comprises a blood vessel access, wherein the arterial access device (1) is configured to be connected to the human blood system, wherein the venous access device (14) is configured to be connected to the blood vessel access to form a fluid connection (C), and wherein the first pulse generator comprises a pumping device (3) arranged in the extracorporeal blood flow circuit (20) to pump blood from the arterial access device (1) through the blood processing device (6) to the venous access device (14), said method comprising the step of receiving the measurement signal (d(n)) either from a venous pressure sensor (4a) located downstream of the pumping device (3), or from an arterial pressure sensor (4b) located upstream of the pumping device (3).

28. A computer program product comprising instructions for causing a computer to perform the method of any one of items 1-27.

29. A device for processing a time-dependent measurement signal (d(n)) obtained from a pressure sensor (4a-4c) in a fluid containing system associated with a first pulse generator (3) and a second pulse generator (3"), wherein the pressure sensor (4a-4c) is arranged in the fluid containing system to detect a first pulse originating from the first pulse generator (3) and a second pulse originating from the second pulse generator (3'), said device comprising:

an input (28) for the measurement signal (d(n)), a signal processor (25a) connected to said input (28) and comprising a processing module (29) configured to obtain a first pulse profile (u(n)) which is a predicted temporal signal profile of the first pulse, and to filter the measurement signal (d(n)) in the time-domain, using the first pulse profile (u(n)), to essentially eliminate the first pulse while retaining the second pulse.

30. A device for processing a time-dependent measurement signal (d(n)) obtained from a pressure sensor (4a-4c) in a fluid containing system associated with a first pulse generator (3) and a second pulse generator (3'), wherein the pressure sensor (4a-4c) is arranged in the fluid containing system to detect a first pulse originating from the first pulse generator (3) and a second pulse originating from the second pulse generator (3'), said device comprising:

means (28) for receiving the measurement signal (d(n)), means (29) for obtaining a first pulse profile (u(n)) which is a predicted temporal signal profile of the first pulse, and means (29) for filtering the measurement signal (d(n)) in the time-domain, using the first pulse profile (u(n)), to essentially eliminate the first pulse while retaining the second pulse.

31. A method for processing a time-dependent measurement signal (d(n)) obtained from a pressure sensor (4a-4c) in a fluid containing system associated with a first pulse generator (3) and a second pulse generator (3'), wherein the pressure sensor (4a-4c) is arranged in the fluid containing system to detect a first pulse originating from the first pulse generator (3) and a second pulse originating from the second pulse generator (3'), said method comprising:

receiving the measurement signal (d(n)), obtaining a standard signal profile (u(n)) of the first pulse, and subtracting the standard signal profile (u(n)) from the measurement signal (d(n)) in the time-domain, wherein the standard signal profile (u(n)) has such an amplitude and phase that the first pulse is essentially eliminated and the second pulse is retained.

32. A device for processing a time-dependent measurement signal (d(n)) obtained from a pressure sensor (4a-4c) in a fluid containing system associated with a first pulse generator (3) and a second pulse generator (3'), wherein the pressure sensor (4a-4c) is arranged in the fluid containing system to detect a first pulse originating from the first pulse generator (3) and a second pulse originating from the second pulse generator (3"), said device comprising:

an input (28) for the measurement signal (d(n)), a signal processor (25a) connected to said input (28) and comprising a processing module (29) configured to obtain a standard signal profile (u(n)) of the first pulse, and to subtract the standard signal profile (u(n)) from the measurement signal (d(n)) in the time-domain, wherein the standard signal profile (u(n)) has such an amplitude and phase that the first pulse is essentially eliminated and the second pulse is retained.

End Appendix A

APPENDIX B

Brief Description of the Drawings

Embodiments of the inventive concepts will now be described in more detail with reference to the accompanying schematic drawings.

Figure 27:
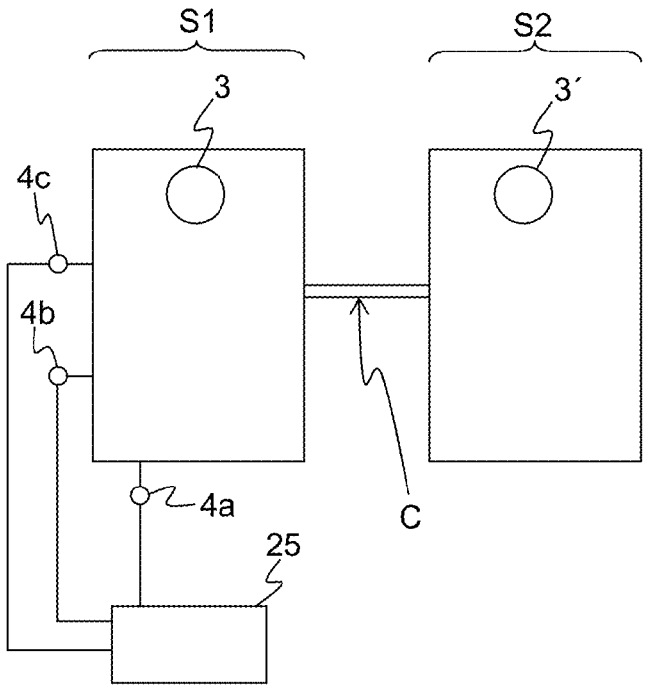
FIG. 27, as presented in Appendix B, is a schematic view of a general fluid arrangement in which the inventive concepts may be used for monitoring the integrity of a fluid connection.

FIG. 27 is a schematic view of a general fluid arrangement in which the inventive concepts may be used for monitoring the integrity of a fluid connection.

Figure 28:
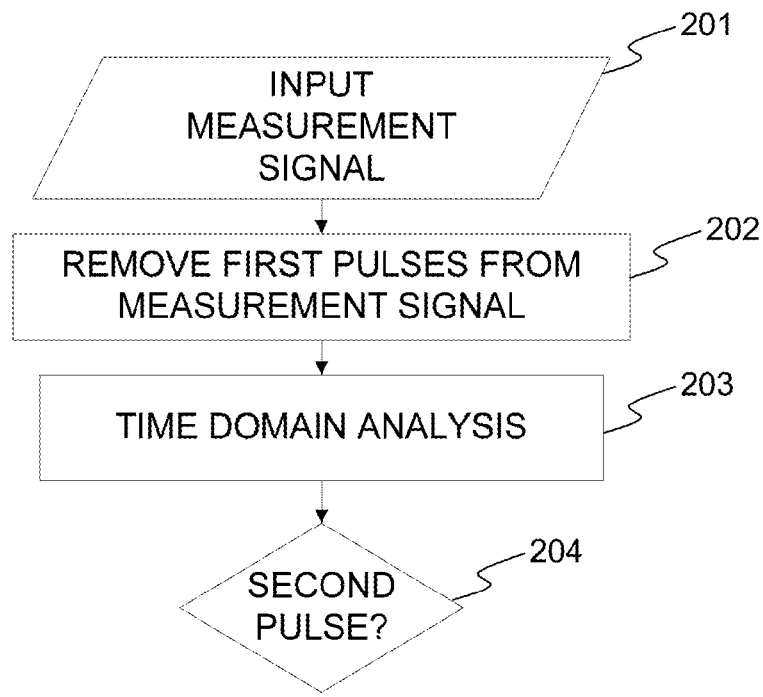
FIG. 28, as presented in Appendix B, is a flow chart of a monitoring process according to a first inventive concept.

FIG. 28 is a flow chart of a monitoring process according to a first inventive concept.

Figure 29:
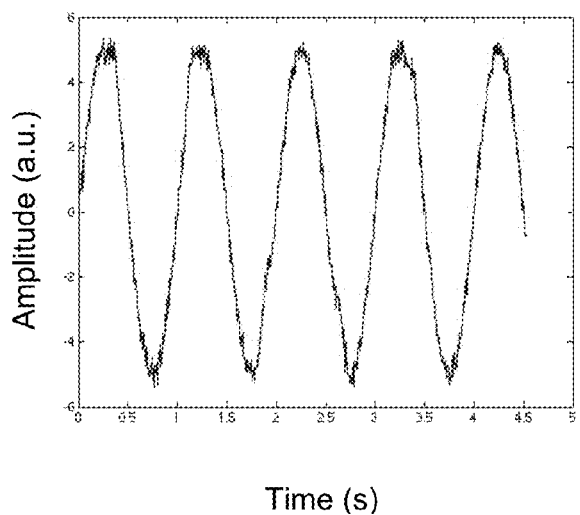
FIG. 29(a), as presented in Appendix B, is a plot of the measurement signal as a function of time, FIG. 29(b), as presented in Appendix B, is a plot of the measurement signal in FIG. 29(a) after filtering, and FIG. 29(c), as presented in Appendix B, illustrates a statistical dispersion measure calculated for a sequence of time windows in the signal in FIG. 29(b).
Figure 29:
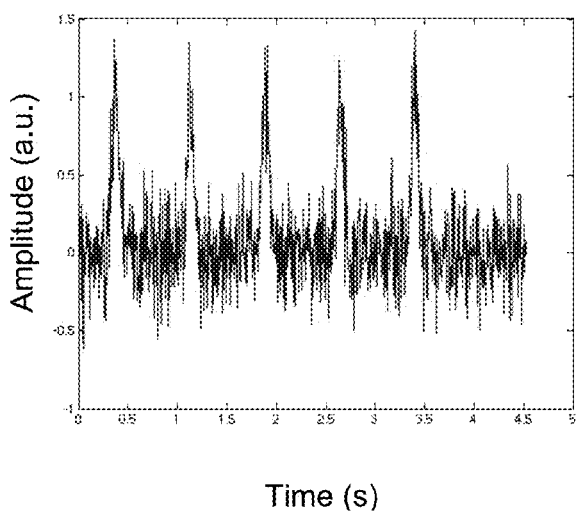
Figure 29:
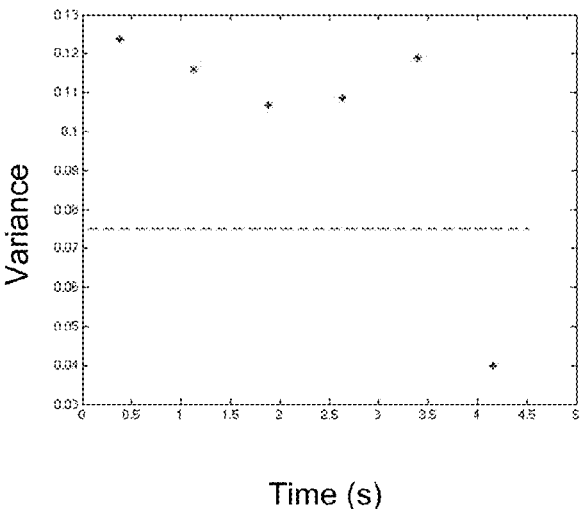

FIG. 29(a) is a plot of the measurement signal as a function of time, FIG. 29(b) is a plot of the measurement signal in FIG. 29(a) after filtering, and FIG. 29(c) illustrates a statistical dispersion measure calculated for a sequence of time windows in the signal in FIG. 29(b).

Figure 30:
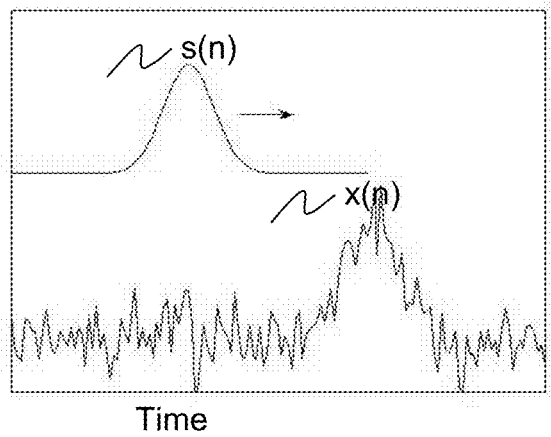
FIG. 30(a), as presented in Appendix B, illustrates a matching procedure between a measurement signal and a predicted signal profile, FIG. 30(b), as presented in Appendix B, illustrates the position of best match, and FIG. 30(c), as presented in Appendix B, is a correlation curve resulting from the matching procedure in FIG. 30(a).
Figure 30:
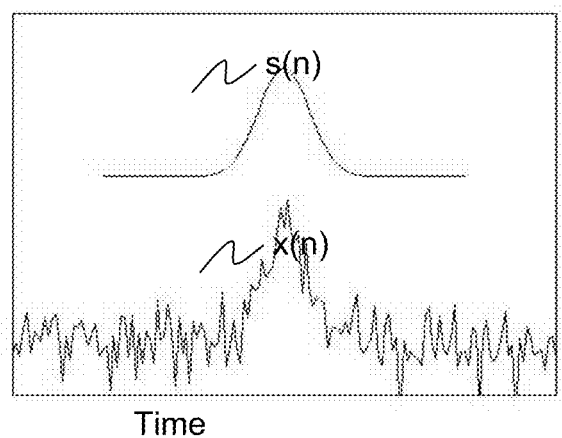
Figure 30:
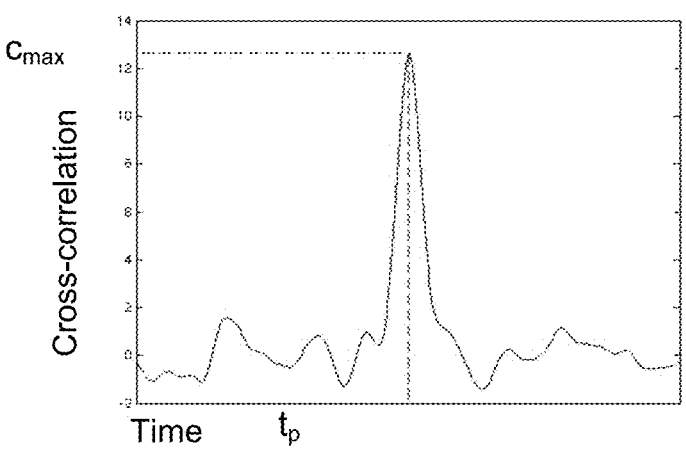

FIG. 30(a) illustrates a matching procedure between a measurement signal and a predicted signal profile, FIG. 30(b) illustrates the position of best match, and FIG. 30(c) is a correlation curve resulting from the matching procedure in FIG. 30(a).

Figure 31:
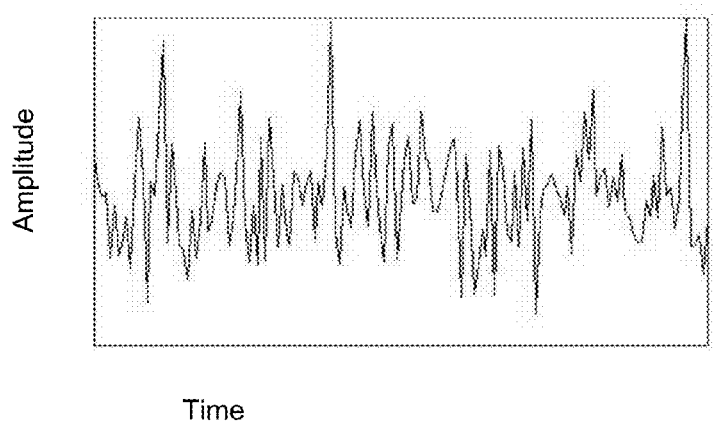
FIG. 31(a), as presented in Appendix B, is a plot of a signal segment containing a second pulse, and FIG. 31(b), as presented in Appendix B, is plot of an evaluation segment generated by averaging ten signal segments.
Figure 31:
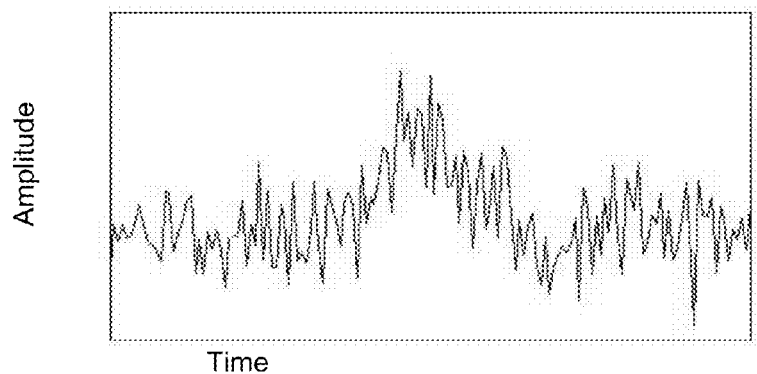

FIG. 31(a) is a plot of a signal segment containing a second pulse, and FIG. 31(b) is plot of an evaluation segment generated by averaging ten signal segments.

Figure 32:
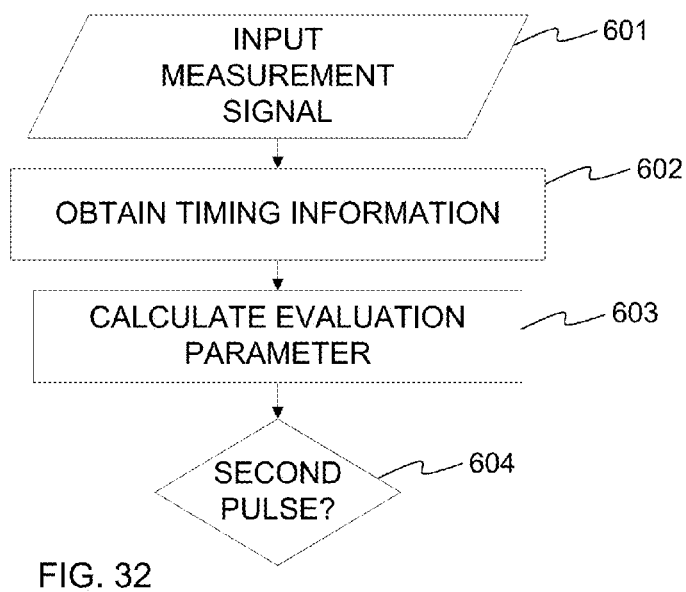
FIG. 32, as presented in Appendix B, is a flow chart of a monitoring process according to a second inventive concept.

FIG. 32 is a flow chart of a monitoring process according to a second inventive concept.

FIG. 33(a)-(d) illustrate processing of candidate pulses identified in a measurement signal.

FIG. 34 is a flow chart of part of a monitoring process according to the second inventive concept.

Figure 35:
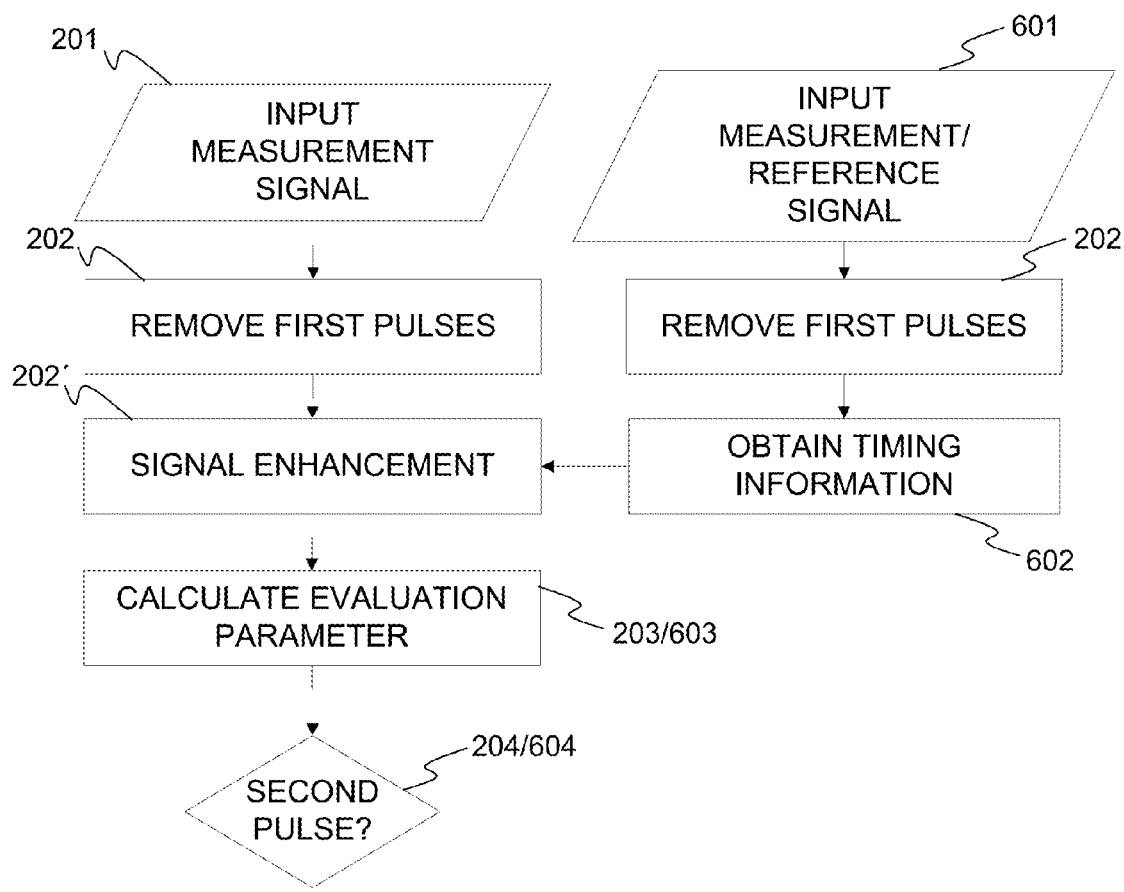
FIG. 35, as presented in Appendix B, is a flow chart of a monitoring process that combines the first and second inventive concepts.

FIG. 35 is a flow chart of a monitoring process that combines the first and second inventive concepts.

DETAILED DESCRIPTION OF INVENTIVE CONCEPTS AND EMBODIMENTS

In the following, inventive concepts and associated embodiments will be described with reference to fluid containing systems in general. Thereafter, the inventive concepts will be further exemplified in the context of systems for extracorporeal blood treatment.

Throughout the following description, like elements are designated by the same reference signs.

General

FIG. 27 illustrates a general fluid arrangement in which a fluid connection C is established between a first fluid containing system S1 and a second fluid containing system S2. The fluid connection C may or may not transfer fluid from one system to the other. A first pulse generator 3 is arranged to generate a series of pressure waves in the fluid within the first system S1, and a second pulse generator 3' is arranged to generate a series of pressure waves in the fluid within the second system S2. A pressure sensor 4c is arranged to measure the fluid pressure in the first system S1. As long as the fluid connection C is intact, pressure waves generated by the second pulse generator 3' will travel from the second system S2 to the first system S1, and thus second pulses originating from the second pulse generator 3' will be detected by the pressure sensor 4c in addition to first pulses originating from the first pulse generator 3. It is to be noted that either one of the first and second pulse generators 3, 3' may include more than one pulse-generating device. Further, any such pulse-generating device may or may not be part of the respective fluid containing system S1, S2.

The fluid arrangement of FIG. 27 further includes a surveillance device 25 which is connected to the pressure sensor 4c, and possibly to one or more further pressure sensors 4a, 4b, as indicated in FIG. 27. Thereby, the surveillance device 25 acquires one or more measurement signals that are time-dependent to provide a real time representation of the fluid pressure in the first system S1. The surveillance device 25 monitors the integrity of the fluid connection C, based on the principle that the presence of second pulses indicates that the fluid connection C is intact, whereas absence of second pulses indicates that the fluid connection C is compromised. The absence of second pulses may bring the surveillance device 25 to issue an alarm or warning signal, and/or alert a control system of the first or second fluid containing systems S1, S2 to take appropriate action.

The surveillance device 25 is thus configured to continuously process the time-dependent measurement signal(s) to determine whether second pulses are present or not. Typically, the determination involves analyzing the measurement signal(s), or a pre-processed version thereof, in the time domain to calculate a value of an evaluation parameter which is indicative of the presence or absence of second pulses in the measurement signal(s). Depending on implementation, the surveillance device 25 may use digital components or analog components, or a combination thereof, for receiving and processing the measurement signal(s).

In the context of the present disclosure, "absence" of a pulse may imply that the pulse has disappeared, or at least that it has decreased sufficiently in magnitude compared to the pulse deemed to be "present". The assessment of presence or absence may involve calculating an evaluation parameter value based on the measurement signal(s) and comparing the parameter value to a threshold value.

First Inventive Concept

FIG. 28 is a flow chart that illustrates steps of a monitoring process according to a first inventive concept. A measurement signal is received (step 201) and subjected to a filtering process (step 202) that essentially removes the first pulses from the measurement signal, while leaving at least part of the second pulses intact. The filtered measurement signal is then subjected to a time domain analysis (step 203), in which a value of an evaluation parameter is calculated based on signal values within a time window in the filtered measurement signal, which is denoted "evaluation segment" in the following. The calculation is typically designed such that the evaluation parameter represents the distribution of signal values within the evaluation segment. Based on the resulting value of the evaluation parameter, it is decided (step 204) whether the fluid connection is intact or not, typically by comparing the resulting value to a threshold value.

For continuous surveillance, a time sequence of evaluation parameter values is calculated based on a time sequence of evaluation segments obtained from the measurement signal. These evaluation segments may be overlapping or non-overlapping in time. In one embodiment, individual sections of the measurement signal are acquired, filtered and analyzed, one after the other. Each evaluation segment may correspond to one such section of the measurement signal; the time window is thus applied already when the measurement signal is acquired. In another embodiment, the measurement signal is continuously acquired and filtered, whereupon evaluation segments are extracted from the filtered signal and analyzed.

FIG. 29(a) shows an example of a time-dependent measurement signal containing first and second pulses with a relative magnitude of 10:1. The first and second pulses have a frequency of 1 Hz and 1.33 Hz, respectively. 29(b) shows the time-dependent measurement signal after removal of the first pulses, leaving only second pulses and noise. It should be noted that there is an absence of second pulses after about 4 seconds. FIG. 29(c) illustrates a variance measure calculated for a sequence of non-overlapping time windows in the filtered measurement signal in 29(b), each time window being about 0.75 seconds. Clearly, by using the variance measure as an evaluation parameter, it is possible to detect the absence of the second pulse at the time point of about 4 seconds. An exemplifying threshold value is indicated by a dotted line.

The first inventive concept has the potential of providing a comparatively robust measure of the integrity of the fluid connection C. By analyzing the temporal distribution of signal values within the evaluation segment, an improved tolerance to noise and disturbing signals may be obtained.

Furthermore, compared to techniques that rely on frequency domain analysis of the measurement signal for detecting the presence of second pulses, the first inventive concept may provide an improved tolerance to variations in the pulse repetition interval of the second pulse generator 3', since the first inventive concept relies on a time domain analysis. Such variations may occur, e.g., when the second pulse generator 3' is a human heart, and the second system S2 thus is the blood system of a human. Variations in heart rhythm (heart rate variability, HRV) will cause the peak from the heart in the frequency domain to be smeared out, making it harder to detect. In healthy subjects under calm conditions, HRV may be as large as 15%. Unhealthy subjects may suffer from severe heart conditions such as atrial fibrillation and supraventricular ectopic beating, which may lead to an HRV in excess of 20%, and ventricular ectopic beating, for which HRV may be in excess of 60%. These heart conditions are not uncommon among, e.g., dialysis patients.

As long as the time window is selected such that each evaluation segment contains at least one second pulse, the presence/absence of second pulses will affect the evaluation parameter, if properly chosen. A fixed-length time window may be used, with the length of the time window being chosen with respect to a maximum pulse repetition rate of the second pulse generator 3'. The length of the time window may be set by constraints in the second pulse generator 3' or by a selected performance limit of the surveillance method. Alternatively, the length of the time window and/or the location of the time window in the filtered measurement signal may be selected based on a predicted timing of the second pulse(s) to be detected. The acquisition and use of such a predicted timing ("timing information") will be further exemplified below with reference to the second inventive concept.

Still further, the time domain analysis according to the first inventive concept may allow for faster detection than a frequency domain analysis, since the former may have the ability to detect a single second pulse in the evaluation segment whereas the generation of a frequency spectrum requires a greater number of second pulses in the evaluation segment. Thus, frequency domain analysis may be associated with a greater time lag than time domain analysis.

The evaluation parameter may be calculated as a statistical dispersion measure of the signal values within the evaluation segment. Non-limiting examples of potentially useful statistical dispersion measures include standard deviation ($\sigma$), variance ($\sigma^2$), coefficient of variation ($\sigma/\mu$) and variance-to-mean ($\sigma^2/\mu$). Other examples include a sum of differences, e.g. given by $$\sum_{i=2}^{n} |x_i - x_{i-1}|,$$

or $$\sum_{i=1}^{n}\sum_{j=1}^{n} |x_i - x_j|,$$

or an energy measure, such as $$\sum_{i=1}^{n} x_i^2,$$

with n being the number of signal values x in the evaluation segment. Yet other examples include a measure based on a sum of absolute differences from an average value m, with the average value m being calculated for the signal values in the evaluation segment using any suitable function, such as arithmetic mean, geometric mean, median, etc. It is to be noted that all of the above suggested dispersion measures also include normalized and/or weighted variants thereof.

As an alternative or supplement to calculating a statistical dispersion measure, the evaluation parameter may result from a matching procedure, in which the evaluation segment is matched to one or more predicted signal profiles of a second pulse. Preferably, but not necessarily, each predicted signal profile represents a single second pulse. Typically, the matching procedure involves convolving or cross-correlating the evaluation segment and the predicted signal profile, and the evaluation parameter value is a resulting correlation value, typically the maximum correlation value.

A matching procedure based on cross-correlation is further exemplified in FIGS. 30(a)-30(c). The matching procedure is used to distinguish between the hypotheses $H_0: x(n)=w(n)$ $H_1: x(n)=s(n)+w(n)$ with x(n) being the evaluation segment, w(n) being an error signal representing disturbances introduced by noise/signal interference/measurement errors, etc, and s(n) being the predicted signal profile of the second pulse. If $H_1$ is deemed more likely than $H_0$, then a second pulse has been identified and the fluid connection C is deemed intact. If $H_0$ is deemed more likely than $H_1$, then a second pulse cannot be identified and the fluid connection C may be compromised.

FIG. 30(a) is a graph showing an example of a predicted signal profile s(n) and an evaluation segment x(n). In this particular example, the evaluation segment has a signal-to-noise ratio (SNR) of 4.8 dB, i.e. the energy of the signal profile s(n) is 3 times the energy of the error signal w(n). During the cross-correlation, the signal profile s(n) is slid in a number of time steps along the time axis, as indicated by arrow in FIG. 30(a), and the integral of the product s(n)·x(n) is calculated for each time step. The cross-correlation thus results in a time sequence of correlation values, with the maximum correlation value indicating the time point of best match between x(n) and s(n). FIG. 30(b) illustrates the relative position between x(n) and s(n) at the time point for best match, and FIG. 30(c) illustrates the resulting correlation values as a function of said time steps. The magnitude of the maximum correlation value, optionally calculated as a weighted average within a range around the maximum correlation value ($c_{max}$), may thus be used to distinguish between the above hypotheses.

As indicated in FIG. 30(c), the matching procedure not only identifies the presence of a second pulse, it also provides an indication of the location of the second pulse in the evaluation segment, given by the time point ($t_p$) for the maximum correlation value ($c_{max}$). This time point may be used to assess the reliability of the determined maximum correlation value, by comparing this time point to a predicted time point. Such a predicted time point may be obtained from aforesaid timing information, as will be further explained below in relation to the second inventive concept.

The predicted signal profile may be generated as an average of a number of recordings of second pulses. For example, it may be generated by averaging a number of evaluation segments, before and/or during the monitoring process.

To improve the signal quality of the predicted profile, with or without averaging, the measurement signal may be acquired while the first pulse generator is stopped, whereby the measurement signal is free of first pulses. Thus, the first pulse generator may be intermittently stopped during the monitoring process for calculation of an updated signal profile of the second pulses.

In another variant, the predicted signal profile is obtained from one or more reference signals originating from a reference pressure sensor (e.g. any one of pressure sensors 4a-4c in FIG. 27) in the first system. Such a reference pressure sensor is suitably arranged to detect second pulses even if the fluid connection is compromised, e.g. via a second fluid connection between the first and second fluid containing systems. The reference pressure sensor may be installed to be isolated from the first pulses, such that the reference signal is essentially free of first pulses. Alternatively, if the reference signal includes both first and second pulses, the reference signal may be subjected to a filtering process (e.g. according to step 202 in FIG. 28) to remove the first pulses while leaving the second pulses intact in the reference signal. An example of such a reference pressure sensor is an arterial pressure sensor in an extracorporeal blood flow circuit. In such an extracorporeal blood flow circuit, the measurement signal(s) may originate from one or more venous pressure sensors, e.g. if the monitoring process aims at monitoring the integrity of the venous-side fluid connection between the extracorporeal blood flow circuit and a patient.

In one specific implementation, the reference signal is obtained continuously or intermittently during the monitoring process, and the predicted signal profile is continuously or intermittently calculated based on the reference signal. Thus, in the context of the above-mentioned extracorporeal blood flow circuit, the integrity of the venous-side fluid connection may be monitored by continuously matching evaluation segments from the venous pressure sensor against a predicted signal profile obtained from the arterial pressure sensor. It is even conceivable that the predicted signal profile is updated for each evaluation segment (denoted "synchronous monitoring" in the following). The matching procedure may benefit from the use of timing information, as will be further explained below in relation to the second inventive concept. Alternatively, the predicted signal profile may be pre-generated, e.g. by averaging recordings of second pulses from a number of fluid arrangements, similar to the one that is being monitored (cf. FIG. 27). Optionally, such a pre-generated signal profile may be adapted to specifics of the fluid arrangement to be monitored, by applying a mathematical model taking into account arrangement-specific parameters, such a type of fluid connection, flow rate, fluid characteristics, etc. Alternatively, the predicted signal profile may be obtained entirely by mathematical modelling based on arrangement-specific parameters. According to yet another alternative, a standard profile is used as predicted signal profile, e.g. a bell-shaped function such as a Gaussian distribution function.

In order to improve the detection of second pulses, it is conceivable to subject the filtered measurement signal/evaluation segment to a signal enhancement process, which removes high-frequency components (cf. error signal w(n)), before calculation of the evaluation parameter value. Such a signal enhancement process may involve subjecting the filtered measurement signal/evaluation segment to a low-pass filtering. However, a more significant improvement in SNR of the evaluation segment may be achieved by averaging several consecutive second pulses in the filtered measurement signal, again based on the above-mentioned predicted timing of the second pulse(s) (i.e. timing information). Such a signal enhancement process would thus involve using the predicted timing to identify a set of second pulse segments in the filtered measurement signal, aligning the second pulse segments in the time domain based on the predicted timing, and generating an average representation by summing the aligned signal values for each time value in the time domain. Optionally, the average representation is normalized by the number of second pulse segments to generate a true average. The average representation may then be used as the above-mentioned evaluation segment, or the evaluation segment may be extracted from a time window within the average representation.

The signal enhancement process is further exemplified in FIGS. 31(a)-31(b). FIG. 31(a) is a time domain representation of a filtered measurement signal x(n)=s(n)+w(n) with a SNR of −9 dB, i.e. the energy of the error signal w(n) is 8 times the energy of the signal profile s(n), making time domain analysis for detection of the second pulse difficult, if not impossible. FIG. 31(b) is a time domain representation after averaging of 10 different second pulse segments similar to the one in FIG. 31(a). Clearly, the SNR has been improved significantly, allowing a second pulse to be detected using time domain analysis.

It is to be understood that the monitoring process of FIG. 28 may operate on more than one measurement signal, if the fluid arrangement to be monitored includes more than one pressure sensor (cf. 4a, 4b in FIG. 27). In such a configuration, the above-described signal enhancement process may involve using aforesaid timing information to identify and average second pulse segments from at least two filtered measurement signals originating from different pressure sensors. Thus, the second pulse segments may be extracted from plural time windows in each measurement signal, and/or from one or more time windows in different measurement signals.

The filtering process according to step 202 in FIG. 28 aims at removing the first pulses from the measurement signal to such an extent that the second pulses can be detected by the subsequent time domain analysis (step 203). For example, a comb filter and/or a combination of band-stop or notch filters, typically cascade coupled, may be operated on the measurement signal to block out all frequency components originating from the first pulse generator 3. Alternatively, such blocking may be achieved by the use of one or more adaptive filters and notch-equivalent filters, e.g. as disclosed in aforesaid WO 97/10013. In yet another alternative embodiment, the measurement signal is processed in the time domain to cancel the first pulses. In such an embodiment, a standard signal profile of the first pulses may be obtained, which is then subtracted from the measurement signal at suitable amplitude and phase. The phase is indicated by phase information which may be obtained from a signal generated by a phase sensor coupled to the first pulse generator 3, or from a control signal for the first pulse generator 3. The standard signal profile may be obtained from one or more of the pressure sensors 4a-4c in the first fluid containing circuit S1, suitably by identifying and averaging a set of first pulse segments in the measurement signal(s) similarly to the above-mentioned signal enhancement process. The standard signal profile may or may not be updated intermittently during the monitoring process. Alternatively, a predetermined standard signal profile is used, which optionally may be modified according to a mathematical model accounting for wear in the first pulse generator, fluid flow rates, tubing dimensions, speed of sound in the fluid, etc. It should be noted that by filtering the measurement signal in the time domain, instead of the frequency domain, it is possible to eliminate the first pulses and still retain the second pulses, even if the first and second pulses overlap in the frequency domain.

Second Inventive Concept

FIG. 32 is a flow chart that illustrates steps of a monitoring process according to a second inventive concept. In this process, a measurement signal is received (step 601) and timing information is obtained, from the measurement signal or otherwise (step 602). The timing information is indicative of the timing of second pulses in the measurement signal. Subsequently, the measurement signal is processed (step 603) based on the timing information, to calculate a value of an evaluation parameter which is indicative of the presence or absence of a second pulse in the measurement signal. Based on the resulting value of the evaluation parameter, it is decided (step 604) whether the fluid connection is intact or not, typically by comparing the resulting value to a threshold value.

Thus, in the second inventive concept, timing information indicates the expected position of a second pulse in the measurement signal. This additional information may allow the second pulse to be identified from other types of signal features, e.g. different/simpler evaluation parameters, and/or it may allow for an increased reliability in detecting presence/absence of second pulses.

Furthermore, as explained above, the provision of timing information allows for signal enhancement by identifying and averaging second pulse segments in one or more measurement signals. The signal enhancement may increase the SNR of the measurement signal, allowing for the use of a rudimentary measure as evaluation parameter, such as signal amplitude, local maximum, local average, etc. This may serve to improve the processing speed and/or allow for less sophisticated detection equipment.

It is to be understood that the second inventive concept can be combined with any of the features of the first inventive concept. For example, the measurement signal may be filtered to remove first pulses, and the evaluation parameter may be calculated for an evaluation segment given by signal values within a time window in the filtered measurement signal. Also, any one of the evaluation parameters suggested in relation to the first inventive concept is equally applicable to the second inventive concept. It is to be noted, however, that the filtering of the measurement signal is not an essential feature of the second inventive concept, since the use of timing information may allow second pulses to be detected in the measurement signal even in the presence of first pulses.

The second inventive concept may also improve the detection speed, since the timing information may provide a predicted time point for the second pulse in the measurement signal/filtered measurement signal/evaluation segment. Thereby, the number of signal values that need to be processed for calculation of the evaluation parameter value may be reduced. For example, the aforesaid matching procedure may be simplified, since the correlation between the predicted signal profile and the evaluation segment need only be calculated for the predicted time point, or a confined time range around this predicted time point. Correspondingly, the calculation of a statistical dispersion measure or the above-mentioned rudimentary measure may be simplified, since the provision of timing information makes it possible to reduce the size of the time window for extracting the evaluation segment, while still ensuring that each evaluation segment includes at least one second pulse. For example, the size of the time window may be reduced if the timing information indicates a shortened pulse interval between the second pulses, and/or the time window may be centred on the predicted time point of each second pulse.

Still further, the second inventive concept allows for assessing the reliability of a calculated evaluation parameter value, by comparing a time point associated with the evaluation parameter value with a predicted time point given by the timing information. For example, the time point for a maximum correlation value obtained in the aforesaid matching procedure may be compared with a predicted time point for a second pulse. If these time points deviate too much, the monitoring process may determine that a second pulse is absent, even though the magnitude of the correlation value might indicate presence of a second pulse.

The timing information may be obtained in any one of a plurality of different ways. For example, the timing information may be extracted from the output signal of a pulse sensor coupled to the second fluid containing system. The output signal may indicate individual second pulses or an average time between second pulses. In either case, a predicted time point for a second pulse in the measurement signal can be calculated based on the output signal of the pulse sensor and a known difference in arrival time between the pulse sensor and the pressure sensor(s) that generates the measurement signal(s). The pulse sensor may sense the pressure waves that are generated in the fluid by second pulse generator, or it may directly reflect the pulse generation process in the second pulse generator, e.g. via a control signal for the second pulse generator or a pulse rate meter mechanically coupled to the second pulse generator. In one application, to be further exemplified below, the second fluid containing system is a blood system of a human, and the pulse generator is a human heart. In such an application, the timing information may be provided by any conventional pulse sensor such as a pulse watch, a pulse oximeter, an electrocardiograph, etc.

Alternatively, the timing information may be obtained based on the relative timing of previously detected second pulses in the measurement signal, e.g. given by the time points associated with previously calculated evaluation parameter values. For example, the time difference between the two most recently detected second pulses may be used to predict the time point for subsequent second pulse(s).

Alternatively, the timing information may be obtained from one or more reference signals originating from a reference pressure sensor in the first system. Such a reference pressure sensor is suitably arranged to detect second pulses even if the fluid connection is compromised, e.g. via a second fluid connection between the first and second fluid containing systems.

An example of such a reference pressure sensor is an arterial pressure sensor in an extracorporeal blood flow circuit. In such an extracorporeal blood flow circuit, the measurement signal(s) may originate from one or more venous pressure sensors, e.g. if the monitoring process aims at monitoring the integrity of the venous-side fluid connection between the extracorporeal blood flow circuit and a patient. The reference signal may be processed for detection of at least one second pulse, using any suitable technique, including the time domain techniques disclosed herein. The time point of the detected second pulse in the reference signal can then be converted to a predicted time point in the measurement signal/filtered measurement signal/evaluation segment using a known/measured difference in pulse arrival/transit time between the reference sensor and the pressure sensor(s) used for monitoring. Thus, in one embodiment, the difference in transit time is given by a fixed and predefined value.

In another embodiment, the difference in transit time between a blood line on the arterial side and a blood line on the venous side in the extracorporeal blood flow circuit is determined based on the actual arterial and venous pressures (absolute, relative, or average), which may be derived from any suitable sensor in the extracorporeal blood flow circuit (including the venous and arterial pressure sensors). The transit time decreases if the pressure increases, i.e., high pressure equals short transit time. During operation of the extracorporeal blood flow circuit, the venous pressure should be higher than the arterial pressure, and thus the transit time should be shorter in the venous blood line compared to the transit time in the arterial blood line. The difference in transit time may be determined based on, e.g., a physical model or a look-up table. The model/table may not only include information about pressure (absolute, relative, or average), but also information about material (elasticity, plasticity, etc), geometry (length, diameter, wall thickness, etc), temperature (both fluids and ambient temperature), mechanical factors (clamp, tension, actuators, kinking/occlusion, etc), fluid properties (viscosity, water/blood, chemical composition, etc), etc. The thus-determined difference in transit time may then be used to relate a time point of a detected second pulse in the reference signal from the arterial pressure sensor to a predicted time point in the measurement signal/filtered measurement signal/ evaluation segment originating from the venous pressure sensor.

In a variant, an improved estimation of the timing information may be obtained by aligning and adding the filtered measurement signal/evaluation segment (derived from the venous pressure signal) with a correspondingly filtered reference signal (derived from the arterial pressure signal), to thereby calculate an average time-dependent signal with improved SNR. The aligning may be based on the aforesaid difference in transit time, given by the actual arterial and venous pressures (absolute, relative, or average). By identifying one or more second pulse(s) in the average time-dependent signal, an improved estimation of the timing information is obtained.

Alternatively or additionally, to potentially improve the precision of the timing information, the timing information may be obtained by intermittently stopping the first pulse generator, while identifying at least one second pulse in the reference signal or the measurement signal.

Optionally, the process of obtaining timing information based on an identified second pulse, be it in the reference signal or the measurement signal, may involve validating the identified second pulse (a candidate pulse) against a temporal criterion. Such a temporal criterion may, e.g., indicate an upper limit and/or a lower limit for the time difference between the time point for the candidate pulse and one or more previously identified (and suitably validated) second pulses. These limits may be fixed, or they may be set dynamically in relation to a preceding time difference. Any candidate pulse that violates the temporal criterion may be removed/ discarded from use in obtaining the timing information.

In yet another alternative, the timing information is obtained from a measurement signal using an iterative approach. In this iterative approach, the measurement signal is processed to calculate a time-sequence of evaluation parameter values, e.g. based on the first inventive concept. These evaluation parameter values identify a sequence of candidate pulses and associated candidate time points, which is validated against a temporal criterion. Such a temporal criterion may, e.g., indicate an upper limit and/or a lower limit for the time difference between the candidate time points. The temporal criterion may be given by constraints in the second pulse generator 3'. Any candidate time points that violate the temporal criterion may be removed/discarded, and the timing information may be obtained from the remaining time points.

Different validation methods may be used depending on the availability of previous timing information, i.e. information about time points of preceding second pulses. Such previous timing information may be given by any one of the methods described in the foregoing, or resulting from a previous iteration of the iterative approach.

FIG. 33(*a*) illustrates a sequence of candidate pulses (denoted by X), as well as a sequence of preceding second pulses (denoted by Y), laid out on a time axis. In a first validation step, predicted time points (arrows 1 in FIG. 33(*b*)) are calculated based on the previous timing information (e.g. second pulses Y). In a second validation step, a first temporal criterion is applied to remove/discard any candidate pulses that lie too far from the predicted time points, as also shown in FIG. 33(*b*). In a third validation step, a second temporal criterion is applied to retain only the candidate pulse with the largest evaluation parameter value among any candidate pulses that lie too close to each other, as shown in FIG. 33(*c*).

A different validation method may be used if previous timing information is not available. FIG. 34 is a flow chart for such a validation method. The initial step 801 of identifying candidate pulses is followed by a first validation step 802, in which a first temporal criterion is applied to retain only the candidate pulse with the largest evaluation parameter value among any candidate pulses that lie too close to each other. FIG. 33(*d*) shows an exemplifying result of applying the first validation step 802 to the sequence of candidate pulses in FIG. 33(*a*). Then, in step 803, different combinations of the remaining candidate pulses are formed. In step 804, an average representation is calculated for each such combination, by aligning and summing corresponding signal segments of the measurement signal/filtered measurement signal. The combinations may be formed based on a second temporal criterion that defines an upper limit and/or a lower limit for the time difference between the candidate pulses. In a second validation step 805, an evaluation parameter value is calculated for each such average representation, and the maximum evaluation parameter value is extracted. Finally, in step 806, it is decided whether the fluid connection is intact or not, by comparing the maximum evaluation parameter value to a threshold value. If the maximum evaluation parameter value exceeds the threshold value, it may be concluded that a second pulse is present and that the fluid connection is intact. It may be noted that there is no need to explicitly extract the timing information in the validation method in FIG. 34, since the use of the timing information is embedded in the final step 806 of determining the integrity of the fluid connection.

It should also be noted that different evaluation parameters and/or threshold values may be used in steps 801 and 806. It is also conceivable to use a combination of two or more of the above alternative methods for obtaining the timing information.

FIG. 35 is a flow chart of an embodiment that combines features of the first and second inventive concepts. Specifically, a measurement signal is obtained and filtered according to steps 201 and 202 of the first inventive concept. Then, in step 202', the filtered measurement signal is processed for signal enhancement, based on timing information. As discussed above in relation to FIG. 31, step 202' typically involves identifying, aligning and summing a set of second pulse segments in the filtered measurement signal, to create an average signal representation. An evaluation parameter value is then calculated based on the enhanced signal representation according to step 203/603 of the first/second inventive concept, and it is decided whether the fluid connection is intact or not (steps 204/604). The method also involves receiving a measurement signal (which may be the same measurement signal as in step 201, or the aforesaid reference signal) according to step 601 of the second inventive concept. Then, the measurement/reference signal is filtered to remove the first pulse, if required, according to step 202 of the first inventive concept. Finally, the timing information is obtained according to step 602 of the second inventive concept.

Combinations of Monitoring Techniques

As explained in the foregoing, the technique for monitoring the integrity of the fluid connection can be based on either of the first and second inventive concepts, or a combination thereof. It is also possible to combine such an inventive monitoring technique with one or more conventional monitoring techniques, which e.g. involve the use of an air detector, or a comparison of average pressure levels with threshold values as described by way of introduction. Other conventional monitoring techniques are disclosed in aforesaid WO 97/10013 and US2005/0010118.

It might also be desirable to combine the inventive monitoring techniques with other techniques that are specially designed to handle adverse operating conditions. One such operating condition may arise when the first and second pulses overlap in the frequency domain. As discussed above in relation to step 202 of FIG. 28, such an operating condition could be handled by filtering the measurement signal in the time domain. However, the monitoring precision may be increased further by combining the inventive monitoring technique with a phase-locking technique or a beating detection method, to be described in the following.

The phase-locking technique involves controlling the first/second pulse generator 3, 3' so as to synchronize the pulse rate of the first and second pulse generators 3, 3' while applying a phase difference between the first and second pulses. Thereby, the first and second pulses will be separated in time, and can be detected using the time domain analysis according to the first and/or second inventive concepts. The phase difference may be approximately 180°, since this may maximize the separation of the first and second pulses in the time domain. The phase-locking technique may be activated when it is detected that the frequency of the second pulse generator approaches a frequency of the first pulse generator, or vice versa.

The beating detection method is an alternative or complementary monitoring technique which involves evaluating the presence or absence of a beating signal in the measurement signal to determine the integrity of the fluid connection. The beating signal manifests itself as an amplitude modulation of the measurement signal and is formed by interference between pressure waves generated by the first pulse generator and pressure waves generated by the second pulse generator. Instead of trying to identify second pulses in the measurement signal, the presence of second pulses is identified via the secondary effect of beating. Generally, beating is a phenomenon which is especially noticeable when two signals with closely spaced frequencies are added together. Thus, the beating signal detection is inherently well-suited to be used when the first and second pulses are closely spaced in the frequency domain. The beating signal may or may not be detected by analysing the measurement signal in the time domain. Suitably, the beating detection involves obtaining one or more specific frequencies related to the first pulse generator, and creating at least one filtered measurement signal in which all but one of said specific frequencies are removed. The beating signal may then be detected by determining an envelope of the filtered measurement signal. The beating detection method is the subject of Applicant's PCT publication WO2009/127683, which is incorporated herein in its entirety by reference.

It is to be understood that in any one of the above combinations, the different monitoring techniques may be carried out in series, in any order, or in parallel.

Performance Improvements

The performance of the different methods for monitoring the integrity of a fluid connection as described herein may be improved by applying any of the following variations.

Hypothesis Test

The determination of the integrity of the fluid connection between the first and second fluid containing systems could be represented by a hypothesis test. In this hypothesis test, the above-mentioned evaluation parameter value $\beta$ is compared to a threshold. The output of the hypothesis is a decision, which may be "intact fluid connection" ($H_1$) if $\beta > \gamma_1$, "compromised fluid connection" ($H_0$) if $\beta < \gamma_0$, or "uncertain decision" if $\gamma_0 \leq \beta \leq \gamma_1$, wherein $\gamma_0$ and $\gamma_1$ are different thresholds.

Magnitude Dependent Monitoring Technique

The monitoring technique may be dynamically adjusted based on the magnitude of the first and/or second pulses in the measurement signal and/or in the reference signal. The dynamic adjustment may affect the process for obtaining timing information and/or the process for obtaining the parameter value based on the measurement signal.

For example, if the magnitude (e.g. amplitude) of second pulses in the reference signal are found to be smaller than the magnitude (e.g. amplitude) of second pulses in the measurement signal, or smaller than a predetermined absolute limit, the timing information may be obtained based on the measurement signal, whereas the timing information otherwise is obtained based on the reference signal (or vice versa). Thus, with reference to FIG. 35, step 601 is adjusted based on the magnitude of second pulses.

In another example, if the magnitude (amplitude) of the second pulses in the reference signal again are found to be too small, the monitoring method may switch to another method for detecting presence or absence of second pulses in the measurement signal, e.g. a method that operates without timing information (e.g. by omitting steps 601, 602, 202 and 202' in FIG. 35).

In the above examples, if the magnitude of first and second pulses are covariant entities, the dynamic adjustment may alternatively be based on the magnitude of first pulses, or the magnitude of a combination of first and second pulses.

Monitoring Technique Based on Patient Data Records

When the second fluid containing system (S2 in FIG. 27) is a blood system of a patient, the monitoring method may be configured to access and use patient-specific information, i.e. existing data records for the patient, e.g. obtained in earlier treatments of the same patient. The patient-specific information may be stored in an internal memory of the surveillance device (25 in FIG. 27), on an external memory which is made accessible to the surveillance device, or on a patient card where the information is e.g. transmitted wirelessly to the surveillance device, e.g. by RFID (Radio Frequency IDentification). For example, the surveillance device may compare the filtered measurement signal, or a parameter derived therefrom, to the patient-specific information. If large differences are identified, a warning may be issued and/or the monitoring technique may be modified (or chosen according to a predetermined table). Furthermore, the patient-specific information may be used by the surveillance device to optimize the monitoring technique by e.g. determining personal threshold values for use in the foregoing algorithms/processes. The patient-specific information may also be used by the surveillance device to determine if an alternative monitoring technique or combinations of monitoring techniques should be used.

Use of Information from Regular Stops of First Pulse Generator

In one embodiment, the first pulse generator is regularly (intermittently or periodically) stopped, and the measurement signal and/or reference signal is analysed for determination of amplitude, frequency and phase of second pulses. This resulting information may then be used to achieve detection by the above-mentioned phase-locking technique.

Alternatively or additionally, if the magnitude (e.g. amplitude) of the second pulse(s) detected during such a stop is smaller than a certain limit (chosen with a margin for safe detection), an alert on "uncertain detection" may be issued. Alternatively, if the magnitude is smaller than another limit, the first pulse generator may be actively controlled to be stopped at specific time intervals, where the information obtained during each stop may be used to modify the monitoring technique. For example, the thus-obtained information may be used to change (or add) threshold values in the foregoing algorithms/processes, or to determine if an alternative monitoring technique or combinations of monitoring techniques should be used. In another example, if the thus-obtained information indicates the pulse rate of second pulses, a dedicated bandpass filter (e.g. centred on the thus-obtained pulse rate) may be operated on the measurement signal/filtered measurement signal/evaluation segment to further improve the input to the process for obtaining timing information (cf. step 602 in FIG. 32) and/or the process for obtaining the parameter value based on the measurement signal (cf. step 203/603 in FIGS. 28 and 35). In one embodiment, such a bandpass filter is applied if the rates of first and second pulses are found to differ by more than a certain limit, e.g. about 10%.

In another embodiment, the first pulse generator is selectively controlled so as to reduce the flow rate through the fluid arrangement. By reducing the flow rate, it is possible to accept a longer response time of the monitoring process to a fault condition, while such a longer response time may serve to improve the precision of the monitoring process in detecting fault conditions.

The invention has mainly been described above with reference to a few embodiments. However, as is readily appreciated by a person skilled in the art, other embodiments than the ones disclosed above are equally possible within the scope and spirit of the invention, which is defined and limited only by the appended patent "items".

The inventive monitoring techniques are applicable when the measurement signal originates from a pressure sensor arranged to sense the pressure in an extracorporeal blood flow circuit. In such an embodiment, the first fluid containing system (S1) is the extracorporeal blood flow circuit, the second fluid containing system (S2) is human blood system, and the fluid connection (C) may be formed by a connection between an access device and a blood vessel access. The first pulses may originate from the pumping device in the extracorporeal blood flow circuit (and/or any other pulse generator within or associated with the extracorporeal blood flow circuit), and the second pulses may originate from the human heart, and the integrity of the fluid connection is determined by applying the first and/or second inventive concepts to detect the presence/absence of the second pulses in the measurement signal.

The pressure (measurement) signal may originate from any conceivable type of pressure sensor, e.g. operating by resistive, capacitive, inductive, magnetic or optical sensing, and using one or more diaphragms, bellows, Bourdon tubes, piezo-electrical components, semiconductor components, strain gauges, resonant wires, etc.

Further, the disclosed embodiments are applicable for surveillance of all types of extracorporeal blood flow circuits in which blood is taken from a patient's circulation to have a process applied to it before it is returned to the circulation. Such blood flow circuits include hemodialysis, hemofiltration, hemodiafiltration, plasmapheresis, apheresis, extracorporeal membrane oxygenation, assisted blood circulation, and extracorporeal liver support/dialysis.

Further, the inventive monitoring techniques are applicable to any type of pumping device that generates pressure pulses in the first fluid containing system, not only rotary peristaltic pumps as disclosed above, but also other types of positive displacement pumps, such as linear peristaltic pumps, diaphragm pumps, as well as centrifugal pumps.

Still further, the inventive monitoring techniques are applicable also for monitoring the integrity of the fluid connection between the blood vessel access and the arterial needle based on a measurement signal from one or more arterial pressure sensors. Such a monitoring technique may provide a faster detection of malfunction than the conventional air detector, and more reliable detection of malfunction than conventional comparison of average pressure levels to threshold values. In such an application, the aforesaid reference signal may be derived from one or more venous pressure sensors in the extracorporeal blood flow circuit.

Also, it is to be understood that the monitoring technique is equally applicable to single-needle dialysis.

The inventive monitoring techniques are also applicable when the measurement signal originates from a pressure sensor arranged to sense the pressure in the human blood system. In such an embodiment, the first fluid containing system (S1) is the human blood system, the second fluid containing system (S2) is the extracorporeal blood flow circuit, and the fluid connection (C) may be formed by a connection between an access device and a blood vessel access. The first pulses thus originate from the human heart, and the second pulses originate from the pumping device in the extracorporeal blood flow circuit (and/or any other pulse generator within or associated with the extracorporeal blood flow circuit), and the integrity of the fluid connection is determined by applying the first and/or second inventive concepts to detect the presence/absence of the second pulses in the measurement signal.

The above-described inventive concepts may also be applicable to monitoring the integrity of fluid connections for transferring other liquids than blood. Likewise, the fluid connections need not be provided in relation to a human, but could be provided in relation to any other type of fluid containing system.

In one example, the fluid connection is provided between a blood processing circuit and a container/machine, wherein blood is pumped from one container/machine through a blood processing device in the blood processing circuit and back to the container/machine, or to another container/machine downstream of the blood processing device. The blood processing device could be any known device configured to modify and/or analyse the blood.

In a further example, the fluid connection is provided between a dialyser and a reprocessing system, which reprocesses the dialyser by pumping water, optionally together with suitable chemicals through the dialyser. An example of a dialyser reprocessing system is known from US2005/0051472.

In another example, the fluid connection is provided between a dialysate supply and a dialysate regeneration system, which circulates dialysate from the dialysate supply through a dialysate regeneration device and back to the supply. An example of a dialysate regeneration device is known from WO 05/062973.

In yet another example, the fluid connection is provided in an arrangement for priming an extracorporeal blood flow circuit by pumping a priming fluid from a supply via the blood flow circuit to a dialyser. The priming fluid may e.g. be dialysis solution, saline, purified water, etc.

In a still further example, the fluid connection is provided in an arrangement for cleaning and disinfecting the dialysis solution flow path of a dialysis machine, which pumps a cleaning fluid via a flow path to a dialyser/dialyser tubing. The cleaning fluid may e.g. be hot water, a chemical solution, etc.

In a further example, the fluid connection is provided in an arrangement for purifying water, which pumps water from a supply through a purifying device. The purifying device may use any known water purification technique, e.g. reverse osmosis, deionization or carbon absorption.

In another example, the fluid connection is provided in an arrangement for providing purified water to a dialysis machine, e.g. to be used in the preparation of dialysis solution therein.

In all of these examples, and in other applications related to medical treatment of human or animal patients, it may be vital to monitor the integrity of the fluid connection. Such monitoring can be accomplished according to the inventive concepts disclosed herein.

APPENDIX B

Items

1. A method for monitoring the integrity of a fluid connection (C) between first and second fluid containing systems (S1, S2) based on at least one time-dependent measurement signal from at least one pressure sensor (4a-4c) in the first fluid containing system (S1), wherein the first fluid containing system (S1) comprises a first pulse generator (3), and the second fluid containing system (S2) comprises a second pulse generator (3"), and wherein said at least one pressure sensor (4a-4c) is arranged to detect first pulses originating from the first pulse generator (3) and second pulses originating from the second pulse generator (3"), said method comprising:

receiving said at least one measurement signal;

generating, based on said at least one measurement signal, a time-dependent monitoring signal in which the first pulses are essentially eliminated;

calculating a parameter value based on signal values within a time window in the monitoring signal, the parameter value representing a distribution of the signal values; and determining the integrity of the fluid connection based at least partly on the parameter value.

2. The method of item 1, wherein said calculating comprises: calculating the parameter value as a statistical dispersion measure of the signal values within the time window.

3. The method of item 2, wherein the statistical dispersion measure includes at least one of: a standard deviation, a variance, a coefficient of variation, a sum of differences, an energy, a power, a sum of absolute deviations from an average value, and an average of absolute differences from an average value.

4. The method of item 1, wherein said calculating comprises: matching the signal values within the time window to a predicted temporal signal profile of a second pulse.

5. The method of item 4, wherein the parameter value is a correlation value resulting from said matching.

6. The method of items 4 or 5, wherein said calculating comprises: calculating a cross-correlation between the signal values within the time window and the predicted temporal signal profile; and identifying a maximum correlation value in the cross-correlation; wherein said determining comprises: comparing the maximum correlation value to a threshold value.

7. The method of item 6, wherein said calculating comprises: obtaining a time point of the maximum correlation value, and validating the maximum correlation value by comparing the time point to a predicted time point.

8. The method of any one of items 4-7, further comprising the step of obtaining a reference pressure signal from a reference sensor (4a-4c) in the first fluid containing system (S1), wherein the reference sensor (4a-4c) is arranged to detect said second pulses even if the fluid connection (C) is compromised, and calculating the predicted temporal signal profile based on the reference pressure signal.

9. The method of item 8, further comprising the steps of calculating a magnitude value indicative of the magnitude of the second pulses in the reference pressure signal, and comparing the magnitude value to a limit, wherein the step of calculating the predicted temporal signal profile based on the reference pressure signal is conditioned upon said step of comparing.

10. The method of item 8 or 9, wherein the step of calculating the predicted temporal signal profile comprises adjusting for a difference in transit time between the reference sensor and said at least one pressure sensor.

11. The method of item 10, wherein said difference in transit time is given by a predefined value.

12. The method of item 10, wherein said difference in transit time is calculated based on a difference in fluid pressure between the location of the reference sensor and said at least one pressure sensor.

13. The method of any preceding item, wherein the time window is selected so as to contain at least one second pulse.

14. The method of item 13, wherein the length of the time window is chosen to exceed a maximum pulse repetition interval of the second pulse generator (3').

15. The method of item 13 or 14, wherein the time window is chosen based on timing information indicative of the timing of the second pulses in said at least one measurement signal.

16. The method of any preceding item, wherein said monitoring signal is generated by: filtering said at least one measurement signal to remove the first pulses; deriving, based on timing information indicative of the timing of the second pulses in said at least one measurement signal, a set of signal segments in the thus-filtered measurement signal(s); and aligning and adding the signal segments, based on the timing information, to generate said monitoring signal.

17. The method of any preceding item, wherein said calculating comprises: identifying a candidate second pulse in the monitoring signal and a corresponding candidate time point; and validating the candidate second pulse based on the candidate time point in relation to timing information indicative of the timing of the second pulses in said at least one measurement signal.

18. The method of any one of items 15-17, wherein the timing information is obtained from a pulse sensor coupled to the second fluid containing system (3').

19. The method of any one of items 15-17, wherein the timing information is obtained as a function of the relative timing of second pulses identified based on preceding parameter values.

20. The method of any one of items 15-17, wherein the first fluid containing system (S1) is an extracorporeal blood flow circuit (20) comprising an arterial access device (1), a blood processing device (6), and a venous access device (14), wherein the second fluid containing system (S2) is a human blood system comprising a blood vessel access, wherein the arterial access device (1) is connected to the human blood system, wherein the venous access device (14) is connected to the blood vessel access to form the fluid connection (C), wherein the first pulse generator (3) is a pumping device arranged in the extracorporeal blood flow circuit (20) to pump blood from the arterial access device (1) through the blood processing device (6) to the venous access device (14), wherein said at least one measurement signal comprises at least one venous measurement signal derived from at least one venous pressure sensor (4c) located downstream of the pumping device (3), and at least one arterial measurement signal derived from at least one arterial pressure sensor (4a) located upstream of the pumping device (3), and wherein the monitoring signal is generated based on said at least one venous measurement signal, said method comprising: identifying at least one second pulse in said at least one arterial measurement signal; and calculating the timing information from the thus-identified second pulse(s).

21. The method of any one of items 15-17, further comprising: intermittently turning off the first pulse generator (3); identifying at least one second pulse in said at least one measurement signal; and calculating the timing information from the thus-identified second pulse.

22. The method of any one of items 15-17, further comprising: identifying a set of candidate second pulses based on said at least one measurement signal; deriving a sequence of candidate time points based on the set of candidate second pulses; validating the sequence of candidate time points against a temporal criterion; and calculating the timing information as a function of the thus-validated sequence of candidate time points.

23. The method of any preceding item, wherein the first fluid containing system (S1) is an extracorporeal blood processing system (20) comprising an access device (1, 14), wherein the second fluid containing system (S2) is a human blood system comprising a blood vessel access, and wherein a connection between the access device (1, 14) and the blood vessel access forms the fluid connection (C).

24. A computer program product comprising instructions for causing a computer to perform the method of any one of item 1-23.

25. A device for monitoring the integrity of a fluid connection (C) between first and second fluid containing systems (S1, S2) based on at least one time-dependent measurement signal from at least one pressure sensor (4a-4c) in the first fluid containing system (S1), wherein the first fluid containing system (S1) comprises a first pulse generator (3), and the second fluid containing system (S2) comprises a second pulse generator (3'), and wherein said at least one pressure sensor (4a-4c) is arranged to detect first pulses originating from the first pulse generator (3) and second pulses originating from the second pulse generator (3'), said device comprising:
an input (28) for said at least one measurement signal; and
a signal processor (29) connected to said input (28) and comprising a processing module (52) configured to generate, based on said at least one measurement signal, a time-dependent monitoring signal in which the first pulses are essentially eliminated, and to calculate a parameter value based on signal values within a time window in the monitoring signal, the parameter value representing a distribution of the signal values, said signal processor (29) being configured to determine the integrity of the fluid connection (C) based at least partly on the parameter value.

26. A device for monitoring the integrity of a fluid connection (C) between first and second fluid containing systems (S1, S2) based on at least one time-dependent measurement signal from at least one pressure sensor (4a-4c) in the first fluid containing system (S1), wherein the first fluid containing system (S1) comprises a first pulse generator (3), and the second fluid containing system (S2) comprises a second pulse generator (3"), and wherein said at least one pressure sensor (4a-4c) is arranged to detect first pulses originating from the first pulse generator (3) and second pulses originating from the second pulse generator (3"), said device comprising:
means (28) for receiving said at least one measurement signal;
means (52) for generating, based on said at least one measurement signal, a time-dependent monitoring signal in which the first pulses are essentially eliminated;
means (52) for calculating a parameter value based on signal values within a time window in the monitoring signal, the parameter value representing a distribution of the signal values; and
means (52) for determining the integrity of the fluid connection (C) based at least partly on the parameter value.

27. A method for monitoring the integrity of a fluid connection (C) between first and second fluid containing systems (S1, S2) based on at least one time-dependent measurement signal from at least one pressure sensor (4a-4c) in the first fluid containing system (S1), wherein the first fluid containing system (S1) comprises a first pulse generator (3), and the second fluid containing system (S2) comprises a second pulse generator (3'), and wherein said at least one pressure sensor (4a-4c) is arranged to detect first pulses originating from the first pulse generator (3) and second pulses originating from the second pulse generator (3'), said method comprising:
receiving said at least one measurement signal;
obtaining timing information indicative of the timing of the second pulses in said at least one measurement signal;
processing said at least one measurement signal based on the timing information, to calculate a parameter value indicative of presence or absence of the second pulses; and
determining the integrity of the fluid connection (C) based at least partly on the parameter value.

28. The method of item 27, wherein said processing comprises: locating a time window in the measurement signal, or a monitoring signal obtained therefrom, based on the timing information; and calculating the parameter value based on the signal values within said time window.

29. The method of item 28, wherein said processing further comprises: selecting the length of the time window based on the timing information.

30. The method of any one of items 27-29, wherein said processing comprises: generating a time-dependent monitoring signal by filtering said at least one measurement signal to remove the first pulses; wherein the parameter value is calculated based on the monitoring signal.

31. The method of item 30, wherein said generating further comprises: selecting a set of signal segments in the thus-filtered measurement signal(s); and aligning and adding the signal segments, based on the timing information, to generate the monitoring signal.

32. The method of item 30 or 31, wherein said calculating comprises: identifying a candidate second pulse in the monitoring signal and a corresponding candidate time point; and validating the candidate second pulse based on the candidate time point in relation to the timing information.

33. The method of any one of items 27-32, wherein the timing information is obtained from a pulse sensor coupled to the second fluid containing system (S2).

34. The method of any one of items 27-32, wherein the timing information is obtained as a function of the relative timing of second pulses identified based on preceding parameter values.

35. The method of any one of items 27-32, further comprising the step of obtaining a reference pressure signal from a reference sensor ($4a$-$4c$) in the first fluid containing system (S1), wherein the reference sensor ($4a$-$4c$) is arranged to detect said second pulses even if the fluid connection (C) is compromised, and wherein said step of obtaining the timing information comprises: identifying at least one second pulse in the reference pressure signal and obtaining an estimated difference in arrival time between the reference sensor and said at least one pressure sensor.

36. The method of item 35, wherein the estimated difference in arrival time is given by a predefined value.

37. The method of item 35, wherein the estimated difference in arrival time is calculated based on a difference in fluid pressure between the location of the reference sensor and said at least one pressure sensor.

38. The method of any one of items 35-37, further comprising the steps of calculating a magnitude value indicative of the magnitude of said at least one second pulse in the reference pressure signal, and comparing the magnitude value to a limit, wherein the step of obtaining an estimated difference in arrival time is conditioned upon said step of comparing.

39. The method of any one of items 27-32, wherein the first fluid containing system (S1) is an extracorporeal blood flow circuit comprising an arterial access device (1), a blood processing device (6), and a venous access device (14), wherein the second fluid containing system (S2) is a human blood system comprising a blood vessel access, wherein the arterial access device (1) is connected to the human blood system, wherein the venous access device (14) is connected to the blood vessel access to form the fluid connection (C), wherein the first pulse generator (3) is a pumping device arranged in the extracorporeal blood flow circuit (20) to pump blood from the arterial access device (1) through the blood processing device (6) to the venous access device (14), wherein said at least one measurement signal comprises at least one venous measurement signal derived from at least one venous pressure sensor ($4c$) located downstream of the pumping device (3), and at least one arterial measurement signal derived from at least one arterial pressure sensor ($4a$) located upstream of the pumping device (3), and wherein the monitoring signal is generated based on said at least one venous measurement signal, said method comprising: identifying at least one second pulse in said at least one arterial measurement signal; and calculating the timing information from the thus-identified second pulse(s).

40. The method of any one of items 27-32, further comprising: intermittently turning off the first pulse generator (3); identifying at least one second pulse in said at least one measurement signal; and calculating the timing information from the thus-identified second pulse.

41. The method of any one of items 27-32, further comprising: identifying a set of candidate second pulses based on said at least one measurement signal; deriving a sequence of candidate time points based on the set of candidate second pulses; validating the sequence of candidate time points against a temporal criterion; and calculating the timing information as a function of the thus-validated sequence of candidate time points.

42. The method of item 27, wherein said obtaining further comprises: identifying a set of candidate second pulses based on said at least one measurement signal; deriving a sequence of candidate time points based on the set of candidate second pulses; generating a set of validated candidate second pulses by validating the sequence of candidate time points against a temporal criterion; wherein said processing comprises: calculating a set of average representations, each average representation being formed by aligning and adding signal segments of said at least one measurement signal that correspond to a unique combination of validated candidate second pulses; and calculating the parameter value for each of said average representations; and wherein said determining comprises comparing a maximum parameter value to a threshold value.

43. The method of any one of items 27-42, wherein the parameter value represents a distribution of signal values.

44. A computer program product comprising instructions for causing a computer to perform the method of any one of item 27-43.

45. A device for monitoring the integrity of a fluid connection (C) between first and second fluid containing systems (S1, S2) based on at least one time-dependent measurement signal from at least one pressure sensor ($4a$-$4c$) in the first fluid containing system (S1), wherein the first fluid containing system (S1) comprises a first pulse generator (3), and the second fluid containing system (S2) comprises a second pulse generator (3'), and wherein said at least one pressure sensor ($4a$-$4c$) is arranged to detect first pulses originating from the first pulse generator (3), and second pulses originating from the second pulse generator (3'), said device comprising:

an input (28) for said at least one measurement signal; and a signal processor (29) connected to said input (28) and comprising a processing module (52) configured to obtain timing information indicative of the timing of the second pulses in said at least one measurement signal, and to process said at least one measurement signal based on the timing information so as to generate a parameter value indicative of presence or absence of the second pulses, said signal processor (29) being configured to determine the integrity of the fluid connection (C) based at least partly on the parameter value.

46. A device for monitoring the integrity of a fluid connection between first and second fluid containing systems (S1, S2) based on at least one time-dependent measurement signal from at least one pressure sensor (4a-4c) in the first fluid containing system (S1), wherein the first fluid containing system (S1) comprises a first pulse generator (3), and the second fluid containing system (S2) comprises a second pulse generator (3'), and wherein said at least one pressure sensor (4a-4c) is arranged to detect first pulses originating from the first pulse generator (3), and second pulses originating from the second pulse generator (3'), said device comprising:

means (28) for receiving said at least one measurement signal;

means (52) for obtaining timing information indicative of the timing of the second pulses in said at least one measurement signal;

means (52) for processing said at least one measurement signal based on the timing information, to generate a parameter value indicative of presence or absence of the second pulses, and means (52) for determining the integrity of the fluid connection (C) based at least partly on the parameter value.

End Appendix B

The invention claimed is:

1. A device for detecting a reversed configuration of withdrawal and return devices coupling an extracorporeal blood flow circuit to a cardiovascular system of a subject, wherein the withdrawal and return devices are configurable in a normal configuration and the reversed configuration, wherein in the normal configuration the withdrawal device is in an upstream position of said cardiovascular system for withdrawal of fluid and the return device is in a downstream position of the cardiovascular system for return of fluid, and further wherein in the reversed configuration the positioning of the return and withdrawal devices is reversed, the device comprising:

a primary pressure sensor in the extracorporeal blood flow circuit, the primary pressure sensor configured to provide a primary measurement signal comprising at least a subject pulse from a subject pulse generator in the cardiovascular system;

a signal processor configured to:
receive the primary measurement signal obtained by the primary pressure sensor in the extracorporeal blood flow circuit;
process the primary measurement signal for extraction of primary pressure data originating from the subject pulse generator in the cardiovascular system, the primary pressure data comprising at least a part of the subject pulse from the subject pulse generator;
calculate a parameter value from the primary pressure data; and
determine the reversed configuration based at least partly on the parameter value calculated from the primary pressure data comprising at least a part of the subject pulse from the subject pulse generator; and a notification apparatus to provide a notification when the reversed configuration has been determined.

2. The device of claim 1, wherein the reversed configuration is determined by comparing the parameter value with a reference parameter value.

3. The device of claim 1, wherein the signal processor is further configured to receive a secondary measurement signal obtained from a secondary pressure sensor.

4. The device of claim 3, wherein the secondary pressure sensor is a pressure sensor in the extracorporeal blood flow circuit, and wherein said secondary measurement signal is processed for extraction of secondary pressure data originating from said subject pulse generator, and wherein said parameter value is calculated from the primary pressure data and the secondary pressure data.

5. The device of claim 4, wherein the primary pressure sensor is located on a venous side of the extracorporeal blood flow circuit and the secondary pressure sensor is located on an arterial side of the extracorporeal blood flow circuit.

6. The device of claim 4, wherein the parameter value is represented by a pressure amplitude ratio R of said primary pressure data and the pressure amplitude ratio R in a reversed configuration is greater than the pressure amplitude ratio R in a normal configuration.

7. The device of claim 3, wherein the parameter value represents a time delay of a pressure pulse detected by said primary pressure sensor at a first instance in time and said pressure pulse subsequently detected by said secondary pressure sensor at a second instance in time.

8. The device of claim 3, wherein the parameter value represents a deviation in transit time of the subject pulse from the subject pulse generator to the primary pressure sensor and the secondary pressure sensor.

9. The device of claim 1, wherein the parameter value is represented by a pressure amplitude measure of the primary pressure data.

10. The device of claim 9, wherein said pressure amplitude measure comprises an arterial pressure amplitude Ha or a venous pressure amplitude Hv.

11. The device of claim 1, wherein the parameter value has been derived from one or more of a plurality of monitoring sessions of one subject, a plurality of monitoring sessions of two or more subjects, and a mathematical model.

12. The device of claim 1, wherein the withdrawal and return devices comprise single or double lumen needles or catheters.

13. The device of claim 1, wherein further to calculating, the signal processor is further configured to extract shape indicative data from the primary pressure data and matching the shape indicative data with shape reference data and the parameter value represents a deviation between the shape indicative data and the shape reference data.

14. The device of claim 13, wherein the shape reference data represents a temporal pulse profile of the subject pulse generator.

15. The device of claim 13, wherein the shape reference data represents a frequency spectrum of the subject pulse generator.

16. The device of claim 1, wherein the signal processor is further configured to aggregate a plurality of pulses within an aggregation time window in the measurement signal.

17. The device of claim 1, further comprising an alarm device being configured to issue an alarm subsequent to determining a reverse configuration of access devices.

18. A method for detecting a reversed configuration of withdrawal and return devices coupling an extracorporeal blood flow circuit to a cardiovascular system of a subject, wherein the withdrawal and return devices are configurable in a normal configuration and the reversed configuration, wherein in the normal configuration the withdrawal device is in an upstream position of said cardiovascular system for withdrawal of fluid and the return device is in a downstream position of the cardiovascular system for return of fluid, and further wherein in the reversed configuration the positioning of the return and withdrawal devices is reversed, the method comprising:

receiving a primary measurement signal obtained by a primary pressure sensor in the extracorporeal blood flow circuit, wherein the primary measurement signal comprises at least a subject pulse from a subject pulse generator in the cardiovascular system;
processing the primary measurement signal for extraction of primary pressure data originating from the subject pulse generator in the cardiovascular system, the primary pressure data comprising at least a part of the subject pulse from the subject pulse generator;
calculating a parameter value from the primary pressure data;
determining the reversed configuration based at least partly on the parameter value calculated from the primary pressure data comprising at least a part of the subject pulse from the subject pulse generator; and
providing a notification when the reversed configuration has been determined.

19. The method of claim 18, wherein the configuration is determined by comparing the parameter value with a reference parameter value.

20. The method of claim 18, further comprising receiving a secondary measurement signal obtained from a secondary pressure sensor.

21. The method of claim 20, wherein the parameter represents a deviation in transit time of the subject pulse from the subject pulse generator to the primary pressure sensor and the secondary pressure sensor.

22. The method of claim 18, further comprising extracting shape indicative data from the primary pressure data and matching the shape indicative data with shape reference data.

23. The method of claim 22, further comprising receiving a secondary measurement signal obtained from a secondary pressure sensor and extracting the shape reference data from the secondary measurement signal received from the secondary pressure sensor.

24. The method of claim 18, further comprising aggregating a plurality of pulses within an aggregation time window in the measurement signal.

25. The method of claim 18, further comprising issuing an alarm subsequent to determining a reverse configuration of access devices.

26. A computer-readable medium comprising computer instructions which, when executed by a processor in an extracorporeal blood treatment system, cause the processor to detect a reversed configuration of withdrawal and return devices coupling an extracorporeal blood flow circuit to a cardiovascular system of a subject by:
receiving a primary measurement signal obtained by a primary pressure sensor in the extracorporeal blood flow circuit, wherein the primary measurement signal comprises at least a subject pulse from a subject pulse generator in the cardiovascular system;
processing the primary measurement signal for extraction of primary pressure data originating from the subject pulse generator in the cardiovascular system, the primary pressure data comprising at least a part of the subject pulse from the subject pulse generator;
calculating a parameter value from the primary pressure data;
determining the reversed configuration based at least partly on the parameter value calculated from the primary pressure data comprising at least a part of the subject pulse from the subject pulse generator, wherein the withdrawal and return devices are configurable in a normal configuration and the reversed configuration, wherein in the normal configuration the withdrawal device is in an upstream position of said cardiovascular system for withdrawal of fluid and the return device is in a downstream position of the cardiovascular system for return of fluid, and further wherein in the reversed configuration the positioning of the return and withdrawal devices is reversed; and
generating a signal to initiate notification of determination of the reversed configuration.

27. A device for detecting a reversed configuration of withdrawal and return devices coupling an extracorporeal blood flow circuit to a cardiovascular system of a subject, wherein the withdrawal and return devices are configurable in a normal configuration and the reversed configuration, wherein in the normal configuration the withdrawal device is in an upstream position of said cardiovascular system for withdrawal of fluid and the return device is in a downstream position of the cardiovascular system for return of fluid, and further wherein in the reversed configuration the positioning of the return and withdrawal devices is reversed, said device comprising:
primary pressure sensing means in the extracorporeal blood flow circuit, the primary pressure sensing means for providing a primary measurement signal comprising at least a subject pulse from a subject pulse generator in the cardiovascular system;
means for receiving the primary measurement signal obtained by the primary pressure sensing means in the extracorporeal blood flow circuit;
means for processing the primary measurement signal for extraction of primary pressure data originating from the subject pulse generator in the cardiovascular system, the primary pressure data comprising at least a part of the subject pulse from the subject pulse generator;
means for calculating a parameter value from the primary pressure data;
means for determining the reversed configuration based at least partly on the parameter value calculated from the primary pressure data comprising at least a part of the subject pulse from the subject pulse generator; and
means for providing a notification when the reversed configuration has been determined.

28. A device for detecting a reversed configuration of withdrawal and return devices coupling an extracorporeal blood flow circuit to a cardiovascular system of a subject, wherein the withdrawal and return devices are configurable in a normal configuration and the reversed configuration, wherein in the normal configuration the withdrawal device is in an upstream position of said cardiovascular system for withdrawal of fluid and the return device is in a downstream position of the cardiovascular system for return of fluid, and further wherein in the reversed configuration the positioning of the return and withdrawal devices is reversed, the device comprising:
a primary pressure sensor in the extracorporeal blood flow circuit, the primary pressure sensor configured to provide a primary measurement signal comprising at least a pump pulse from a pump pulse generator;
a signal processor configured to:
receive the primary measurement signal obtained by the primary pressure sensor in the extracorporeal blood flow circuit;
process the primary measurement signal for extraction of primary pressure data originating from the pump pulse generator in the extracorporeal blood flow circuit, the primary pressure data comprising at least a part of the pump pulse from the pump pulse generator;
calculate a parameter value from the primary pressure data, the parameter value being indicative of a crosstalk pressure pattern generated from a combination of pressure pulses from the pump pulse generator obtained by the primary pressure sensor from two directions, one passing through the cardiovascular system of the subject and the other from the pump pulse generator within the extracorporeal circuit; and determine the reversed configuration based at least partly on the parameter value calculated from the primary pressure data; and a notification apparatus to provide a notification when the reversed configuration has been determined.

29. A method for detecting a reversed configuration of withdrawal and return devices coupling an extracorporeal blood flow circuit to a cardiovascular system of a subject, wherein the withdrawal and return devices are configurable in a normal configuration and the reversed configuration, wherein in the normal configuration the withdrawal device is in an upstream position of said cardiovascular system for withdrawal of fluid and the return device is in a downstream position of the cardiovascular system for return of fluid, and further wherein in the reversed configuration the positioning of the return and withdrawal devices is reversed, the method comprising:

receiving a primary measurement signal obtained by a primary pressure sensor in the extracorporeal blood flow circuit, wherein the primary measurement signal comprises at least a pump pulse from a pump pulse generator;

processing the primary measurement signal for extraction of primary pressure data originating from the pump pulse generator in the extracorporeal blood flow circuit, the primary pressure data comprising at least a part of the pump pulse from the pump pulse generator;

calculating a parameter value from the primary pressure data, the parameter value being indicative of a cross-talk pressure pattern generated from a combination of pressure pulses from the pump pulse generator obtained by the primary pressure sensor from two directions, one passing through the cardiovascular system of the subject and the other from the pump pulse generator within the extracorporeal circuit; and determining the reversed configuration based at least partly on the parameter value calculated from the primary pressure data; and providing a notification when the reversed configuration has been determined.

* * * * *